US006407268B1

(12) United States Patent
Engel et al.

(10) Patent No.: US 6,407,268 B1
(45) Date of Patent: Jun. 18, 2002

(54) SUBSTITUTED 4-BENZOYLPYRAZOLES

(75) Inventors: Stefan Engel, Idstein; Ernst Baumann, Dudenhofen; Wolfgang von Deyn, Neustadt; Regina Luise Hill, Speyer; Uwe Kardorff, Mannheim; Guido Mayer, Neustadt; Martina Otten, Ludwigshafen; Joachim Rheinheimer, Ludwigshafen; Oliver Wagner, Ludwigshafen; Matthias Witschel, Ludwigshafen; Ulf Misslitz, Neustadt; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/588,666

(22) Filed: Jun. 6, 2000

Related U.S. Application Data

(62) Division of application No. 09/423,078, filed as application No. PCT/EP98/02622 on May 4, 1998, now Pat. No. 6,140,272.

(30) Foreign Application Priority Data

May 7, 1997 (DE) ........................................ 197 19 387

(51) Int. Cl.$^{7}$ ............................................. C07D 305/14

(52) U.S. Cl. .................... 549/511; 546/281.7; 548/204; 548/236; 548/247; 548/517; 549/60; 549/332; 549/214; 549/473; 549/510; 549/554; 549/561

(58) Field of Search ................................ 549/510, 511, 549/561

(56) References Cited

FOREIGN PATENT DOCUMENTS

EP 352543 * 7/1989

WO WO96/26206 * 8/1996

* cited by examiner

*Primary Examiner*—Ba K. Trinh

(74) *Attorney, Agent, or Firm*—Keil & Weinkauf

(57) ABSTRACT

4-Benzoylpyrazoles of the formula I

I

O, Q, A, $R^1$, $R^2$ where:

$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl, —$OR^{10}$, —$OCOR^{10}$, —$OSO_2R^{10}$, —$S(O)_nR^{10}$, —$SO_2OR^{10}$, —$SO_2NR^3R^{10}$, —$NR^{10}SO_2R^{10}$ or —$NR^{10}COR$;

Q is a pyrazole of the formula II,

II $R^{13}$, 4, N, N, $OR^{12}$, $R^{11}$ which is attached in position 4 and,

Substituted 4-benzoylpyralozoles.

14 Claims, No Drawings

SUBSTITUTED 4-BENZOYLPYRAZOLES

This application is a divisional of Ser. No. 09/423,075 filed Nov. 2, 1999, now U.S. Pat. No. 6,140,272, which is a 371 of PCT/EP98/02622 dated May 4, 1998.

The present invention relates to substituted 4-benzoylpyrazoles of the formula I

I

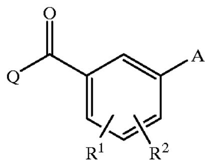

where:

$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl, —$OR^{10}$, —$OCOR^{10}$, —$OSO_2R^{10}$, —$S(O)_nR^{10}$, —$SO_2OR^{10}$, —$SO_2NR^3R^{10}$, —$NR^{10}SO_2R^{10}$ or —$NR^{10}COR^{10}$;

Q is a pyrazole of the formula II,

II

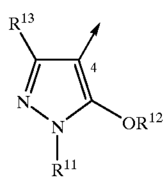

which is attached in position 4 and where $R^{11}$ is $C_1$–$C_6$-alkyl, $C_1$–$C_6$-haloalkyl, phenyl or phenyl which is partially or fully halogenated and/or carries one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$R^{12}$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonyl, phenylcarbonylmethyl, phenoxycarbonyl or phenylsulfonyl, where the last four substituents are unsubstituted or the phenyl ring in question is partially or fully halogenated and/or carries one to three of the following radicals: nitro, cyano, $C_1$–$C_4$-alkyl, $C_1$–$C_4$-haloalkyl, $C_1$–$C_4$-alkoxy , $C_1$–$C_4$-haloalkoxy;

$R^{13}$ is hydrogen, $C_1$–$C_6$-alkyl or $C_1$–$C_6$-haloalkyl;

A is a group of the formula IIIa, IIIb or IV

IIIa

-continued

IIIb

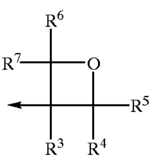

IV

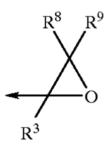

where:

$R^3$ is hydrogen, $C_1$–$C_6$-alkyl or phenyl, where the alkyl and phenyl radicals mentioned may be partially or fully halogenated and/or may carry one to three of the following groups:

hydroxy, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted;

$R^4$–$R^7$ may be identical or different and, independently of the others, each is:

hydrogen, hydroxyl, mercapto, amino, halogen, $C_1$–$C_6$-alkyl, $C_3$–$C_6$-cycloalkyl, $C_4$–$C_6$-cycloalkenyl, phenyl, —$OR^{10}$, —$S(O)_nR^{10}$, —$OS(O)_nR^{10}$, —$PO(OR^{10})_2$, —$NR^3R^{10}$, —$Si(R^{10})_3$ or —$OCOR^{10}$, where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$, —$Si(R^{10})_3$, —$OCOR^{10}$ may be partially or fully halogenated, and the unsubstituted or partially halogenated alkyl, cycloalkyl and $R^3$ radicals optionally carry one to three of the following groups: hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted, and the unsubstituted or partially halogenated $R^{10}$ radicals optionally carry one to three of the following groups: hydroxyl, mercapto, amino, cyano, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted;

$R^4$ and $R^5$ together may form a $C_2$–$C_5$-alkylene- or $C_2$–$C_5$-alkenylene chain which may be interrupted once or twice by a nitrogen or an oxygen atom, or may form a group =X, where X is an oxygen atom or a group $CR^3R^{10}$, $NR^{10}$, $NNR^3R^{10}$ or $NOR^{10}$;

$R^6$ and $R^7$ together may form a $C_2$–$C_5$-alkylene- or $C_2$–$C_5$-alkenylene chain which may be interrupted once or twice by a nitrogen or an oxygen atom, or may form a group =X, where X is an oxygen atom or a group $CR^3R^{10}$, $NR^{10}$, $NNR^3R^{10}$ or $NOR^{10}$;

n is zero, one, two;

$R^5$ and $R^6$ together may furthermore, if they are attached to adjacent carbon atoms and if $R^4$ and $R^7$ are hydrogen, form a $C_3$–$C_4$-alkylene or $C_3$–$C_4$-alkenylene chain which may be interrupted by a nitrogen or an oxygen atom;

$R^8$ and $R^9$ may be identical or different and, independently of the other, each is:

hydrogen, nitro, halogen, cyano, $C_1$–$C_6$-alkyl, $C_3$–$C_6$-cycloalkyl, $C_4$–$C_6$-cycloalkenyl, $C_5$–$C_6$-heterocyclyl, —$OR^{10}$, —$SR^{10}$, —$COR^{10}$, —$COOR^{10}$, —$CONR^3R^{10}$, phenyl, phenyl-$C_1$–$C_6$-alkyl and five- or six-membered hetaryl, where the alkyl and cycloalkyl radicals mentioned and $R^3$ and $R^{10}$ of the radicals —$OR^{10}$, —$SR^{10}$, —$COR^{10}$, —$COOR^{10}$, —$CONR^3R^{10}$ may be partially or fully halogenated, and the unsubstituted or partially halogenated alkyl, cycloalkyl and $R^3$ radicals optionally carry one to three of the following groups: hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted, and the unsubstituted or partially halogenated $R^{10}$ radicals optionally carry one to three of the following groups: hydroxyl, mercapto, amino, cyano, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted;

$R^{10}$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl, where the alkyl radicals mentioned may be partially or fully halogenated and/or may carry one to three of the following groups: hydroxyl, mercapto, amino, cyano, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted;

and agriculturally useful salts thereof.

In addition, the invention relates to processes and intermediates for preparing compounds of the formula I, to compositions comprising them, and to the use of the compounds of the formula I and to compositions comprising them for controlling harmful plants.

4-Benzoylpyrazoles are disclosed in the literature, for example in EP-A 282 944.

However, the herbicidal properties of the prior art compounds and their crop plant safety are not entirely satisfactory. It is an object of the present invention to provide novel, in particular herbicidally active, compounds having improved properties.

We have found this object is achieved by the 4-benzoylpyrazoles of the formula I and their herbicidal activity.

Furthermore, we have found herbicidal compositions which comprise the compounds I and have very good herbicidal activity. Moreover, we have found processes for preparing these compositions and methods for controlling undesirable vegetation using the compounds I.

The present invention also provides stereoisomers of the compounds of the formula I. Pure stereoisomers and also mixtures thereof are included.

Depending on the substitution pattern, the compounds of the formula I may contain one or more chiral centers and, if this is the case, are present as mixtures of enantiomers or diastereomers. The invention provides the pure enantiomers or diastereomers and also mixtures thereof.

The compounds of the formula I may also be present in the form of their agriculturally useful salts, the kind of salt generally not being important. The salts of those cations or the acid addition salts of those acids whose cations or anions, respectively, do not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and ammonium, where, if desired, one to four hydrogen atoms may be replaced by $C_1$–$C_4$-alkyl or hydroxyl-$C_1$–$C_4$-alkyl and/or one phenyl or benzyl, preferably diisopropylammonium, tetramethylammonium, tetrabutylammonium, trimethylbenzylammonium, furthermore phosphonium ions, sulfonium ions, preferably tri($C_1$–$C_4$-alkyl)sulfonium and sulfoxonium ions, preferably tri($C_1$–$C_4$-alkyl)sulfoxonium.

Anions of useable acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

Process A

Reactions of pyrazoles of the formula II (where $R^{12}$=H) with an activated carboxylic acid Va or a carboxylic acid Vb, which is preferably activated in situ, to give the acylation product VII, and subsequent rearrangements to the compounds of the formula I according to the invention.

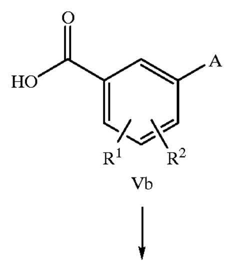

-continued

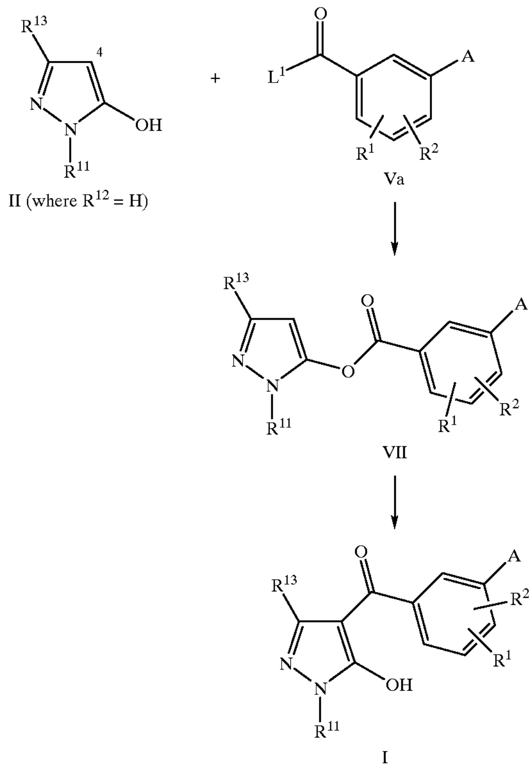

$L^1$ is a nucleophilically replaceable leaving group such as halogen, for example bromine or chlorine, hetaryl, for example imidazolyl or pyridyl, or carboxylate, for example acetate, trifluoroacetate, etc.

The activated carboxylic acid can be employed directly, as in the case of the acyl halides, or be generated in situ, for example by using dicyclohexylcarbodiimide, triphenylphosphine/azodicarboxylic esters, 2-pyridine disulfite/triphenylphosphine, carbonyldiimidazole, etc.

It may be advantageous to carry out the acylation reaction in the presence of a base. Starting materials and auxiliary base are advantageously employed in equimolar amounts. A slight excess of auxiliary base, for example 1.2 to 1.5 mol equivalents, based on II, may be advantageous under certain circumstances.

Suitable auxiliary bases are tertiary alkylamines, pyridine or alkali metal carbonates. Examples of solvents which can be used are chlorinated hydrocarbons, such as methylene chloride, 1,2-dichloroethane, aromatic hydrocarbons, such as toluene, xylene, chlorobenzene, ethers, such as diethyl ether, methyl tert-butyl ether, tetrahydrofuran, dioxane, polar aprotic solvents, such as acetonitrile, dimethylformamide, dimethyl sulfoxide, or esters such as ethyl acetate or mixtures of these.

If acyl halides are employed as activated carboxylic acid component, it may be advantageous to cool the reaction mixture to 0–10° C. when adding this reaction partner. The mixture is subsequently stirred at 20–100° C., preferably at 25–50° C., until the reaction is complete. Work-up is carried out in the customary manner, for example by pouring the reaction mixture into water and extracting the product of value. Solvents which are particularly suitable for this purpose are methylene chloride, diethyl ether and ethyl acetate. After the organic phase has been dried and the solvent has been removed, the crude enol ester of the formula VII is purified, preferably by chromatography.

Alternatively, it is possible to employ the crude enol ester of the formula VII without further purification for the rearrangement reaction.

The rearrangement of the enol esters of the formula VII to the compounds of the formula I is advantageously carried out at from 20 to 40° C. in a solvent and in the presence of a base and, if appropriate, in the presence of a cyano compound.

Examples of solvents which can be used are acetonitrile, methylene chloride, 1,2-dichloroethane, dioxane, ethyl acetate, toluene or mixtures of these. Preferred solvents are acetonitrile and dioxane.

Suitable bases are tertiary amines such as triethylamine, pyridine or alkali metal carbonates, such as sodium carbonate, potassium carbonate, which are preferably employed in equimolar amounts or up to a four-fold excess, based on the ester. Preference is given to using triethylamine or alkali metal carbonates.

Suitable cyano compounds are inorganic cyanides such as sodium cyanide, potassium cyanide and organic cyano compounds such as acetone cyanohydrin, trimethylsilyl cyanide. They are employed in an amount of 1 to 50 mol percent, based on the ester. Preference is given to using acetone cyanohydrin or trimethylsilyl cyanide, for example, in an amount of 5 to 15, preferably 10, mol percent, based on the ester.

Particular preference is given to employing alkali metal carbonates, such as potassium carbonate, in acetonitrile or dioxane.

Work-up can be carried out in a manner known per se. For example, the reaction mixture is acidified with dilute mineral acid, such as 5% strength hydrochloric acid or sulfuric acid, and extracted with an organic solvent, for example methylene chloride, ethyl acetate. The organic phase can be extracted with 5–10% strength alkali metal carbonate solution, for example sodium carbonate or potassium carbonate solution. The aqueous phase is acidified, and the precipitate which forms is filtered off with suction and/or extracted with methylene chloride or ethyl acetate, dried and concentrated.

(Examples of the synthesis of esters from hydroxypyrazoles and the rearrangement of the esters are mentioned for example in EP-A 282 944 or U.S. Pat. No. 4,643,757).

Process B

Reactions of 4-benzoylpyrazoles of the formula I (where $R^{12}$=H) with a compound of the formula VI (where $R^{12}\neq$H):

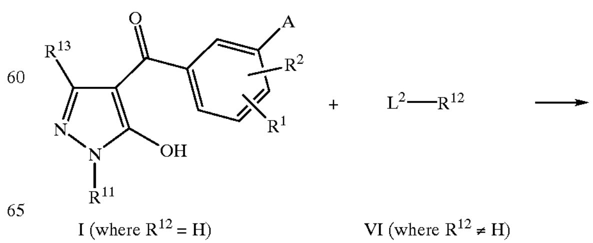

-continued

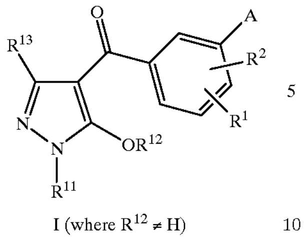

$L^2$ is a nucleophilically replaceable leaving group such as halogen, for example bromine, chlorine, hetaryl, for example imidazolyl, pyridyl, carboxylate, for example acetate, trifluoroacetate, sulfonate, for example mesylate, triflate, etc.

The compounds of the formula V can be employed directly, for example in the case of the alkyl halides, acyl halides, sulfonyl halides, carboxylic anhydrides and sulfonic anhydrides, or prepared in situ, for example activated carboxylic acids (by means of carboxylic acid and dicyclohexylcarbodiimide, carbonyldiimidazole, etc.).

In general, the starting materials are employed in an equimolar ratio. However, it may also be advantageous to employ an excess of one or the other component.

Where appropriate, it may be advantageous to carry out the reaction in the presence of a base. The starting materials and the auxiliary base are advantageously employed in equimolar amounts. Under certain circumstances, it may be advantageous to employ an excess of the auxiliary base, for example 1.5 to 3 mol equivalents, based on II.

Suitable auxiliary bases are tertiary alkylamines such as triethylamine, pyridine, alkali metal carbonates, for example sodium carbonate, potassium carbonate, and alkali metal hydrides, for example sodium hydride. Preference is given to using triethylamine, pyridine and potassium carbonate.

Examples of suitable solvents are chlorinated hydrocarbons such as methylene chloride, 1,2-dichloroethane, aromatic hydrocarbons, for example toluene, xylene, chlorobenzene, ethers, such as diethyl ether, methyl tert-butyl ether, tetrahydrofuran, dioxane, polar aprotic solvents, such as acetonitrile, dimethylformamide, dimethyl sulfoxide or esters, such as ethyl acetate, or mixtures of these.

The reaction temperature is generally in the range of from 0° C. to the boiling point of the reaction mixture.

Work-up can be carried out in a manner known per se to give the product.

The pyrazoles of the formula II (where $R^{12}$=H) used as starting materials are known or can be prepared by methods known per se (for example EP-A 240 001, J. Prakt. Chem. 315 (1973), 383).

The benzoic acids of the formula V are novel,

V

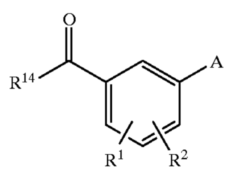

the variables having the following meanings:

$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl, —$OR^{10}$, —$OCOR^{10}$, —$OSO_2R^{10}$, —$S(O)_nR^{10}$, —$SO_2OR^{10}$, —$SO_2NR^3R^{10}$, —$NR^{10}SO_2R^{10}$ or —$NR^{10}COR^{10}$;

A is a group of the formula IIIa, IIIb or IV

IIIa

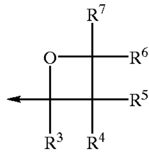

IIIb

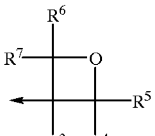

IV

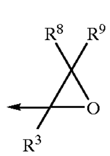

where:

$R^3$ is hydrogen, $C_1$–$C_6$-alkyl or phenyl, where the alkyl and phenyl radicals mentioned may be partially or fully halogenated and/or may carry one to three of the following groups:

hydroxy, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted;

$R^4$–$R^7$ may be identical or different and, independently of the others, each is:

hydrogen, hydroxyl, mercapto, amino, halogen, $C_1$–$C_6$-alkyl, $C_3$–$C_6$-cycloalkyl, $C_4$–$C_6$-cycloalkenyl, phenyl, —$OR^{10}$, —$S(O)_nR^{10}$, —$OS(O)_nR^{10}$, —$PO(OR^{10})_2$, —$NR^3R^{10}$, —$Si(R^{10})_3$ or —$OCOR^{10}$, where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$, —$Si(R^{10})_3$, —$OCOR^{10}$ may be partially or fully halogenated, and the unsubstituted or partially halogenated alkyl, cycloalkyl and $R^3$ radicals optionally carry one to three of the following groups:hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted, and the unsubstituted or partially halogenated $R^{10}$ radicals optionally carry one to three of the following groups:hydroxyl, mercapto, amino, cyano, $C_1$–$C_4$-alkyliminooxy, $C_1$–$C_4$-alkoxyamino, $C_1$–$C_4$- alkylcarbonyl, $C_1$–$C_4$-alkoxy-$C_2$–$C_6$-alkoxycarbonyl, $C_1C_4$-alkylsulfonyl, heterocyclyl, heterocyclyloxy, phenyl, benzyl, hetaryl, phenoxy, benzyloxy and hetaryloxy, where the last eight radicals may in turn be substituted;

$R^4$ and $R^5$ together may form a $C_2$–$C_5$-alkylene- or $C_2$–$C_5$-alkenylene chain which may be interrupted once or twice by a nitrogen or an oxygen atom, or may form a group =X, where X is an oxygen atom or a group $CR^3R^{10}$, $NR^{10}$, $NNR^3R^{10}$ or $NOR^{10}$;

$R^6$ and $R^7$ together may form a $C_2$–$C_5$-alkylene- or $C_2$–$C_5$-alkenylene chain which may be interrupted once or twice by a nitrogen or an oxygen atom, or may form a group =X, where X is an oxygen atom or a group $CR^3R^{10}$, $NR^{10}$, $NNR^3R^{10}$ or $NOR^{10}$;

n is zero, one or two;

$R^5$ and $R^6$ together may furthermore, if they are attached to adjacent carbon atoms and if $R^4$ and $R^7$ are hydrogen, form a $C_3$–$C_4$-alkylene or $C_3$–$C_4$-alkenylene chain which may be interrupted by a nitrogen or an oxygen atom;

$R^8$ and $R^9$ may be identical or different and, independently of the other, each is:

hydrogen, nitro, halogen, cyano, $C_1$–$C_6$-alkyl, $C_3$–$C_6$-cycloalkyl, $C_4$–$C_6$-cycloalkenyl, $C_5$–$C_6$-heterocyclyl, —$OR^{10}$, —$SR^{10}$, —$COR^{10}$, —$COOR^{10}$, —$CONR^3R^{10}$, phenyl, phenyl-$C_1$–$C_6$-alkyl and five- or six-membered hetaryl, where the alkyl and cycloalkyl radicals mentioned and $R^3$ and $R^{10}$ of the radicals —$OR^{10}$, —$SR^{10}$, —$COR^{10}$, —$COOR^{10}$, —$CONR^3R^{10}$ may be partially or fully halogenated, and the unsubstituted or partially halogenated alkyl, cycloalkyl and $R^3$ radicals optionally carry one to three of the following groups: hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted, and the unsubstituted or partially halogenated $R^{10}$ radicals optionally carry one to three of the following groups: hydroxyl, mercapto, amino, cyano, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted;

$R^8$ and $R^9$ together may furthermore form a $C_2$–$C_5$-alkylene- or $C_2$–$C_5$-alkenylene chain which may be interrupted once or twice by a nitrogen or an oxygen atom;

$R^{10}$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl;

$R^{14}$ is hydroxyl or a radical which can be removed by hydrolysis.

Examples of radicals which can be removed by hydrolysis are alkoxy, phenoxy, alkylthio and phenylthio radicals which can be substituted, halides, hetaryl radicals which are bonded via nitrogen, amino and imino radicals which can be substituted, etc.

Preference is given to benzoyl halides Va where $L^1$=halogen (≙V where $R^{14}$=halogen),

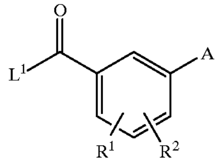

where the variables $R^1$, $R^2$, and A are each as defined under formula V and

L is halogen, in particular chlorine or bromine.

Preference is also given to benzoic acids of the formula Vb (≙V where $R^{14}$=hydroxyl),

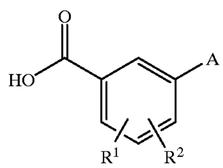

where the variables $R^1$, $R^2$, and A are each as defined under formula V.

Preference is also given to benzoic esters of the formula Vc (≙V where $R^{14}$=$C_1$–$C_6$-alkoxy),

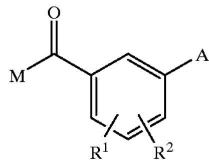

where the variables $R^1$, $R^2$, and A are each as defined under formula V and

M is $C_1$–$C_6$-alkoxy.

The compounds of the formula Va (where $L^1$=halogen) can be synthesized by methods similar to those known from the literature (cf. L. G. Fieser, M. Fieser "Reagents for Organic Synthesis", Vol. I, pp. 767–769 (1967)) by reacting benzoic acids of the formula Vb with halogenating agents such as thionyl chloride, thionyl bromide, phosgene, diphosgene, triphosgene, oxalyl chloride and oxalyl bromide.

The benzoic acids of the formula Vb can be obtained, inter alia, by hydrolyzing the benzoic esters of the formula Vc (where M=$C_1$–$C_6$-alkoxy).

The benzoic esters of the formula Vc according to the invention are preparable by various methods known from the literature (for example a: G. Dittus in Houben-Weyl, Methoden der Organischen Chemie, Volume VI/3, Oxygen Compounds I, 4th Edition, p. 493 ff., Georg Thieme Verlag, 1965; b: T. L. Gilchrist, Heterocyclenchemie, 2nd Edition, Verlag Chemie, 1995), as illustrated in the examples that follow.

Process A

Cyclization of 1,3-halohydrins of the formula VIIIa or VIIIb under alkaline reaction conditions to give the benzoic esters of the formula Vc according to the invention where the variables $R^1$, $R^2$ and M are each as defined under formula V, A is a group of the formula IIIa or IIIb and $L^2$ is a nucleophilically replaceable leaving group, preferably iodine, bromine or chlorine.

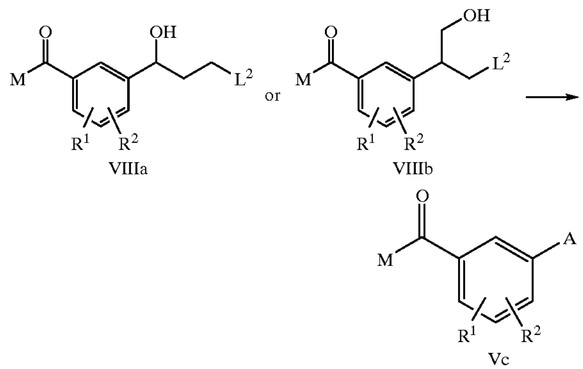

Suitable for use as cleaving agents are especially alkali metal and alkaline earth metal hydroxides, for example potassium hydroxide or sodium hydroxide, or organic bases, for example alkoxides such as sodium methoxide, or secondary amines such as diethylamine.

The elimination of hydrogen halide can be effected even by alkaline salts, for example by potassium fluoride (E. Gryszkiewics-Trochimowski, O. Gryszkiewics-Trochimowski, Bulletin de la Société Chimique de France, Mémoires 123 (1953)).

The cleaving agents may be employed in solution or neat, preferably in solution, for example methanolic sodium methoxide solution.

The cyclization is carried out in inert solvents, for example in alcohols such as methanol or ethanol.

Process B

Photochemical cycloadditions of aldehydes of the formula IX or ketones of the formula X with olefins XI, preferably with enol ethers of the formula XI (where $R^7$=$OR^{10}$), to give the benzoic esters of the formula Vc according to the invention where the variables $R^1$, $R^2$, $R^3$, $R^{10}$ and M are each as defined under formula V and A is a group of the formula IIIa.

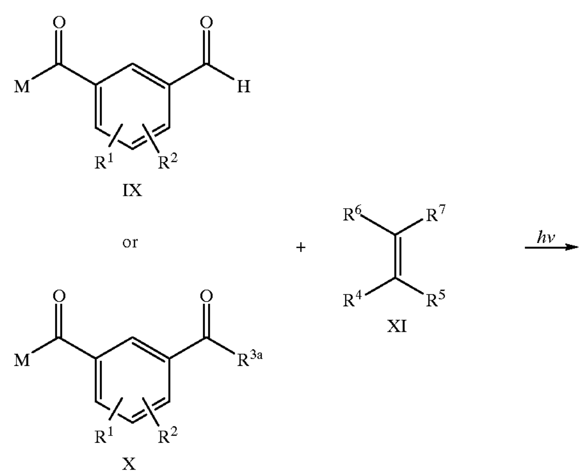

-continued

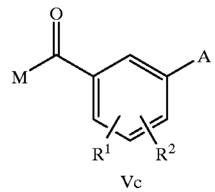

The radical $R^{3a}$ in formula X represents a radical $R^3$ which is different from hydrogen. Accordingly, the reaction of the compound of formula IX with the olefin XI results in a compound of formula Vc wherein $R^3$ denotes hydrogen, and the reaction of the compound of formula X with the olefin XI results in a compound of formula Vc wherein $R^3$ is different from hydrogen.

The photochemical cycloaddition is carried out in inert solvents which do not have any significant UV absorption in the spectral range used. Thus, for example acetonitrile or aliphatic or aromatic hydrocarbons such as n-hexane or toluene can be used.

Suitable radiation sources are appropriate UV radiators, preferably low-pressure, medium-pressure or high-pressure mercury lamps (A. M. Braun, M. T. Maurette, E. Oliveros, Photochemical Technology, John Wiley & Sons Ltd 1991). Low-pressure mercury lamps emit at 189 and 253 nm, the emission at 189 nm being almost completely absorbed by oxygen, water or solvent, so that low-pressure mercury lamps virtually emit a monochromatic radiation at 253 nm.

Medium- and high-pressure mercury lamps are operated at pressures from 1 to 100 atm and emit, depending on pressure and temperature, in a wavelength range of from 200 to 600 nm, medium-pressure mercury lamps having a dominant emission line at 366 nm and high-pressure mercury lamps having two dominant emissions at 436 and 546 nm.

Furthermore, it is possible to employ medium- and high-pressure mercury lamps which are doped with metal salts such as thallium halides, indium halides, sodium halides or gallium halides. The doping causes a modification of the emission spectrum of the medium- and high-pressure mercury lamps and results in the emission of additional emission lines characteristic for the doping in question.

In addition, it is possible to use appropriate filters which suppress undesirable wavelength ranges.

Suitable photoreactors should not absorb in the UV range used, but should be transparent for the wavelengths which are emitted by an appropriate UV radiator.

Particularly suitable for this purpose is borosilicate glass, for example borosilicate BK7 (Schott) or Corning 7740 (Pyrex) or quartz glass, which is even more transparent than borosilicate-glass in the UV range.

Preferred photoreactors are falling film-reactors.

Process C

Intramolecular cyclization of A-halofatty acids or their alkali metal salts of the formula XIIa or XIIb to give the benzoic esters of the formula Vc according to the invention where the variables $R^1$, $R^2$ and M are each as defined under formula V, A is a group of the formula IIIa or IIIb and $L^2$ is a nucleophilically replaceable leaving group, preferably iodine, bromine or chlorine.

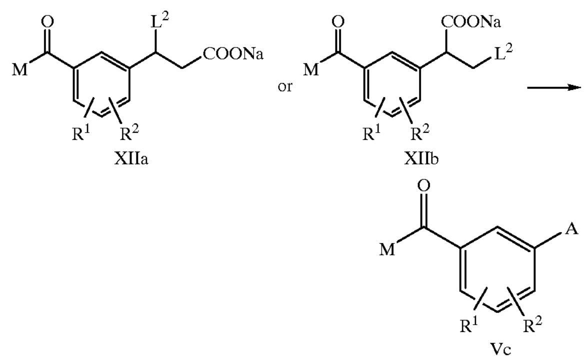

The elimination of hydrogen halide from β-halofatty acids or salts thereof, for example the sodium salts, by aqueous solutions of alkali metal salts, for example sodium carbonate solution, leads to the formation of β-lactones (A. Einhorn, Chem. Ber. 16 (1983), 2208). Instead of sodium carbonate, silver oxide or silver salts are frequently successfully used for the elimination of hydrogen halide.

Owing to the lability of the β-lactones in the presence of aqueous alkali metal halides, it is necessary to prepare water-soluble β-lactones in the presence of solvents to remove the β-lactone formed as quickly as possible from the aqueous phase (Org. Reactions 8 (1954), 309). Suitable solvents include diethyl ether and chloroform.

Process D

Cycloaddition of aldehydes of the formula IX or ketones of the formula X with ketenes XIII to give the benzoic esters of the formula Vc according to the invention where the variables $R^1$, $R^2$, $R^3$, $R^4$, $R^5$ and M are each as defined under formula V and A is a group of the formula IIIa or IIIb.

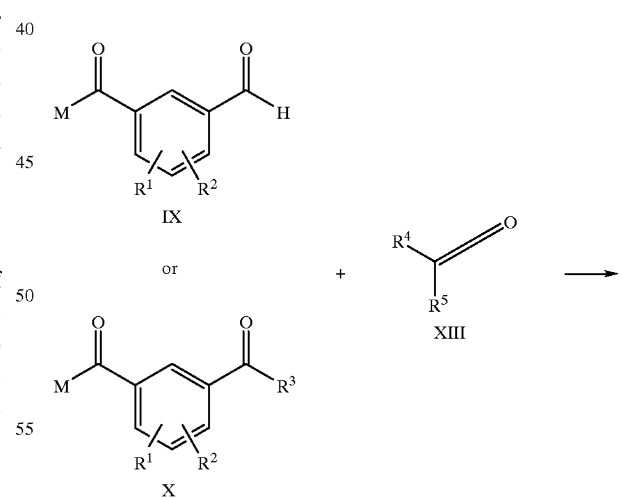

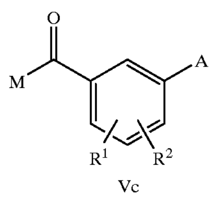

Depending on the kind of catalyst used and the reaction conditions, ketenes react with carbonyl compounds at 20–100° C., preferably at 40–80° C., to form enol acetates or β-lactones (for example H. Kröper in Houben-Weyl, Methoden der Organischen Chemie, Volume VI/2, Oxygen Compounds I, Part 2, 4th Edition, p. 511ff., Georg Thieme Verlag, 1965). The formation of β-lactones occurs after C-acetylation if basic catalysts such tertiary amines or alkali metals or alkaline earth metals are employed (J. A. Spence, E. F. Degering, Chem. Abst. 43 (1949), 6654). In the presence of specific catalysts, aldehydes or ketones condense at lower temperatures of from 0 to 10° C. with the most simple ketenes to form β-lactones.

The choice of catalyst depends on the carbonyl compounds in question. Catalysts which are suitable for aromatic aldehydes are, for example, boric acid, triacetyl borate, zinc thiocyanate and zinc chloride, aluminum chloride, mercury(II) chloride, and activated alumina and silica.

To obtain high yields, the reaction has to be carried out in an anhydrous medium.

Suitable for use as solvents are ethers, for example diethyl ether, haloalkanes, for example methylene chloride or chloroform, and, owing to the tendency of the β-lactones to polymerize, preferably ketones.

Process E

Addition of thiole ester enolates XIV to aldehydes of the formula IX or ketones of the formula X by a method similar to processes known from the literature (R. L. Danheiser, J. S. Nowick, Journal of Organic Chemistry 56 (1991), 1176) to give the benzoic esters of the formula Vc according to the invention where the variables $R^1$, $R^2$, $R^3$, $R^4$, $R^5$ and M are each as defined under formula V and A is a group of the formula IIIa or IIIb.

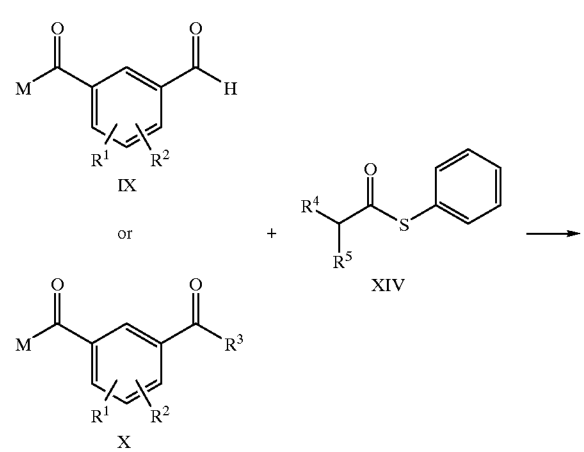

-continued

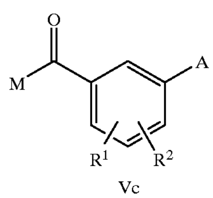

The thiole ester enolates XIV used as starting materials can be prepared in a simple one-step reaction from carboxylic acid derivatives (for example B. T. Mukaiyama, T. Takeda, K. Atsumi, Chemistry Letters 1974, 187).

The corresponding enolate, which forms the desired compounds of the formula Vc, in particular β-lactones, with aldehydes or ketones, is formed in the presence of an equivalent of a base, preferably a lithium base such as, for example, lithium diisopropylamide.

Process F

Cyclization of 1,2-halohydrins of the formula XVa or XVb under alkaline reaction conditions to give the benzoic esters of the formula Vc according to the invention where the variables $R^1$, $R^2$ and M are each as defined under formula V, A is a group of the formula IV and $L^2$ is a nucleophilically replaceable leaving group, preferably iodine, bromine or chlorine.

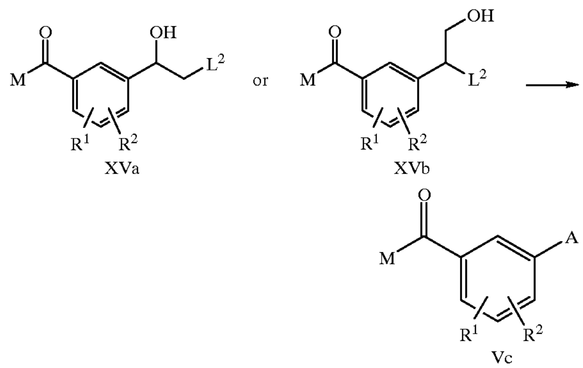

Instead of the 1,2-halohydrins, it is also possible to use their acetates as starting materials in a similar manner.

Related to the methods described is the preparation of benzoic esters of the formula Vc according to the invention by elimination of p-toluenesulfonic acid from 2-hydroxytoluene-sulfonates (for example H. Ohle, L. v. Vargha, Chemische Berichte 62, (1929), 2440).

Particularly suitable cleaving agents are alkali metal hydroxides and alkaline earth metal hydroxides; organic bases, for example alkoxides, secondary amines or pyridine and its homologs such as collidine, are less frequently used. Preferred alkali metal hydroxides and alkaline earth metal hydroxides are for example potassium hydroxide, sodium hydroxide or calcium hydroxide.

In some instances, the elimination of hydrogen halide can be effected even by alkaline salts, for example potassium carbonate, barium carbonate or potassium fluoride. Furthermore, the use of aluminates, silicates and zincates (for example J. D. Zech, Chemical Abstracts, 46 (1952), 8672), lead(II) oxide, aluminum oxide, silver nitrate or basic ion exchangers has been described.

The cleaving agents can be employed in solution or neat, in some instances in powdered form, for example powdered potassium hydroxide.

The cyclization is carried out in inert solvents. Suitable solvents are open-chain or cyclic ethers, for example diethyl ether or dioxane or aromatic hydrocarbons, for example benzene or toluene.

Process G

Epoxidation of olefins of the formula XVI to give the benzoic esters of the formula Vc according to the invention where the variables $R^1$, $R^2$ and M are each as defined under formula V and A is a group of the formula IV.

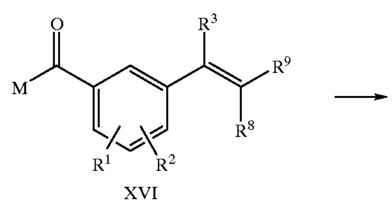

-continued

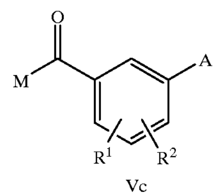

Similarly to processes known from the literature, the epoxidation is frequently carried out using peracids, for example perbenzoic acid, monoperphthalic acid, performic acid, peracetic acid, trifluoroperacetic acid or perpropionic acid (for example R. Criegee, Houben-Weyl, "Methoden der Organischen Chemie", Volume VIII, Oxygen Compounds III, 4. Edition, p. 40 ff., Georg Thieme Verlag, 1965), hydrogen peroxide or tert-butyl hydroperoxide in alkaline solution, preferably in aqueous sodium hydroxide solution, or using dioxiranes, for example dimethyldioxirane or derivatives thereof such as, for example, (trifluoromethyl) methyldioxirane (W. Adam, A. K. Smerz, Bulletin des Sociétés Chimiques Belges 105 (1996), 581).

The peracid epoxidation is carried out in inert solvents such as diethyl ether, chloroform, carbon tetrachloride, ethyl chloride or occasionally in glacial acetic acid, whereas dioxiranes are preferably employed in acetone or derivatives thereof such as, for example, trifluoromethyl methyl ketone.

Per acid, hydrogen peroxide, tert-butyl hydroperoxide or dioxirane are often employed for the reaction in a slight excess; however, an excess of olefin may be advantageous if the oxidizing agent is to be utilized fully.

Process H

Condensation of aldehydes of the formula IX with α-halofatty acid esters XVII or related α-halofatty acid derivatives, for example α-halofatty amides, nitrites or ketones in the presence of alkaline condensing agents by methods known from the literature (for example M. Ballester, Chemical Reviews 55 (1955), 283) to give the benzoic esters of the formula Vc according to the invention in which the variables $R^1$, $R^2$, $R^{10}$ and M are each as defined under formula V and A is a group of the formula IV.

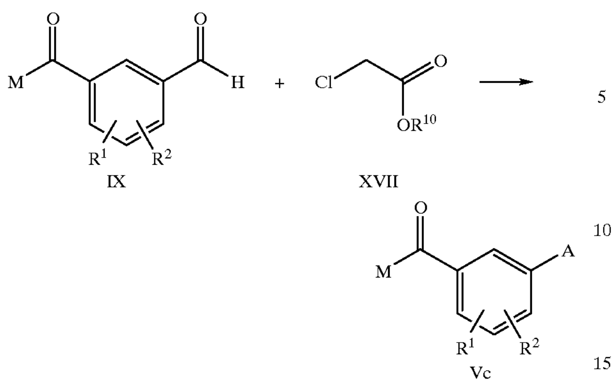

Suitable condensing agents are inorganic or organic catalysts, for example sodium hydride in mineral oil, lithium hydride, tetraethylammonium ethoxide, sodium ethoxide, potassium tert-butoxide or diisopropylmagnesium bromide.

The reaction is carried out in inert solvents, for example in xylene, diethyl ether, methanol, ethanol or tert-butanol.

Emphasis is given to compounds of the formula I according to the invention where A is a group of the formula IIIa or IIIb and $R^4$–$R^7$ are each hydrogen, hydroxyl, mercapto, amino, halogen, $C_1$–$C_6$-alkyl, $C_3$–$C_6$-cycloalkyl, phenyl, —$OR^{10}$, —$S(O)_nR^{10}$, —$OS(O)_nR^{10}$, —$PO(OR^{10})_2$, —$NR^3R^{10}$, —$Si(R^{10})_3$ or —$OCOR^{10}$, where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$, —$Si(R^{10})_3$, —$OCOR^{10}$ may be partially or fully halogenated, and the unsubstituted or partially halogenated alkyl, cycloalkyl and $R^3$ radicals optionally carry one to three of the following groups: hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted, and the unsubstituted or partially halogenated $R^{10}$ radicals optionally carry one to three of the following groups: hydroxyl, mercapto, amino, cyano, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted.

Additionally, emphasis is given to compounds of the formula I according to the invention where A is a group of the formula IIIa or IIIb and $R^4$ and $R^5$ together form a $C_2$–$C_5$-alkylene- or $C_2$–$C_5$-alkenylene chain which may be interrupted once or twice by a nitrogen or an oxygen atom, or form a group =X, where X is an oxygen atom or a group $CR^3R^{10}$, $NR^{10}$ or $NOR^{10}$; and/or $R^6$ and $R^7$ together form a $C_2$–$C_5$-alkylene or $C_2$–$C_5$-alkenylene chain which may be interrupted once or twice by a nitrogen or an oxygen atom, or form a group =X, where X is an oxygen atom or a group $CR^3R^{10}$, $NR^{10}$ or $NOR^{10}$.

Furthermore, emphasis is given to compounds of the formula I according to the invention where A is a group of the formula IIIa or IIIb and $R^5$ and $R^6$ together, if they are attached to adjacent carbon atoms and if $R^4$ and $R^7$ are each hydrogen, form a $C_3$–$C_4$-alkylene or $C_3$–$C_4$-alkenylene chain which may be interrupted by a nitrogen or an oxygen atom.

Moreover, emphasis is to be given to compounds of the formula I according to the invention where A is a group of the formula IVb and $R^8$ and $R^9$ are each hydrogen, nitro, halogen, cyano, $C_1$–$C_6$-alkyl, $C_3$–$C_6$-cycloalkyl, $C_5$–$C_6$-heterocyclyl, —$OR^{10}$, —$SR^{10}$, —$COR^{10}$, —$COOR^{10}$, —$CONR^3R^{10}$, phenyl, phenyl-$C_1$–$C_6$-alkyl and five- or six-membered hetaryl, where the alkyl and cycloalkyl radicals mentioned and $R^3$ and $R^{10}$ of the radicals —$OR^{10}$, —$SR^{10}$, —$COR^{10}$, —$COOR^{10}$, —$CONR^3R^{10}$ may be partially or fully halogenated, and the unsubstituted or partially halogenated alkyl, cycloalkyl and $R^3$ radicals optionally carry one to three of the following groups: hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted, and the unsubstituted or partially halogenated $R^{10}$ radicals optionally carry one to three of the following groups: hydroxyl, mercapto, amino, cyano, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted.

Additionally, emphasis is to be given to compounds of the formula I according to the invention where A is a group of the formula IVb and $R^8$ and $R^9$ together form a $C_2$–$C_5$-alkylene or $C_2$–$C_5$-alkenylene chain which may be interrupted once or twice by a nitrogen or an oxygen atom.

The organic moieties mentioned for the substituents $R^1$–$R^{13}$ or as radicals on phenyl, hetaryl and heterocyclyl rings are collective terms for individual enumerations of the individual group members. All hydrocarbon chains, ie. all alkyl, haloalkyl, cycloalkyl, alkoxyalkyl, alkoxy, haloalkoxy, alkyliminooxy, alkoxyamino, alkylsulfonyl, haloalkylsulfonyl, alkylcarbonyl, haloalkylcarbonyl, alkoxycarbonyl, alkoxyalkoxycarbonyl, alkenyl, cycloalkenyl, alkynyl moieties can be straight-chain or branched. Unless otherwise specified, halogenated substituents preferably have attached to them one to five identical or different halogen atoms, the meaning of halogen being in each case fluorine, chlorine, bromine or iodine.

Examples of other meanings are:

$C_1$–$C_4$-alkyl, and the alkyl moieties of $C_1$–$C_4$-alkylcarbonyl: methyl, ethyl, n-propyl, 1-methylethyl, butyl, 1-methylpropyl, 2-methylpropyl and 1,1-dimethylethyl;

$C_1$–$C_6$-alkyl and the alkyl moieties of $C_1$–$C_6$-alkoxy-$C_1$–$C_6$-alkyl and $C_1$–$C_6$-alkylcarbonyl: $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl and the haloalkyl moieties of $C_1$–$C_6$-haloalkylcarbonyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy and the alkoxy moieties of $C_1$–$C_4$-alkoxyamino, $C_1$–$C_4$-alkoxy-$C_2$–$C_6$-alkoxycarbonyl and $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;

$C_1$–$C_6$-alkoxy and the alkoxy moieties of $C_1$–$C_6$-alkoxy-$C_1$–$C_6$-alkyl, $C_1$–$C_6$-alkoxy-$C_2$–$C_6$-alkyl, $C_1$–$C_4$-alkoxy-$C_2$–$C_6$-alkoxycarbonyl and $C_1$–$C_6$-alkoxycarbonyl: $C_1$–$C_4$-alkoxy as mentioned above, and also pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, eg. fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylsulfonyl ($C_1$–$C_4$-alkyl-S(=O)$_2$—): methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl: $C_1$–$C_4$-alkylsulfonyl as mentioned above, and also pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, ie. fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(choromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$–$C_4$-alkyliminooxy: methyliminooxy, ethyliminooxy, 1-propyliminooxy, 2-propyliminooxy, 1-butyliminooxy and 2-butyliminooxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2- dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl: $C_3$–$C_6$-alkenyl as mentioned above, and also ethenyl;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl: $C_3$–$C_6$-alkynyl as mentioned above, and also ethynyl:

$C_3$–$C_6$-cycloalkyl: cyclopropyl, cyclobutyl, cyclopentyl and cyclohexyl;

$C_4$–$C_6$-cycloalkenyl: cyclobuten-1-yl, cyclobuten-3-yl, cyclopenten-1-yl, cyclopenten-3-yl, cyclopenten-4-yl, cyclohexen-1-yl, cyclohexen-3-yl and cyclohexen-4-yl;

heterocyclyl, and also the heterocyclyl radicals in heterocyclyloxy: three- to seven-membered saturated or partially unsaturated mono- or polycyclic heterocycles which contain one to three hetero atoms selected from a group consisting of oxygen, nitrogen and sulfur, such as oxiranyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, hetaryl, and also the hetaryl radicals in hetaryloxy: aromatic mono- or polycyclic radicals which, besides carbon ring members, may additionally contain one to four nitrogen atoms or one to three nitrogen atoms and one oxygen or one sulfur atom or one oxygen or one sulfur atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4,5-tetrazin-3-yl, and also the corresponding benzo-fuzed derivatives.

All phenyl, hetaryl and heterocyclyl rings are preferably unsubstituted or have attached to them one to three halogen atoms and/or one or two radicals selected from the following group: nitro, cyano, methyl, trifluoromethyl, methoxy, trifluoromethoxy or methoxycarbonyl.

With a view to the use of the compounds of the formula I according to the invention as herbicides, the variables preferably have the following meanings, viz. in each case alone or in combination:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$; especially preferably nitro, halogen, eg. fluorine, chlorine or bromine, $C_1$–$C_6$-haloalkyl, —$OR^5$ or —$SO_2R^7$;

$R^2$ is hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$; especially preferably hydrogen, nitro, halogen, eg. fluorine, chlorine or bromine, $C_1$–$C_6$-alkyl, $C_1$–$C_6$-haloalkyl, —$OR^5$ or —$SO_2R^7$;

$R^4$–$R^7$ are each hydrogen, hydroxyl, mercapto, amino, halogen, $C_1$–$C_4$-alkyl, $C_5$–$C_6$-cycloalkyl, $C_5$–$C_6$-cycloalkenyl, phenyl, —$OR^{10}$, —$S(O)_nR^{10}$, —$OS(O)_nR^{10}$, —$PO(OR^{10})_2$, —$NR^3R^{10}$, —$Si(R^{10})_3$ or —$OCOR^{10}$, where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$, —$Si(R^{10})_3$, —$OCOR^{10}$ may be partially or fully halogenated, and the unsubstituted or partially halogenated alkyl, cycloalkyl and $R^3$ radicals optionally carry one to three of the following groups: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl; especially preferably hydrogen, hydroxyl, mercapto, halogen, for example fluorine, chlorine or bromine, $C_1$–$C_4$-alkyl, —$OSO_2R^{10}$, —$OPO_3R^{10}$, —$Si(CH_3)_3$, and the unsubstituted or partially halogenated $R^{10}$ radicals optionally carry one to three of the following groups: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl; especially preferably hydrogen, hydroxyl, mercapto, halogen, for example fluorine, chlorine or bromine, $C_1$–$C_4$-alkyl, —$Si(CH_3)_3$;

$R^4$ and $R^5$ together preferably form a $C_2$–$C_5$-alkylene or $C_2$–$C_5$-alkenylene chain which may be interrupted once or twice by an oxygen atom, or form a group =X, where X is preferably an oxygen atom or $NR^{10}$; especially preferably, $R^4$ and $R^5$ form a group =X, where =X is preferably an oxygen atom;

$R^6$ and $R^7$ together preferably form a $C_2$–$C_5$-alkylene or $C_2$–$C_5$-alkenylene chain which may be interrupted once or twice by an oxygen atom, or form a group =X, where X is preferably an oxygen atom or $NR^{10}$; especially preferably, $R^6$ and $R^7$ form a group =X, where =X is preferably an oxygen atom;

n is two;

$R^5$ and $R^6$ together, if they are attached to adjacent carbon atoms and $R^4$ and $R^7$ are each hydrogen, preferably form a $C_3$–$C_4$-alkylene or $C_3$–$C_4$-alkenylene chain which may be interrupted by a nitrogen or an oxygen atom;

$R^8$ and $R^9$ are each hydrogen, nitro, halogen, cyano, $C_1$–$C_4$-alkyl, $C_5$–$C_6$-cycloalkyl, $C_5$–$C_6$-cycloalkenyl, $C_5$–$C_6$-heterocyclyl, —$OR^{10}$, —$SR^{10}$, —$COR^{10}$, —$COOR^{10}$, —$CONR^3R^{10}$, phenyl, phenyl-$C_1$–$C_4$-alkyl and five- or 6-membered hetaryl, where the alkyl and cycloalkyl radicals mentioned and $R^3$ and $R^{10}$ of the radicals —$OR^{10}$, —$SR^{10}$, —$COR^{10}$, —$COOR^{10}$, —$CONR^3R^{10}$, may be partially or fully halogenated and/or may carry one to three of the following groups: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;

$R^{10}$ is hydrogen, $C_1$–$C_4$-alkyl, $C_1$–$C_4$-haloalkyl, $C_2$–$C_4$-alkenyl, phenyl or phenyl-$C_1$–$C_4$-alkyl, where the phenyl radical mentioned may be partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;

$R^{11}$ is $C_1$–$C_6$-alkyl or $C_1$–$C_6$-haloalkyl; particularly preferably methyl, ethyl, propyl, isopropyl, butyl or isobutyl;

$R^{12}$ is hydrogen, $C_1$–$C_6$-alkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonylmethyl, or phenylsulfonyl, where the phenyl ring of the two last substituents may be partially or fully halogenated and/or carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$R^{13}$ is hydrogen, $C_1$–$C_6$-alkyl or $C_1$–$C_6$-haloalkyl; particularly preferably hydrogen, methyl, ethyl or trifluoromethyl.

Very particular preference is given to the compounds of the formula Ia, where $R^1$ is attached in position 2 and $R^2$ is attached in position 4 of the phenyl ring.

Ia

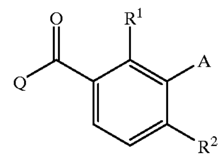

Most particularly preferred are the compounds of the formula Ia where the substituents $R^1$, $R^2$ and Q are each as defined above, A is a group of the formula IIIa or IIIb and $R^4$–$R^7$ are each hydrogen, hydroxyl, amino, halogen, $C_1$–$C_4$-alkyl, $C_5$–$C_6$-cycloalkyl, phenyl, —$OR^{10}$, —$SO_2R^{10}$, —$OSO_2R^{10}$, —$PO(OR^{10})_2$, —$NR^3R^{10}$ or —$OCOR^{10}$, where the alkyl and cycloalkyl radicals mentioned and $R^3$ and $R^{10}$ of the radicals —$OR^{10}$, —$SO_2R^{10}$, —$OSO_2R^{10}$, —$PO(OR^{10})_2$, —$NR^3R^{10}$, —$OCOR^{10}$ may be partially or fully halogenated, and the unsubstituted or partially halogenated alkyl, cycloalkyl and $R^3$ radicals optionally carry one to three of the following groups: hydroxyl, amino, cyano, $R^{10}$, —$OR^{10}$, —$NR^3R^{10}$, —$OCOR^{10}$, —$CO_2R^{10}$, $C_1$–$C_4$-alkylcarbonyl, $C_1$–$C_4$-alkylsulfonyl, phenyl, benzyl, phenoxy and benzyloxy, where the last four radicals mentioned may in turn be substituted, and the unsubstituted or partially halogenated $R^{10}$ radicals optionally carry one to three of the following groups: hydroxyl, amino, cyano, $C_1$–$C_4$-alkylcarbonyl, $C_1$–$C_4$-alkylsulfonyl, phenyl, benzyl, phenoxy and benzyloxy, where the last four radicals mentioned may in turn be substituted.

Additionally, those compounds of the formula Ia according to the invention are most particularly preferred where the substituents $R^1$, $R^2$ and Q are each as defined above, A is a group of the formula IIIa or IIIb and $R^4$ and $R^5$ together form a $C_2$–$C_5$-alkylene or $C_2$–$C_5$-alkenylene chain which may be interrupted once or twice by an oxygen atom, or form a group =X where X is preferably an oxygen atom; and/or $R^6$ and $R^7$ together form a $C_2$–$C_5$-alkylene or $C_2$–$C_5$-alkenylene chain which may be interrupted once or twice by an oxygen atom, or form a group ═X where X is preferably an oxygen atom.

Furthermore, those compounds of the formula Ia according to the invention where the variables $R^1$, $R^2$ and Q are each as defined above, A is a group of the formula IIIa or IIIb and $R^5$ and $R^6$ together, if they are attached to adjacent carbon atoms and if $R^4$ and $R^7$ are each hydrogen, form a $C_3$–$C_4$-alkylene or $C_3$–$C_4$-alkenylene chain which may be interrupted by a nitrogen or an oxygen atom.

Most particular preference is given to the compounds of the formula Ia where the variables $R^1$, $R^2$ and Q are each as defined above, A is a group of the formula IVb and $R^8$ and $R^9$ are each hydrogen, nitro, halogen, cyano, $C_1$–$C_4$-alkyl, $C_5$–$C_6$-cycloalkyl, $C_5$–$C_6$-cycloalkenyl, $C_5$–$C_6$-heterocyclyl, —$OR^{10}$, —$COR^{10}$, —$COOR^{10}$, —$CONR^3R^{10}$, phenyl, phenyl-$C_1$–$C_4$-alkyl and five-oder six-membered hetaryl, where the alkyl and cycloalkyl radicals mentioned and $R^3$ and $R^{10}$ of the radicals —$OR^{10}$, —$COR^{10}$, —$COOR^{10}$, —$CONR^3R^{10}$ may be partially or fully halogenated, and the unsubstituted or partially halogenated alkyl, cycloalkyl and $R^3$ radicals optionally carry one to three of the following groups: hydroxyl, amino, cyano, $R^{10}$, —$OR^{10}$, —$NR^3R^{10}$, —$OCOR^{10}$, —$CO_2R^{10}$, $C_1$–$C_4$-alkylcarbonyl, $C_1$–$C_4$-alkylsulfonyl, phenyl, benzyl, phenoxy and benzyloxy, where the last four radicals may in turn be substituted, and the unsubstituted or partially halogenated $R^{10}$ radicals optionally carry one to three of the following groups: hydroxyl, amino, cyano, $C_1$–$C_4$-alkylcarbonyl, $C_1$–$C_4$-alkylsulfonyl, phenyl, benzyl, phenoxy and benzyloxy, where the last four radicals may in turn be substituted.

In addition, most particular preference is given to those compounds of the formula Ia according to the invention where the variables $R^1$, $R^2$ and Q are each as defined above, A is a group of the formula IVb and $R^8$ and $R^9$ together form a $C_2$–$C_5$-alkylene- or $C_2$–$C_5$-alkenylene chain which may be interrupted once or twice by an oxygen atom.

Very particular preference is given to the compounds Ib of Tables 1 to 144.

TABLE A

| No. | $R^3$ | $R^4$ | $R^5$ | $R^6$ | $R^7$ |
|---|---|---|---|---|---|
| 1 | H | OH | H | H | H |
| 2 | H | OH | —$CH_3$ | H | H |
| 3 | H | OH | —$C_2H_5$ | H | H |
| 4 | H | OH | —$C_3H_7$ | H | H |
| 5 | H | OH | —$C_4H_9$ | H | H |
| 6 | H | OH | —CH═$CH_2$ | H | H |
| 7 | H | OH | —$CH_2$CH═$CH_2$ | H | H |
| 8 | H | OH | —$CH_2$CH═CHPh | H | H |
| 9 | H | OH | —$CH_2$CH═$CHCH_3$ | H | H |
| 10 | H | OH | —C≡CH | H | H |
| 11 | H | OH | —C≡$CCH_3$ | H | H |
| 12 | H | OH | —C≡CPh | H | H |
| 13 | H | OH | Ph | H | H |
| 14 | H | OH | —$CH_2$Ph | H | H |
| 15 | H | OH | Cyclopropyl | H | H |

TABLE A-continued

| No. | $R^3$ | $R^4$ | $R^5$ | $R^6$ | $R^7$ |
|---|---|---|---|---|---|
| 16 | H | OH | Cyclobutyl | H | H |
| 17 | H | OH | Cyclopentyl | H | H |
| 18 | H | OH | Cyclohexyl | H | H |
| 19 | H | OH | OH | H | H |
| 20 | H | OH | —$OCH_3$ | H | H |
| 21 | H | OH | —$OC_2H_5$ | H | H |
| 22 | H | OH | —$OC_3H_7$ | H | H |
| 23 | H | OH | —$OC_4H_9$ | H | H |
| 24 | H | OH | —$OCH_2$CH═$CH_2$ | H | H |
| 25 | H | OH | —OPh | H | H |
| 26 | H | OH | —$OCH_2$Ph | H | H |
| 27 | H | OH | —OCyclopropyl | H | H |
| 28 | H | OH | —OCyclobutyl | H | H |
| 29 | H | OH | —OCyclopentyl | H | H |
| 30 | H | OH | —OCyclohexyl | H | H |
| 31 | H | OH | SH | H | H |
| 32 | H | OH | —$SCH_3$ | H | H |
| 33 | H | OH | —$SC_2H_5$ | H | H |
| 34 | H | OH | —$SC_3H_7$ | H | H |
| 35 | H | OH | —$SC_4H_9$ | H | H |
| 36 | H | OH | —$SCH_2$CH═$CH_2$ | H | H |
| 37 | H | OH | —SPh | H | H |
| 38 | H | OH | —$SCH_2$Ph | H | H |
| 39 | H | OH | —SCyclopropyl | H | H |
| 40 | H | OH | —SCyclobutyl | H | H |
| 41 | H | OH | —SCyclopentyl | H | H |
| 42 | H | OH | —SCyclohexyl | H | H |
| 43 | H | OH | $NH_2$ | H | H |
| 44 | H | OH | —$NHCH_3$ | H | H |
| 45 | H | OH | —$NHC_2H_5$ | H | H |
| 46 | H | OH | —$NHC_3H_7$ | H | H |
| 47 | H | OH | —$NHC_4H_9$ | H | H |
| 48 | H | OH | —$NHCH_2$CH═$CH_2$ | H | H |
| 49 | H | OH | —NHPh | H | H |
| 50 | H | OH | —$NHCH_2$Ph | H | H |
| 51 | H | OH | —NHCyclopropyl | H | H |
| 52 | H | OH | —NHCyclobutyl | H | H |
| 53 | H | OH | —NHCyclopentyl | H | H |
| 54 | H | OH | —NHcyclohexyl | H | H |
| 55 | H | OH | —$N(CH_3)_2$ | H | H |
| 56 | H | OH | —$N(CH_3)(C_2H_5)$ | H | H |
| 57 | H | OH | —$N(C_2H_5)_2$ | H | H |
| 58 | H | OH | —$N(CH_3)(C_3H_7)$ | H | H |
| 59 | H | OH | —$N(CH_3)C_4H_9$ | H | H |
| 60 | H | OH | —$N(CH_3)(CH_2CH$═$CH_2)$ | H | H |
| 61 | H | OH | —$N(CH_3)$Ph | H | H |
| 62 | H | OH | —$N(C_2H_5)$Ph | H | H |
| 63 | H | OH | —$N(Ph)_2$ | H | H |
| 64 | H | OH | —$N(C_2H_5)(CH_2Ph)$ | H | H |
| 65 | H | OH | —$N(CH_2Ph)_2$ | H | H |
| 66 | H | OH | —$N(CH_3)(CH_2Ph)$ | H | H |
| 67 | H | OH | —$N(CH_3)$Cyclopropyl | H | H |
| 68 | H | OH | —$N(CH_3)$Cyclobutyl | H | H |
| 69 | H | OH | —$N(CH_3)$Cyclopentyl | H | H |
| 70 | H | OH | —$N(CH_3)$Cyclohexyl | H | H |
| 71 | H | —$OSi(CH_3)_3$ | H | H | H |
| 72 | H | —$OSi(CH_3)_3$ | —$CH_3$ | H | H |
| 73 | H | —$OSi(CH_3)_3$ | —$C_3H_5$ | H | H |
| 74 | H | —$OSi(CH_3)_3$ | —$C_3H_7$ | H | H |
| 75 | H | —$OSi(CH_3)_3$ | —$C_4H_9$ | H | H |
| 76 | H | —$OSi(CH_3)_3$ | —CH═$CH_2$ | H | H |
| 77 | H | —$OSi(CH_3)_3$ | —$CH_2$CH═$CH_2$ | H | H |
| 78 | H | —$OSi(CH_3)_3$ | —$CH_2$CH═CHPh | H | H |
| 79 | H | —$OSi(CH_3)_3$ | —$CH_2$CH═$CHCH_3$ | H | H |
| 80 | H | —$OSi(CH_3)_3$ | —C≡CH | H | H |
| 81 | H | —$OSi(CH_3)_3$ | —C≡$CCH_3$ | H | H |
| 82 | H | —$OSi(CH_3)_3$ | —C≡CPh | H | H |
| 83 | H | —$OSi(CH_3)_3$ | Ph | H | H |
| 84 | H | —$OSi(CH_3)_3$ | —$CH_2$Ph | H | H |
| 85 | H | —$OSi(CH_3)_3$ | Cyclopropyl | H | H |
| 86 | H | —$OSi(CH_3)_3$ | Cyclobutyl | H | H |
| 87 | H | —$OSi(CH_3)_3$ | Cyclopentyl | H | H |
| 88 | H | —$OSi(CH_3)_3$ | Cyclohexyl | H | H |
| 89 | H | —$OSi(CH_3)_3$ | OH | H | H |
| 90 | H | —$OSi(CH_3)_3$ | —$OCH_3$ | H | H |
| 91 | H | —$OSi(CH_3)_3$ | —$OC_2H_5$ | H | H |
| 92 | H | —$OSi(CH_3)_3$ | —$OC_2H_7$ | H | H |

TABLE A-continued

| No. | R$^3$ | R$^4$ | R$^5$ | R$^6$ | R$^7$ |
|---|---|---|---|---|---|
| 93 | H | —OSi(CH$_3$)$_3$ | —OC$_4$H$_9$ | H | H |
| 94 | H | —OSi(CH$_3$)$_3$ | —OCH$_2$CH=CH$_2$ | H | H |
| 95 | H | —OSi(CH$_3$)$_3$ | —OPh | H | H |
| 96 | H | —OSi(CH$_3$)$_3$ | —OCH$_2$Ph | H | H |
| 97 | H | —OSi(CH$_3$)$_3$ | —OCyclopropyl | H | H |
| 98 | H | —OSi(CH$_3$)$_3$ | —OCyclobutyl | H | H |
| 99 | H | —OSi(CH$_3$)$_3$ | —OCyclopentyl | H | H |
| 100 | H | —OSi(CH$_3$)$_3$ | —OCyclohexyl | H | H |
| 101 | H | —OSi(CH$_3$)$_3$ | SH | H | H |
| 102 | H | —OSi(CH$_3$)$_3$ | —SCH$_3$ | H | H |
| 103 | H | —OSi(CH$_3$)$_3$ | —SC$_2$H$_5$ | H | H |
| 104 | H | —OSi(CH$_3$)$_3$ | —SC$_3$H$_7$ | H | H |
| 105 | H | —OSi(CH$_3$)$_3$ | —SC$_4$H$_9$ | H | H |
| 106 | H | —OSi(CH$_3$)$_3$ | —SCH$_2$CH=CH$_2$ | H | H |
| 107 | H | —OSi(CH$_3$)$_3$ | —SPh | H | H |
| 108 | H | —OSi(CH$_3$)$_3$ | —SCH$_2$Ph | H | H |
| 109 | H | —OSi(CH$_3$)$_3$ | —SCyclopropyl | H | H |
| 110 | H | —OSi(CH$_3$)$_3$ | —SCyclobutyl | H | H |
| 111 | H | —OSi(CH$_3$)$_3$ | —SCyclopentyl | H | H |
| 112 | H | —OSi(CH$_3$)$_3$ | —SCyclohexyl | H | H |
| 113 | H | —OSi(CH$_3$)$_3$ | NH$_2$ | H | H |
| 114 | H | —OSi(CH$_3$)$_3$ | —NHCH$_3$ | H | H |
| 115 | H | —OSi(CH$_3$)$_3$ | —NHC$_2$H$_5$ | H | H |
| 116 | H | —OSi(CH$_3$)$_3$ | —NHC$_3$H$_7$ | H | H |
| 117 | H | —OSi(CH$_3$)$_3$ | —NHC$_4$H$_9$ | H | H |
| 118 | H | —OSi(CH$_3$)$_3$ | —NHCH$_2$CH=CH$_2$ | H | H |
| 119 | H | —OSi(CH$_3$)$_3$ | —NHPh | H | H |
| 120 | H | —OSi(CH$_3$)$_3$ | —NHCH$_2$Ph | H | H |
| 121 | H | —OSi(CH$_3$)$_3$ | —NHCyclopropyl | H | H |
| 122 | H | —OSi(CH$_3$)$_3$ | —NHCyclobutyl | H | H |
| 123 | H | —OSi(CH$_3$)$_3$ | —NHCyclopentyl | H | H |
| 124 | H | —OSi(CH$_3$)$_3$ | —NHCyclohexyl | H | H |
| 125 | H | —OSi(CH$_3$)$_3$ | —N(CH$_3$)$_2$ | H | H |
| 126 | H | —OSi(CH$_3$)$_3$ | —N(CH$_3$)(C$_2$H$_5$) | H | H |
| 127 | H | —OSi(CH$_3$)$_3$ | —N(C$_2$H$_5$)$_2$ | H | H |
| 128 | H | —OSi(CH$_3$)$_3$ | —N(CH$_3$)(C$_3$H$_7$) | H | H |
| 129 | H | —OSi(CH$_3$)$_3$ | —N(CH$_3$)C$_4$H$_9$ | H | H |
| 130 | H | —OSi(CH$_3$)$_3$ | —N(CH$_3$)(CH$_2$CH=CH$_2$) | H | H |
| 131 | H | —OSi(CH$_3$)$_3$ | —N(CH$_3$)Ph | H | H |
| 132 | H | —OSi(CH$_3$)$_3$ | —N(C$_2$H$_5$)Ph | H | H |
| 133 | H | —OSi(CH$_3$)$_3$ | —N(Ph)$_2$ | H | H |
| 134 | H | —OSi(CH$_3$)$_3$ | —N(C$_2$H$_5$)(CH$_2$Ph) | H | H |
| 135 | H | —OSi(CH$_3$)$_3$ | —N(CH$_2$Ph)$_2$ | H | H |
| 136 | H | —OSi(CH$_3$)$_3$ | —N(CH$_3$)(CH$_2$Ph) | H | H |
| 137 | H | —OSi(CH$_3$)$_3$ | —N(CH$_3$)Cyclopropyl | H | H |
| 138 | H | —OSi(CH$_3$)$_3$ | —N(CH$_3$)Cyclobutyl | H | H |
| 139 | H | —OSi(CH$_3$)$_3$ | —N(CH$_3$)Cyclopentyl | H | H |
| 140 | H | —OSi(CH$_3$)$_3$ | —N(CH$_3$)Cyclohexyl | H | H |
| 141 | H | —OCH$_3$ | H | H | H |
| 142 | H | —OCH$_3$ | —CH$_3$ | H | H |
| 143 | H | —OCH$_3$ | —C$_2$H$_5$ | H | H |
| 144 | H | —OCH$_3$ | —C$_3$H$_7$ | H | H |
| 145 | H | —OCH$_3$ | —C$_4$H$_9$ | H | H |
| 146 | H | —OCH$_3$ | —CH=CH$_2$ | H | H |
| 147 | H | —OCH$_3$ | —CH$_2$CH=CH$_2$ | H | H |
| 148 | H | —OCH$_3$ | —CH$_2$CH=CHPh | H | H |
| 149 | H | —OCH$_3$ | —CH$_2$CH=CHCH$_3$ | H | H |
| 150 | H | —OCH$_3$ | —C≡CH | H | H |
| 151 | H | —OCH$_3$ | —C≡CCH$_3$ | H | H |
| 152 | H | —OCH$_3$ | —C≡CPh | H | H |
| 153 | H | —OCH$_3$ | Ph | H | H |
| 154 | H | —OCH$_3$ | —CH$_2$Ph | H | H |
| 155 | H | —OCH$_3$ | Cyclopropyl | H | H |
| 156 | H | —OCH$_3$ | Cyclobutyl | H | H |
| 157 | H | —OCH$_3$ | Cyclopentyl | H | H |
| 158 | H | —OCH$_3$ | Cyclohexyl | H | H |
| 159 | H | —OCH$_3$ | OH | H | H |
| 160 | H | —OCH$_3$ | —OCH$_3$ | H | H |
| 161 | H | —OCH$_3$ | —OC$_2$H$_5$ | H | H |
| 162 | H | —OCH$_3$ | —OC$_3$H$_7$ | H | H |
| 163 | H | —OCH$_3$ | —OC$_4$H$_9$ | H | H |
| 164 | H | —OCH$_3$ | —OCH$_2$CH=CH$_2$ | H | H |
| 165 | H | —OCH$_3$ | —OPh | H | H |
| 166 | H | —OCH$_3$ | —OCH$_2$Ph | H | H |
| 167 | H | —OCH$_3$ | —OCyclopropyl | H | H |
| 168 | H | —OCH$_3$ | —OCyclobutyl | H | H |
| 169 | H | —OCH$_3$ | —OCyclopentyl | H | H |

TABLE A-continued

| No. | R$^3$ | R$^4$ | R$^5$ | R$^6$ | R$^7$ |
|---|---|---|---|---|---|
| 170 | H | —OCH$_3$ | —OCyclohexyl | H | H |
| 171 | H | —OCH$_3$ | SH | H | H |
| 172 | H | —OCH$_3$ | —SCH$_3$ | H | H |
| 173 | H | —OCH$_3$ | —SC$_2$H$_5$ | H | H |
| 174 | H | —OCH$_3$ | —SC$_3$H$_7$ | H | H |
| 175 | H | —OCH$_3$ | —SC$_4$H$_9$ | H | H |
| 176 | H | —OCH$_3$ | —SCH$_2$CH=CH$_2$ | H | H |
| 177 | H | —OCH$_3$ | —SPh | H | H |
| 178 | H | —OCH$_3$ | —SCH$_2$Ph | H | H |
| 179 | H | —OCH$_3$ | —SCyclopropyl | H | H |
| 180 | H | —OCH$_3$ | —SCyclobutyl | H | H |
| 181 | H | —OCH$_3$ | —SCyclopentyl | H | H |
| 182 | H | —OCH$_3$ | —SCyclohexyl | H | H |
| 183 | H | —OCH$_3$ | NH$_2$ | H | H |
| 184 | H | —OCH$_3$ | —NHCH$_3$ | H | H |
| 185 | H | —OCH$_3$ | —NHC$_2$H$_5$ | H | H |
| 186 | H | —OCH$_3$ | —NHC$_3$H$_7$ | H | H |
| 187 | H | —OCH$_3$ | —NHC$_4$H$_9$ | H | H |
| 188 | H | —OCH$_3$ | —NHCH$_2$CH=CH$_2$ | H | H |
| 189 | H | —OCH$_3$ | —NHPh | H | H |
| 190 | H | —OCH$_3$ | —NHCH$_2$Ph | H | H |
| 191 | H | —OCH$_3$ | —NHCyclopropyl | H | H |
| 192 | H | —OCH$_3$ | —NHCyclobutyl | H | H |
| 193 | H | —OCH$_3$ | —NHCyclopentyl | H | H |
| 194 | H | —OCH$_3$ | —NHCyclohexyl | H | H |
| 195 | H | —OCH$_3$ | —N(CH$_3$)$_2$ | H | H |
| 196 | H | —OCH$_3$ | —N(CH$_3$)(C$_2$H$_5$) | H | H |
| 197 | H | —OCH$_3$ | —N(C$_2$H$_5$)$_2$ | H | H |
| 198 | H | —OCH$_3$ | —N(CH$_3$)(C$_3$H$_7$) | H | H |
| 199 | H | —OCH$_3$ | —N(CH$_3$)C$_4$H$_9$ | H | H |
| 200 | H | —OCH$_3$ | —N(CH$_3$)(CH$_2$CH=CH$_2$) | H | H |
| 201 | H | —OCH$_3$ | —N(CH$_3$)Ph | H | H |
| 202 | H | —OCH$_3$ | —N(C$_2$H$_5$)Ph | H | H |
| 203 | H | —OCH$_3$ | —N(Ph)$_2$ | H | H |
| 204 | H | —OCH$_3$ | —N(C$_2$H$_5$)(CH$_2$Ph) | H | H |
| 205 | H | —OCH$_3$ | —N(CH$_2$Ph)$_2$ | H | H |
| 206 | H | —OCH$_3$ | —N(CH$_3$)(CH$_2$Ph) | H | H |
| 207 | H | —OCH$_3$ | —N(CH$_3$)Cyclopropyl | H | H |
| 208 | H | —OCH$_3$ | —N(CH$_3$)Cyclobutyl | H | H |
| 209 | H | —OCH$_3$ | —N(CH$_3$)Cyclopentyl | H | H |
| 210 | H | —OCH$_3$ | —N(CH$_3$)Cyclohexyl | H | H |
| 211 | H | —OSO$_2$CH$_3$ | H | H | H |
| 212 | H | —OSO$_2$CH$_3$ | —CH$_3$ | H | H |
| 213 | H | —OSO$_2$CH$_3$ | —C$_2$H$_5$ | H | H |
| 214 | H | —OSO$_2$CH$_3$ | —C$_3$H$_7$ | H | H |
| 215 | H | —OSO$_2$CH$_3$ | —C$_4$H$_9$ | H | H |
| 218 | H | —OSO$_2$CH$_3$ | —CH=CH$_2$ | H | H |
| 217 | H | —OSO$_2$CH$_3$ | —CH$_2$CH=CH$_2$ | H | H |
| 218 | H | —OSO$_2$CH$_3$ | —CH$_2$CH=CHPh | H | H |
| 219 | H | —OSO$_2$CH$_3$ | —CH$_2$CH=CHCH$_3$ | H | H |
| 220 | H | —OSO$_2$CH$_3$ | —C≡CH | H | H |
| 221 | H | —OSO$_2$CH$_3$ | —C≡CCH$_3$ | H | H |
| 222 | H | —OSO$_2$CH$_3$ | —C≡CPh | H | H |
| 223 | H | —OSO$_2$CH$_3$ | Ph | H | H |
| 224 | H | —OSO$_2$CH$_3$ | —CH$_2$Ph | H | H |
| 225 | H | —OSO$_2$CH$_3$ | Cyclopropyl | H | H |
| 226 | H | —OSO$_2$CH$_3$ | Cyclobutyl | H | H |
| 227 | H | —OSO$_2$CH$_3$ | Cyclopentyl | H | H |
| 228 | H | —OSO$_2$CH$_3$ | Cyclohexyl | H | H |
| 229 | H | —OSO$_2$CH$_3$ | OH | H | H |
| 230 | H | —OSO$_2$CH$_3$ | —OCH$_3$ | H | H |
| 231 | H | —OSO$_2$CH$_3$ | —OC$_2$H$_5$ | H | H |
| 232 | H | —OSO$_2$CH$_3$ | —OC$_3$H$_7$ | H | H |
| 233 | H | —OSO$_2$CH$_3$ | —OC$_4$H$_9$ | H | H |
| 234 | H | —OSO$_2$CH$_3$ | —OCH$_2$CH=CH$_2$ | H | H |
| 235 | H | —OSO$_2$CH$_3$ | —OPh | H | H |
| 236 | H | —OSO$_2$CH$_3$ | —OCH$_2$Ph | H | H |
| 237 | H | —OSO$_2$CH$_3$ | —OCyclopropyl | H | H |
| 236 | H | —OSO$_2$CH$_3$ | —OCyclobutyl | H | H |
| 239 | H | —OSO$_2$CH$_3$ | —OCyclopentyl | H | H |
| 240 | H | —OSO$_2$CH$_3$ | —OCyclohexyl | H | H |
| 241 | H | —OSO$_2$CH$_3$ | SH | H | H |
| 242 | H | —OSO$_2$CH$_3$ | —SCH$_3$ | H | H |
| 243 | H | —OSO$_2$CH$_3$ | —SC$_2$H$_5$ | H | H |
| 244 | H | —OSO$_2$CH$_3$ | —SC$_3$H$_7$ | H | H |
| 245 | H | —OSO$_2$CH$_3$ | —SC$_4$H$_9$ | H | H |
| 246 | H | —OSO$_2$CH$_3$ | —SCH$_2$CH=CH$_2$ | H | H |

TABLE A-continued

| No. | $R^3$ | $R^4$ | $R^5$ | $R^6$ | $R^7$ |
|---|---|---|---|---|---|
| 247 | H | —$OSO_2CH_3$ | —SPh | H | H |
| 248 | H | —$OSO_2CH_3$ | —$SCH_2Ph$ | H | H |
| 249 | H | —$OSO_2CH_3$ | —SCyclopropyl | H | H |
| 250 | H | —$OSO_2CH_3$ | —SCyclobutyl | H | H |
| 251 | H | —$OSO_2CH_3$ | —SCyclopentyl | H | H |
| 252 | H | —$OSO_2CH_3$ | —SCyclohexyl | H | H |
| 253 | H | —$OSO_2CH_3$ | $NH_2$ | H | H |
| 254 | H | —$OSO_2CH_3$ | —$NHCH_3$ | H | H |
| 255 | H | —$OSO_2CH_3$ | —$NHC_2H_5$ | H | H |
| 256 | H | —$OSO_2CH_3$ | —$NHC_3H_7$ | H | H |
| 257 | H | —$OSO_2CH_3$ | —$NHC_4H_9$ | H | H |
| 256 | H | —$OSO_2CH_3$ | —$NHCH_2CH=CH_2$ | H | H |
| 259 | H | —$OSO_2CH_3$ | —NHPh | H | H |
| 260 | H | —$OSO_2CH_3$ | —$NHCH_2Ph$ | H | H |
| 261 | H | —$OSO_2CH_3$ | —NHCyclopropyl | H | H |
| 262 | H | —$OSO_2CH_3$ | —NHCyclobutyl | H | H |
| 263 | H | —$OSO_2CH_3$ | —NHCyclopentyl | H | H |
| 264 | H | —$OSO_2CH_3$ | —NHCyclohexyl | H | H |
| 265 | H | —$OSO_2CH_3$ | —$N(CH_3)_2$ | H | H |
| 266 | H | —$OSO_2CH_3$ | —$N(CH_3)(C_2H_5)$ | H | H |
| 267 | H | —$OSO_2CH_3$ | —$N(C_2H_5)_2$ | H | H |
| 268 | H | —$OSO_2CH_3$ | —$N(CH_3)(C_3H_7)$ | H | H |
| 269 | H | —$OSO_2CH_3$ | —$N(CH_3)C_4H_9$ | H | H |
| 270 | H | —$OSO_2CH_3$ | —$N(CH_3)(CH_2CH=CH_2)$ | H | H |
| 271 | H | —$OSO_2CH_3$ | —$N(CH_3)Ph$ | H | H |
| 272 | H | —$OSO_2CH_3$ | —$N(C_2H_5)Ph$ | H | H |
| 273 | H | —$OSO_2CH_3$ | —$N(Ph)_2$ | H | H |
| 274 | H | —$OSO_2CH_3$ | —$N(C_2H_5)(CH_2Ph)$ | H | H |
| 275 | H | —$OSO_2CH_3$ | —$N(CH_2Ph)_2$ | H | H |
| 276 | H | —$OSO_2CH_3$ | —$N(CH_3)(CH_2Ph)$ | H | H |
| 277 | H | —$OSO_2CH_3$ | —$N(CH_3)$Cyclopropyl | H | H |
| 278 | H | —$OSO_2CH_3$ | —$N(CH_3)$Cyclobutyl | H | H |
| 279 | H | —$OSO_2CH_3$ | —$N(CH_3)$Cyclopentyl | H | H |
| 280 | H | —$OSO_2CH_3$ | —$N(CH_3)$Cyclohexyl | H | H |
| 281 | —$CH_3$ | OH | H | H | H |
| 282 | —$CH_3$ | OH | —$CH_3$ | H | H |
| 283 | —$CH_3$ | OH | —$C_2H_5$ | H | H |
| 284 | —$CH_3$ | OH | —$C_3H_7$ | H | H |
| 285 | —$CH_3$ | OH | —$C_4H_9$ | H | H |
| 286 | —$CH_3$ | OH | —$CH=CH_2$ | H | H |
| 287 | —$CH_3$ | OH | —$CH_2CH=CH_2$ | H | H |
| 288 | —$CH_3$ | OH | —$CH_2CH=CHPh$ | H | H |
| 289 | —$CH_3$ | OH | —$CH_2CH=CHCH_3$ | H | H |
| 290 | —$CH_3$ | OH | —$C\equiv CH$ | H | H |
| 291 | —$CH_3$ | OH | —$C\equiv CCH_3$ | H | H |
| 292 | —$CH_3$ | OH | —$C\equiv CPh$ | H | H |
| 293 | —$CH_3$ | OH | Ph | H | H |
| 294 | —$CH_3$ | OH | —$CH_2Ph$ | H | H |
| 295 | —$CH_3$ | OH | Cyclopropyl | H | H |
| 296 | —$CH_3$ | OH | Cyclobutyl | H | H |
| 297 | —$CH_3$ | OH | Cyclopentyl | H | H |
| 298 | —$CH_3$ | OH | Cyclohexyl | H | H |
| 299 | —$CH_3$ | OH | OH | H | H |
| 300 | —$CH_3$ | OH | —$OCH_3$ | H | H |
| 301 | —$CH_3$ | OH | —$OC_2H_5$ | H | H |
| 302 | —$CH_3$ | OH | —$OC_3H_7$ | H | H |
| 303 | —$CH_3$ | OH | —$OC_4H_9$ | H | H |
| 304 | —$CH_3$ | OH | —$OCH_2CH=CH_2$ | H | H |
| 305 | —$CH_3$ | OH | —OPh | H | H |
| 306 | —$CH_3$ | OH | —$OCH_2Ph$ | H | H |
| 307 | —$CH_3$ | OH | —OCyclopropyl | H | H |
| 308 | —$CH_3$ | OH | —OCyclobutyl | H | H |
| 309 | —$CH_3$ | OH | —OCyclopentyl | H | H |
| 310 | —$CH_3$ | OH | —OCyclohexyl | H | H |
| 311 | —$CH_3$ | OH | SH | H | H |
| 312 | —$CH_3$ | OH | —$SCH_3$ | H | H |
| 313 | —$CH_3$ | OH | —$SC_2H_5$ | H | H |
| 314 | —$CH_3$ | OH | —$SC_3H_7$ | H | H |
| 315 | —$CH_3$ | OH | —$SC_4H_9$ | H | H |
| 316 | —$CH_3$ | OH | —$SCH_2CH=CH_2$ | H | H |
| 317 | —$CH_3$ | OH | —SPh | H | H |
| 318 | —$CH_3$ | OH | —$SCH_2Ph$ | H | H |
| 319 | —$CH_3$ | OH | —SCyclopropyl | H | H |
| 320 | —$CH_3$ | OH | —SCyclobutyl | H | H |
| 321 | —$CH_3$ | OH | —SCyclopentyl | H | H |
| 322 | —$CH_3$ | OH | —SCyclohexyl | H | H |
| 323 | —$CH_3$ | OH | $NH_2$ | H | H |

TABLE A-continued

| No. | $R^3$ | $R^4$ | $R^5$ | $R^6$ | $R^7$ |
|---|---|---|---|---|---|
| 324 | —$CH_3$ | OH | —$NHCH_3$ | H | H |
| 325 | —$CH_3$ | OH | —$NHC_2H_5$ | H | H |
| 326 | —$CH_3$ | OH | —$NHC_3H_7$ | H | H |
| 327 | —$CH_3$ | OH | —$NHC_4H_9$ | H | H |
| 328 | —$CH_3$ | OH | —$NHCH_2CH=CH_2$ | H | H |
| 329 | —$CH_3$ | OH | —NHPh | H | H |
| 330 | —$CH_3$ | OH | —$NHCH_2Ph$ | H | H |
| 331 | —$CH_3$ | OH | —NHCyclopropyl | H | H |
| 332 | —$CH_3$ | OH | —NHCyclobutyl | H | H |
| 333 | —$CH_3$ | OH | —NHCyclopentyl | H | H |
| 334 | —$CH_3$ | OH | —NHCyclohexyl | H | H |
| 335 | —$CH_3$ | OH | —$N(CH_3)_2$ | H | H |
| 336 | —$CH_3$ | OH | —$N(CH_3)(C_2H_5)$ | H | H |
| 337 | —$CH_3$ | OH | —$N(C_2H_5)_2$ | H | H |
| 338 | —$CH_3$ | OH | —$N(CH_3)(C_3H_7)$ | H | H |
| 339 | —$CH_3$ | OH | —$N(CH_3)C_4H_9$ | H | H |
| 340 | —$CH_3$ | OH | —$N(CH_3)(CH_2CH=CH_2)$ | H | H |
| 341 | —$CH_3$ | OH | —$N(CH_3)Ph$ | H | H |
| 342 | —$CH_3$ | OH | —$N(C_2H_5)Ph$ | H | H |
| 343 | —$CH_3$ | OH | —$N(Ph)_2$ | H | H |
| 344 | —$CH_3$ | OH | —$N(C_2H_5)(CH_2Ph)$ | H | H |
| 345 | —$CH_3$ | OH | —$N(CH_2Ph)_2$ | H | H |
| 346 | —$CH_3$ | OH | —$N(CH_3)(CH_2Ph)$ | H | H |
| 347 | —$CH_3$ | OH | —$N(CH_3)$Cyclopropyl | H | H |
| 348 | —$CH_3$ | OH | —$N(CH_3)$Cyclobutyl | H | H |
| 349 | —$CH_3$ | OH | —$N(CH_3)$Cyclopentyl | H | H |
| 350 | —$CH_3$ | OH | —$N(CH_3)$Cyclohexyl | H | H |
| 351 | H | OH | H | —$CH_3$ | H |
| 352 | H | OH | —$CH_3$ | —$CH_3$ | H |
| 353 | H | OH | —$C_2H_5$ | —$CH_3$ | H |
| 354 | H | OH | —$C_3H_7$ | —$CH_3$ | H |
| 355 | H | OH | —$C_4H_9$ | —$CH_3$ | H |
| 356 | H | OH | —$CH=CH_2$ | —$CH_3$ | H |
| 357 | H | OH | —$CH_2CH=CH_2$ | —$CH_3$ | H |
| 358 | H | OH | —$CH_2CH=CHPh$ | —$CH_3$ | H |
| 359 | H | OH | —$CH_2CH=CHCH_3$ | —$CH_3$ | H |
| 360 | H | OH | —$C\equiv CH$ | —$CH_3$ | H |
| 361 | H | OH | —$C\equiv CCH_3$ | —$CH_3$ | H |
| 362 | H | OH | —$C\equiv CPh$ | —$CH_3$ | H |
| 363 | H | OH | Ph | —$CH_3$ | H |
| 364 | H | OH | —$CH_2Ph$ | —$CH_3$ | H |
| 365 | H | OH | Cyclopropyl | —$CH_3$ | H |
| 366 | H | OH | Cyclobutyl | —$CH_3$ | H |
| 367 | H | OH | Cyclopentyl | —$CH_3$ | H |
| 368 | H | OH | Cyclohexyl | —$CH_3$ | H |
| 369 | H | OH | OH | —$CH_3$ | H |
| 370 | H | OH | —$OCH_3$ | —$CH_3$ | H |
| 371 | H | OH | —$OC_2H_5$ | —$CH_3$ | H |
| 372 | H | OH | —$OC_3H_7$ | —$CH_3$ | H |
| 373 | H | OH | —$OC_4H_9$ | —$CH_3$ | H |
| 374 | H | OH | —$OCH_2CH=CH_2$ | —$CH_3$ | H |
| 375 | H | OH | —OPh | —$CH_3$ | H |
| 376 | H | OH | —$OCH_2Ph$ | —$CH_3$ | H |
| 377 | H | OH | —OCyclopropyl | —$CH_3$ | H |
| 378 | H | OH | —OCyclobutyl | —$CH_3$ | H |
| 379 | H | OH | —OCyclopentyl | —$CH_3$ | H |
| 380 | H | OH | —OCyclohexyl | —$CH_3$ | H |
| 381 | H | OH | SH | —$CH_3$ | H |
| 382 | H | OH | —$SCH_3$ | —$CH_3$ | H |
| 383 | H | OH | —$SC_2H_5$ | —$CH_3$ | H |
| 384 | H | OH | —$SC_3H_7$ | —$CH_3$ | H |
| 385 | H | OH | —$SC_4H_9$ | —$CH_3$ | H |
| 386 | H | OH | —$SCH_2CH=CH_2$ | —$CH_3$ | H |
| 387 | H | OH | —SPh | —$CH_3$ | H |
| 388 | H | OH | —$SCH_2Ph$ | —$CH_3$ | H |
| 389 | H | OH | —SCyclopropyl | —$CH_3$ | H |
| 390 | H | OH | —SCyclobutyl | —$CH_3$ | H |
| 391 | H | OH | —SCyclopentyl | —$CH_3$ | H |
| 392 | H | OH | —SCyclohexyl | —$CH_3$ | H |
| 393 | H | OH | $NH_2$ | —$CH_3$ | H |
| 394 | H | OH | —$NHCH_3$ | —$CH_3$ | H |
| 395 | H | OH | —$NHC_2H_5$ | —$CH_3$ | H |
| 396 | H | OH | —$NHC_3H_7$ | —$CH_3$ | H |
| 397 | H | OH | —$NHC_4H_9$ | —$CH_3$ | H |
| 398 | H | OH | —$NHCH_2CH=CH_2$ | —$CH_3$ | H |
| 399 | H | OH | —NHPh | —$CH_3$ | H |
| 400 | H | OH | —$NHCH_2Ph$ | —$CH_3$ | H |

TABLE A-continued

| No. | $R^3$ | $R^4$ | $R^5$ | $R^6$ | $R^7$ |
|---|---|---|---|---|---|
| 401 | H | OH | —NHCyclopropyl | —$CH_3$ | H |
| 402 | H | OH | —NHCyclobutyl | —$CH_3$ | H |
| 403 | H | OH | —NHCyclopentyl | —$CH_3$ | H |
| 404 | H | OH | —NHCyclohexyl | —$CH_3$ | H |
| 405 | H | OH | —$N(CH_3)_2$ | —$CH_3$ | H |
| 406 | H | OH | —$N(CH_3)(C_2H_5)$ | —$CH_3$ | H |
| 407 | H | OH | —$N(C_2H_5)_2$ | —$CH_3$ | H |
| 408 | H | OH | —$N(CH_3)(C_3H_7)$ | —$CH_3$ | H |
| 409 | H | OH | —$N(CH_3)C_4H_9$ | —$CH_3$ | H |
| 410 | H | OH | —$N(CH_3)(CH_2CH{=}CH_2)$ | —$CH_3$ | H |
| 411 | H | OH | —$N(CH_3)Ph$ | —$CH_3$ | H |
| 412 | H | CH | —$N(C_2H_5)Ph$ | —$CH_3$ | H |
| 413 | H | OH | —$N(Ph)_2$ | —$CH_3$ | H |
| 414 | H | OH | —$N(C_2H_5)(CH_2Ph)$ | —$CH_3$ | H |
| 415 | H | OH | —$N(CH_2Ph)_2$ | —$CH_3$ | H |
| 416 | H | OH | —$N(CH_3)(CH_2Ph)$ | —$CH_3$ | H |
| 417 | H | OH | —$N(CH_3)$Cyclopropyl | —$CH_3$ | H |
| 41B | H | OH | —$N(CH_3)$Cyclobutyl | —$CH_3$ | H |
| 419 | H | OH | —$N(CH_3)$Cyclopentyl | —$CH_3$ | H |
| 420 | H | OH | —$N(CH_3)$Cyclohexyl | —$CH_3$ | H |
| 421 | H | OH | H | Ph | H |
| 422 | H | OH | —$CH_3$ | Ph | H |
| 423 | H | OH | —$C_2H_5$ | Ph | H |
| 424 | H | OH | —$C_3H_7$ | Ph | H |
| 425 | H | OH | —$C_4H_9$ | Ph | H |
| 426 | H | OH | —$CH{=}CH_2$ | Ph | H |
| 427 | H | OH | —$CH_2CH{=}CH_2$ | Ph | H |
| 428 | H | OH | —$CH_2CH{=}CHPh$ | Ph | H |
| 429 | H | OH | —$CH_2CH{=}CHCH_3$ | Ph | H |
| 430 | H | OH | —$C{\equiv}CH$ | Ph | H |
| 431 | H | OH | —$C{\equiv}CCH_3$ | Ph | H |
| 432 | H | OH | —$C{\equiv}CPh$ | Ph | H |
| 433 | H | OH | Ph | Ph | H |
| 434 | H | OH | —$CH_2Ph$ | Ph | H |
| 435 | H | OH | Cyclopropyl | Ph | H |
| 436 | H | OH | Cyclobutyl | Ph | H |
| 437 | H | OH | Cyclopentyl | Ph | H |
| 438 | H | OH | Cyclohexyl | Ph | H |
| 439 | H | OH | OH | Ph | H |
| 440 | H | OH | —$OCH_3$ | Ph | H |
| 441 | H | OH | —$OC_2H_5$ | Ph | H |
| 442 | H | OH | —$OC_3H_7$ | Ph | H |
| 443 | H | OH | —$OC_4H_9$ | Ph | H |
| 444 | H | OH | —$OCH_2CH{=}CH_2$ | Ph | H |
| 445 | H | OH | —OPh | Ph | H |
| 446 | H | OH | —$OCH_2Ph$ | Ph | H |
| 447 | H | OH | —OCyclopropyl | Ph | H |
| 448 | H | OH | —OCyclobutyl | Ph | H |
| 449 | H | OH | —OCyclopentyl | Ph | H |
| 450 | H | OH | —OCyclohexyl | Ph | H |
| 451 | H | OH | SH | Ph | H |
| 452 | H | OH | —$SCH_3$ | Ph | H |
| 453 | H | OH | —$SC_2H_5$ | Ph | H |
| 454 | H | OH | —$SC_3H_7$ | Ph | H |
| 455 | H | OH | —$SC_4H_9$ | Ph | H |
| 456 | H | OH | —$SCH_2CH{=}CH_2$ | Ph | H |
| 457 | H | OH | —SPh | Ph | H |
| 458 | H | OH | —$SCH_2Ph$ | Ph | H |
| 459 | H | OH | —SCyclopropyl | Ph | H |
| 460 | H | OH | —SCyclobutyl | Ph | H |
| 461 | H | OH | —SCyclopentyl | Ph | H |
| 462 | H | OH | —SCyclohexyl | Ph | H |
| 463 | H | OH | $NH_2$ | Ph | H |
| 464 | H | OH | —$NHCH_3$ | Ph | H |
| 465 | H | OH | —$NHC_2H_5$ | Ph | H |
| 466 | H | OH | —$NHC_3H_7$ | Ph | H |
| 467 | H | OH | —$NHC_4H_9$ | Ph | H |
| 468 | H | OH | —$NHCH_2CH{=}CH_2$ | Ph | H |
| 469 | H | OH | —NHPh | Ph | H |
| 470 | H | OH | —$NHCH_2Ph$ | Ph | H |
| 471 | H | OH | —NHCyclopropyl | Ph | H |
| 472 | H | OH | —NHCyclobutyl | Ph | H |
| 473 | H | OH | —NHCyclopentyl | Ph | H |
| 474 | H | OH | —NHCyclohexyl | Ph | H |
| 475 | H | OH | —$N(CH_3)_2$ | Ph | H |
| 476 | H | OH | —$N(CH_3)(C_2H_5)$ | Ph | H |
| 477 | H | OH | —$N(C_2H_5)_2$ | Ph | H |

TABLE A-continued

| No. | $R^3$ | $R^4$ | $R^5$ | $R^6$ | $R^7$ |
|---|---|---|---|---|---|
| 478 | H | OH | —$N(CH_3)(C_3H_7)$ | Ph | H |
| 479 | H | OH | —$N(CH_3)C_4H_9$ | Ph | H |
| 480 | H | OH | —$N(CH_3)(CH_2CH{=}CH_2)$ | Ph | H |
| 481 | H | OH | —$N(CH_3)Ph$ | Ph | H |
| 482 | H | OH | —$N(C_2H_5)Ph$ | Ph | H |
| 483 | H | OH | —$N(Ph)_2$ | Ph | H |
| 484 | H | OH | —$N(C_2H_5)(CH_2Ph)$ | Ph | H |
| 485 | H | OH | —$N(CH_2Ph)_2$ | Ph | H |
| 486 | H | OH | —$N(CH_3)(CH_2Ph)$ | Ph | H |
| 487 | H | OH | —$N(CH_3)$Cyclopropyl | Ph | H |
| 488 | H | OH | —$N(CH_3)$Cyclobutyl | Ph | H |
| 489 | H | OH | —$N(CH_3)$Cyclopentyl | Ph | H |
| 490 | H | OH | —$N(CH_3)$Cyclohexyl | Ph | H |
| 491 | H | H | —$OCH_2CH_2$— | | H |
| 492 | $CH_3$ | H | —$OCH_2CH_2$— | | H |
| 493 | H | H | —$CH_2CH_2O$— | | H |
| 494 | $CH_3$ | H | —$CH_2CH_2O$— | | H |
| 495 | H | H | —$OCH{=}CH$— | | H |
| 496 | $CH_3$ | H | —$OCH{=}CH$— | | H |
| 497 | H | H | —$CH{=}CHO$— | | H |
| 498 | $CH_3$ | H | —$CH{=}CHO$— | | H |
| 499 | H | H | —$OCH_2CH_2CH_2$— | | H |
| 500 | $CH_3$ | H | —$OCH_2CH_2CH_2$— | | H |
| 501 | H | H | —$CH_2CH_2CH_2O$— | | H |
| 502 | $CH_3$ | H | —$CH_2CH_2CH_2O$— | | H |
| 503 | H | H | —$NHCH_2CH_2$— | | H |
| 504 | $CH_3$ | H | —$NHCH_2CH_2$— | | H |
| 505 | H | H | —$CH_2CH_2NH$— | | H |
| 506 | $CH_3$ | H | —$CH_2CH_2NH$— | | H |
| 507 | H | H | —$NHCH{=}CH$— | | H |
| 508 | $CH_3$ | H | —$NHCH{=}CH$— | | H |
| 509 | H | H | —$CH{=}CHNH$— | | H |
| 510 | $CH_3$ | H | —$CH{=}CHNH$— | | H |
| 511 | H | H | —$NHCH_2CH_2CH_2$— | | H |
| 512 | $CH_3$ | H | —$NHCH_2CH_2CH_2$— | | H |
| 513 | H | H | —$CH_2CH_2CH_2NH$— | | H |
| 514 | $CH_3$ | H | —$CH_2CH_2CH_2NH$— | | H |

The Tables 1–144 below are based on the 4-benzoylpyrazoles of the formula Ib.

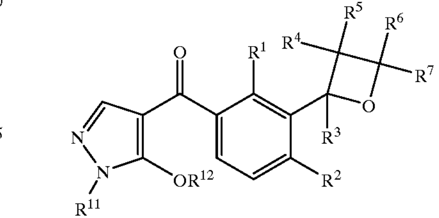

Table 1: Compounds 1.1–1.514

Compounds of the general formula Ib where $R^1$ is Cl, $R^2$ is methylsulfonyl, $R^{11}$ is methyl and $R^{12}$ is hydrogen and where for each individual compound the substituents $R^3$–$R^7$ correspond to one line of Table A.

Table 2: Compounds 2.1–2.514

Compounds of the general formula Ib, where $R^1$ is Cl, $R^2$ is methylsulfonyl, $R^{11}$ is ethyl, $R^{12}$ is hydrogen and where for each individual compound the substituents $R^3$–$R^7$ correspond to one line of Table A.

Table 3: Compounds 3.1–3.514

Compounds of the general formula Ib, where $R^1$ is Cl, $R^2$ is methylsulfonyl, $R^{11}$ is n-propyl, $R^{12}$ is hydrogen and where for each individual compound the substituents $R^3$–$R^7$ correspond to one line of Table A.

Table 4: Compounds 4.1–4.514

Compounds of the general formula Ib, where $R^1$ is Cl, $R^2$ is methylsulfonyl, $R^{11}$ is methyl, $R^{12}$ is methyl and where for each individual compound the substituents $R^3$–$R^7$ correspond to one line of Table A.

Table 5: Compounds 5.1–5.514

Compounds of the general formula Ib, where $R^1$ is Cl, $R^2$ is methylsulfonyl, $R^{11}$ is ethyl, $R^{12}$ is methyl and where for each individual compound the substituents $R^3$–$R^7$ correspond to one line of Table A.

Table 6: Compounds 6.1–6.514

Compounds of the general formula Ib, where $R^1$ is Cl, $R^2$ is methylsulfonyl, $R^{11}$ is n-propyl, $R^{12}$ is methyl and where for each individual compound the substituents $R^3$–$R^7$ correspond to one line of Table A.

Table 7: Compounds 7.1–7.514

Compounds of the general formula Ib, where $R^1$ is Cl, $R^2$ is methylsulfonyl, $R^{11}$ is methyl, $R^{12}$ is ethyl and where for each individual compound the substituents $R^3$–$R^7$ correspond to one line of Table A.

Table 8: Compounds 8.1–8.514

Compounds of the general formula Ib, where $R^1$ is Cl, $R^2$ is methylsulfonyl, $R^{11}$ is ethyl, $R^{12}$ is ethyl and where for each individual compound the substituents $R^3$–$R^7$ correspond to one line of Table A.

Table 9: Compounds 9.1–9.514

Compounds of the general formula Ib, where $R^1$ is Cl, $R^2$ is methylsulfonyl, $R^{11}$ is n-propyl, $R^{12}$ is ethyl and where for each individual compound the substituents $R^3$–$R^7$ correspond to one line of Table A.

Table 10: Compounds 10.1–10.514

Compounds of the general formula Ib, where $R^1$ is Cl, $R^2$ is methylsulfonyl, $R^{11}$ is methyl, $R^{12}$ is methylcarbonyl and where for each individual compound the substituents $R^3$–$R^7$ correspond to one line of Table A.

Table 11: Compounds 11.1–11.514

Compounds of the general formula Ib, where $R^1$ is Cl, $R^2$ is methylsulfonyl, $R^{11}$ is ethyl, $R^{12}$ is methylcarbonyl and where for each individual compound the substituents $R^3$–$R^7$ correspond to one line of Table A.

Table 12: Compounds 12.1–12.514

Compounds of the general formula Ib, where $R^1$is Cl, $R^2$ is methylsulfonyl, $R^{11}$ is n-propyl, $R^{12}$ is methylcarbonyl and where for each individual compound the substituents $R^3$–$R^7$ correspond to one line of Table A.

Table 13: Compounds 13.1–13.514

Compounds of the general formula Ib, where $R^1$ is Cl, $R^2$ is methylsulfonyl, $R^{11}$ is methyl, $R^{12}$ is ethylcarbonyl and where for each individual compound the substituents $R^3$–$R^7$ correspond to one line of Table A.

Table 14: Compounds 14.1–14.514

Compounds of the general formula Ib, where $R^1$ is Cl, $R^2$ is methylsulfonyl, $R^{11}$ is ethyl, $R^{12}$ is ethylcarbonyl and where for each individual compound the substituents $R^3$–$R^7$ correspond to one line of Table A.

Table 15: Compounds 15.1–15.514

Compounds of the general formula Ib, where $R^1$ is Cl, $R^2$ is methylsulfonyl, $R^{11}$ is n-propyl, $R^{12}$ is ethylcarbonyl and where for each individual compound the substituents $R^3$–$R^7$ correspond to one line of Table A.

Table 16: Compounds 16.1–16.514

Compounds of the general formula Ib, where $R^1$ is Cl, $R^2$ is methylsulfonyl, $R^{11}$ is methyl, $R^{12}$ is methylsulfonyl and where for each individual compound the substituents $R^3$–$R^7$ correspond to one line of Table A.

Table 17: Compounds 17.1–17.514

Compounds of the general formula Ib, where $R^1$ is Cl, $R^2$ is methylsulfonyl, $R^{11}$ is ethyl, $R^{12}$ is methylsulfonyl and where for each individual compound the substituents $R^3$–$R^7$ correspond to one line of Table A.

Table 18: Compounds 18.1–18.514

Compounds of the general formula Ib, where $R^1$ is Cl, $R^2$ is methylsulfonyl, $R^{11}$ is n-propyl, $R^{12}$ is methylsulfonyl and where for each individual compound the substituents $R^3$–$R^7$ correspond to one line of Table A.

Table 19: Compounds 19.1–19.514

Compounds of the general formula Ib, where $R^1$ is Cl, $R^2$ is methylsulfonyl, $R^{11}$ is methyl, $R^{12}$ is ethylsulfonyl and where for each individual compound the substituents $R^3$–$R^7$ correspond to one line of Table A.

Table 20: Compounds 20.1–20.514

Compounds of the general formula Ib, where $R^1$ is Cl, $R^2$ is methylsulfonyl, $R^{11}$ is ethyl, $R^{12}$ is ethylsulfonyl and where for each individual compound the substituents $R^3$–$R^7$ correspond to one line of Table A.

Table 21: Compounds 21.1–21.514

Compounds of the general formula Ib, where $R^1$ is Cl, $R^2$ is methylsulfonyl, $R^{11}$ is n-propyl, $R^{12}$ is ethylsulfonyl and where for each individual compound the substituents $R^3$–$R^7$ correspond to one line of Table A.

Table 22: Compounds 22.1–22.514

Compounds of the general formula Ib, where $R^1$ is Cl, $R^2$ is methylsulfonyl, $R^{11}$ is methyl, $R^{12}$ is 4-methylphenylsulfonyl and where for each individual compound the substituents $R^3$–$R^7$ correspond to one line of Table A.

Table 23: Compounds 23.1–23.514

Compounds of the general formula Ib, where $R^1$ is Cl, $R^2$ is methylsulfonyl, $R^{11}$ is ethyl, $R^{12}$ is 4-methylphenylsulfonyl and where for each individual compound the substituents $R^3$–$R^7$ correspond to one line of Table A.

Table 24: Compounds 24.1–24.514

Compounds of the general formula Ib, where $R^1$ is Cl, $R^2$ is methylsulfonyl, $R^{11}$ is n-propyl, $R^{12}$ is 4-methylphenylsulfonyl and where for each individual compound the substituents $R^3$–$R^7$ correspond to one line of Table A.

Table 25: Compounds 25.1–25.514

Compounds of the general formula Ib, where $R^1$ is Cl, $R^2$ is Cl, $R^{11}$ is methyl und $R^{12}$ is hydrogen and where for each individual compound the substituents $R^3$–$R^7$ correspond to one line of Table A.

Table 26: Compounds 26.1–26.514

Compounds of the general formula Ib, where $R^1$ is Cl, $R^2$ is Cl, $R^{11}$ is ethyl, $R^{12}$ is hydrogen and where for each individual compound the substituents $R^3$–$R^7$ correspond to one line of Table A.

Table 27: Compounds 27.1–27.514

Compounds of the general formula Ib, where $R^1$ is Cl, $R^2$ is Cl, $R^{11}$ is n-propyl, $R^{12}$ is hydrogen and where for each individual compound the substituents $R^3$–$R^7$ correspond to one line of Table A.

Table 28: Compounds 28.1–28.514

Compounds of the general formula Ib, where $R^1$ is Cl, $R^2$ is Cl, $R^{11}$ is methyl, $R^{12}$ is methyl and where for each individual compound the substituents $R^3$–$R^7$ correspond to one line of Table A.

Table 29: Compounds 29.1–29.514

Compounds of the general formula Ib, where $R^1$ is Cl, $R^2$ is Cl, $R^{11}$ is ethyl, $R^{12}$ is methyl and where for each individual compound the substituents $R^3$–$R^7$ correspond to one line of Table A.

Table 30: Compounds 30.1–30.514

Compounds of the general formula Ib, where $R^1$ is Cl, $R^2$ is Cl, $R^{11}$ is n-propyl, $R^{12}$ is methyl and where for each individual compound the substituents $R^3$–$R^7$ correspond to one line of Table A.

Table 31: Compounds 31.1–31.514

Compounds of the general formula Ib, where $R^1$ is Cl, $R^2$ is Cl, $R^{11}$ is methyl, $R^{12}$ is ethyl and where for each individual compound the substituents $R^3$–$R^7$ correspond to one line of Table A.

Table 32: Compounds 32.1–32.514

Compounds of the general formula Ib, where $R^1$ is Cl, $R^2$ is Cl, $R^{11}$ is ethyl, $R^{12}$ is ethyl and where for each individual compound the substituents $R^3$–$R^7$ correspond to one line of Table A.

Table 33: Compounds 33.1–33.514

Compounds of the general formula Ib, where $R^1$ is Cl, $R^2$ is Cl, $R^{11}$ is n-propyl, $R^{12}$ is ethyl and where for each individual compound the substituents $R^3$–$R^7$ correspond to one line of Table A.

Table 34: Compounds 34.1–34.514

Compounds of the general formula Ib, where $R^1$ is Cl, $R^2$ is Cl, $R^{11}$ is methyl, $R^{12}$ is methylcarbonyl and where for each individual compound the substituents $R^3$–$R^7$ correspond to one line of Table A.

Table 35: Compounds 35.1–35.514

Compounds of the general formula Ib, where $R^1$ is Cl, $R^2$ is Cl, $R^{11}$ is ethyl, $R^{12}$ is methylcarbonyl and where for each individual compound the substituents $R^3$–$R^7$ correspond to one line of Table A.

Table 36: Compounds 36.1–36.514

Compounds of the general formula Ib, where $R^1$ is Cl, $R^2$ is Cl, $R^{11}$ is n-propyl, $R^{12}$ is methylcarbonyl and where for each individual compound the substituents $R^3$–$R^7$ correspond to one line of Table A.

Table 37: Compounds 37.1–37.514

Compounds of the general formula Ib, where $R^1$ is Cl, $R^2$ is Cl, $R^{11}$ is methyl, $R^{12}$ is ethylcarbonyl and where for each individual compound the substituents $R^3$–$R^7$ correspond to one line of Table A.

Table 38: Compounds 38.1–38.514

Compounds of the general formula Ib, where $R^1$ is Cl, $R^2$ is Cl, $R^{11}$ is ethyl, $R^{12}$ is ethylcarbonyl and where for each individual compound the substituents $R^3$–$R^7$ correspond to one line of Table A.

Table 39: Compounds 39.1–39.514

Compounds of the general formula Ib, where $R^1$ is Cl, $R^2$ is Cl, $R^{11}$ is n-propyl, $R^{12}$ is ethylcarbonyl and where for each individual compound the substituents $R^3$–$R^7$ correspond to one line of Table A.

Table 40: Compounds 40.1–40.514

Compounds of the general formula Ib, where $R^1$ is Cl, $R^2$ is Cl, $R^{11}$ is methyl, $R^{12}$ is methylsulfonyl and where for each individual compound the substituents $R^3$–$R^7$ correspond to one line of Table A.

Table 41: Compounds 41.1–41.514

Compounds of the general formula Ib, where $R^1$ is Cl, $R^2$ is Cl, $R^{11}$ is ethyl, $R^{12}$ is methylsulfonyl and where for each individual compound the substituents $R^3$–$R^7$ correspond to one line of Table A.

Table 42: Compounds 42.1–42.514

Compounds of the general formula Ib, where $R^1$ is Cl, $R^2$ is Cl, $R^{11}$ is n-propyl, $R^{12}$ is methylsulfonyl and where for each individual compound the substituents $R^3$–$R^7$ correspond to one line of Table A.

Table 43: Compounds 43.1–43.514

Compounds of the general formula Ib, where $R^1$ is Cl, $R^2$ is Cl, $R^{11}$ is methyl, $R^{12}$ is ethylsulfonyl and where for each individual compound the substituents $R^3$–$R^7$ correspond to one line of Table A.

Table 44: Compounds 44.1–44.514

Compounds of the general formula Ib, where $R^1$ is Cl, $R^2$ is Cl, $R^{11}$ is ethyl, $R^{12}$ is ethylsulfonyl and where for each individual compound the substituents $R^3$–$R^7$ correspond to one line of Table A.

Table 45: Compounds 45.1–45.514

Compounds of the general formula Ib, where $R^1$ is Cl, $R^2$ is Cl, $R^{11}$ is n-propyl, $R^{12}$ is ethylsulfonyl and where for each individual compound the substituents $R^3$–$R^7$ correspond to one line of Table A.

Table 46: Compounds 46.1–46.514

Compounds of the general formula Ib, where $R^1$ is Cl, $R^2$ is Cl, $R^{11}$ is methyl, $R^{12}$ is 4-methylphenylsulfonyl and where for each individual compound the substituents $R^3$–$R^7$ correspond to one line of Table A.

Table 47: Compounds 47.1–47.514

Compounds of the general formula Ib, where $R^1$ is Cl, $R^2$ is Cl, $R^{11}$ is ethyl, $R^{12}$ is 4-methylphenylsulfonyl and where for each individual compound the substituents $R^3$–$R^7$ correspond to one line of Table A.

Table 48: Compounds 48.1–48.514

Compounds of the general formula Ib, where $R^1$ is Cl, $R^2$ is Cl, $R^{11}$ is n-propyl, $R^{12}$ is 4-methylphenylsulfonyl and where for each individual compound the substituents $R^3$–$R^7$ correspond to one line of Table A.

Table 49: Compounds 49.1–49.514

Compounds of the general formula Ib, where $R^1$ is Cl, $R^2$ is trifluoromethyl, $R^{11}$ is methyl and $R^{12}$ is hydrogen and where for each individual compound the substituents $R^3$–$R^7$ correspond to one line of Table A.

Table 50: Compounds 50.1–50.514

Compounds of the general formula Ib, where $R^1$ is Cl, $R^2$ is trifluoromethyl, $R^{11}$ is ethyl, $R^{12}$ is hydrogen and where for each individual compound the substituents $R^3$–$R^7$ correspond to one line of Table A.

Table 51: Compounds 51.1–51.514

Compounds of the general formula Ib, where $R^1$ is Cl, $R^2$ is trifluoromethyl, $R^{11}$ is n-propyl, $R^{12}$ is hydrogen and where for each individual compound the substituents $R^3$–$R^7$ correspond to one line of Table A. 35

Table 52: Compounds 52.1–52.514

Compounds of the general formula Ib, where $R^1$ is Cl, $R^2$ is trifluoromethyl, $R^{11}$ is methyl, $R^{12}$ is methyl and where for each individual compound the substituents $R^3$–$R^7$ correspond to one line of Table A.

Table 53: Compounds 53.1–53.514

Compounds of the general formula Ib, where $R^1$ is Cl, $R^2$ is trifluoromethyl, $R^{11}$ is ethyl, $R^{12}$ is methyl and where for each individual compound the substituents $R^3$–$R^7$ correspond to one line of Table A.

Table 54: Compounds 54.1–54.514

Compounds of the general formula Ib, where $R^1$ is Cl, $R^2$ is trifluoromethyl, $R^{11}$ is n-propyl, $R^{12}$ is methyl and where for each individual compound the substituents $R^3$–$R^7$ correspond to one line of Table A.

Table 55: Compounds 55.1–55.514

Compounds of the general formula Ib, where $R^1$ is Cl, $R^2$ is trifluoromethyl, $R^{11}$ is methyl, $R^{12}$ is ethyl and where for each individual compound the substituents $R^3$–$R^7$ correspond to one line of Table A.

Table 56: Compounds 56.1–56.514

Compounds of the general formula Ib, where $R^1$ is Cl, $R^2$ is trifluoromethyl, $R^{11}$ is ethyl, $R^{12}$ is ethyl and where for each individual compound the substituents $R^3$–$R^7$ correspond to one line of Table A.

Table 57: Compounds 57.1–57.514

Compounds of the general formula Ib, where $R^1$ is Cl, $R^2$ is trifluoromethyl, $R^{11}$ is n-propyl, $R^{12}$ is ethyl and where for each individual compound the substituents $R^3$–$R^7$ correspond to one line of Table A.

Table 58: Compounds 58.1–58.514

Compounds of the general formula Ib, where $R^1$ is Cl, $R^2$ is trifluoromethyl, $R^{11}$ is methyl, $R^{12}$ is methylcarbonyl and where for each individual compound the substituents $R^3$–$R^7$ correspond to one line of Table A.

Table 59: Compounds 59.1–59.514

Compounds of the general formula Ib, where $R^1$ is Cl, $R^2$ is trifluoromethyl, $R^{11}$ is ethyl, $R^{12}$ is methylcarbonyl and where for each individual compound the substituents $R^3$–$R^7$ correspond to one line of Table A.

Table 60: Compounds 60.1–60.514

Compounds of the general formula Ib, where $R^1$ is Cl, $R^2$ is trifluoromethyl, $R^{11}$ is n-propyl, $R^{12}$ is methylcarbonyl and where for each individual compound the substituents $R^3$–$R^7$ correspond to one line of Table A.

Table 61: Compounds 61.1–61.514

Compounds of the general formula Ib, where $R^1$ is Cl, $R^2$ is trifluoromethyl, $R^{11}$ is methyl, $R^{12}$ is ethylcarbonyl and where for each individual compound the substituents $R^3$–$R^7$ correspond to one line of Table A.

Table 62: Compounds 62.1–62.514

Compounds of the general formula Ib, where $R^1$ is Cl, $R^2$ is trifluoromethyl, $R^{11}$ is ethyl, $R^{12}$ is ethylcarbonyl and where for each individual compound the substituents $R^3$–$R^7$ correspond to one line of Table A.

Table 63: Compounds 63.1–63.514

Compounds of the general formula Ib, where $R^1$ is Cl, $R^2$ is trifluoromethyl, $R^{11}$ is n-propyl, $R^{12}$ is ethylcarbonyl and where for each individual compound the substituents $R^3$–$R^7$ correspond to one line of Table A.

Table 64: Compounds 64.1–64.514

Compounds of the general formula Ib, where $R^1$ is Cl, $R^2$ is trifluoromethyl, $R^{11}$ is methyl, $R^{12}$ is methylsulfonyl and where for each individual compound the substituents $R^3$–$R^7$ correspond to one line of Table A.

Table 65: Compounds 65.1–65.514

Compounds of the general formula Ib, where $R^1$ is Cl, $R^2$ is trifluoromethyl, $R^{11}$ is ethyl, $R^{12}$ is methylsulfonyl and where for each individual compound the substituents $R^3$–$R^7$ correspond to one line of Table A.

Table 66: Compounds 66.1–66.514

Compounds of the general formula Ib, where $R^1$ is Cl, $R^2$ is trifluoromethyl, $R^{11}$ is n-propyl, $R^{12}$ is methylsulfonyl and where for each individual compound the substituents $R^3$–$R^7$ correspond to one line of Table A.

Table 67: Compounds 67.1–67.514

Compounds of the general formula Ib, where $R^1$ is Cl, $R^2$ is trifluoromethyl, $R^{11}$ is methyl, $R^{12}$ is ethylsulfonyl and where for each individual compound the substituents $R^3$–$R^7$ correspond to one line of Table A.

Table 68: Compounds 68.1–68.514

Compounds of the general formula Ib, where $R^1$ is Cl, $R^2$ is trifluoromethyl, $R^{11}$ is ethyl, $R^{12}$ is ethylsulfonyl and where for each individual compound the substituents $R^3$–$R^7$ correspond to one line of Table A.

Table 69: Compounds 69.1–69.514

Compounds of the general formula Ib, where $R^1$ is Cl, $R^2$ is trifluoromethyl, $R^{11}$ is n-propyl, $R^{12}$ is ethylsulfonyl and where for each individual compound the substituents $R^3$–$R^7$ correspond to one line of Table A.

Table 70: Compounds 70.1–70.514

Compounds of the general formula Ib, where $R^1$ is Cl, $R^2$ is trifluoromethyl, $R^{11}$ is methyl, $R^{12}$ is 4-methylphenylsulfonyl and where for each individual compound the substituents $R^3$–$R^7$ correspond to one line of Table A.

Table 71: Compounds 71.1–71.514

Compounds of the general formula Ib, where $R^1$ is Cl, $R^2$ is trifluoromethyl, $R^{11}$ is ethyl, $R^{12}$ is 4-methylphenylsulfonyl and where for each individual compound the substituents $R^3$–$R^7$ correspond to one line of Table A.

Table 72: Compounds 72.1–72.514

Compounds of the general formula Ib, where $R^1$ is Cl, $R^2$ is trifluoromethyl, $R^{11}$ is n-propyl, $R^{12}$ is 4-methylphenylsulfonyl and where for each individual compound the substituents $R^3$–$R^7$ correspond to one line of Table A.

Table 73: Compounds 73.1–73.514

Compounds of the general formula Ib, where $R^1$ is methyl, $R^2$ is Cl, $R^{11}$ is methyl und $R^{12}$ is hydrogen and where for each individual compound the substituents $R^3$–$R^7$ correspond to one line of Table A.

Table 74: Compounds 74.1–74.514

Compounds of the general formula Ib, where $R^1$ is methyl, $R^2$ is Cl, $R^{11}$ is ethyl, $R^{12}$ is hydrogen and where for each individual compound the substituents $R^3$–$R^7$ correspond to one line of Table A.

Table 75: Compounds 75.1–75.514

Compounds of the general formula Ib, where $R^1$ is methyl, $R^2$ is Cl, $R^{11}$ is n-propyl, $R^{12}$ is hydrogen and where for each individual compound the substituents $R^3$–$R^7$ correspond to one line of Table A.

Table 76: Compounds 76.1–76.514

Compounds of the general formula Ib, where $R^1$ is methyl, $R^2$ is Cl, $R^{11}$ is methyl, $R^{12}$ is methyl and where for each individual compound the substituents $R^3$–$R^7$ correspond to one line of Table A.

Table 77: Compounds 77.1–77.514

Compounds of the general formula Ib, where $R^1$ is methyl, $R^2$ is Cl, $R^{11}$ is ethyl, $R^{12}$ is methyl and where for each individual compound the substituents $R^3$–$R^7$ correspond to one line of Table A.

Table 78: Compounds 78.1–78.514

Compounds of the general formula Ib, where $R^1$ is methyl, $R^2$ is Cl, $R^{11}$ is n-propyl, $R^{12}$ is methyl and where for each individual compound the substituents $R^3$–$R^7$ correspond to one line of Table A.

Table 79: Compounds 79.1–79.514

Compounds of the general formula Ib, where $R^1$ is methyl, $R^2$ is Cl, $R^{11}$ is methyl, $R^{12}$ is ethyl and where for each individual compound the substituents $R^3$–$R^7$ correspond to one line of Table A.

Table 80: Compounds 80.1–80.514

Compounds of the general formula Ib, where $R^1$ is methyl, $R^2$ is Cl, $R^{11}$ is ethyl, $R^{12}$ is ethyl and where for each individual compound the substituents $R^3$–$R^7$ correspond to one line of Table A.

Table 81: Compounds 81.1–81.514

Compounds of the general formula Ib, where $R^1$ is methyl, $R^2$ is Cl, $R^{11}$ is n-propyl, $R^{12}$ is ethyl and where for each individual compound the substituents $R^3$–$R^7$ correspond to one line of Table A.

Table 82: Compounds 82.1–82.514

Compounds of the general formula Ib, where $R^1$ is methyl, $R^2$ is Cl, $R^{11}$ is methyl, $R^{12}$ is methylcarbonyl and where for each individual compound the substituents $R^3$–$R^7$ correspond to one line of Table A.

Table 83: Compounds 83.1–83.514

Compounds of the general formula Ib, where $R^1$ is methyl, $R^2$ is Cl, $R^{11}$ is ethyl, $R^{12}$ is methylcarbonyl and where for each individual compound the substituents $R^3$–$R^7$ correspond to one line of Table A.

Table 84: Compounds 84.1–84.514

Compounds of the general formula Ib, where $R^1$ is methyl, $R^2$ is Cl, $R^{11}$ is n-propyl, $R^{12}$ is methylcarbonyl and where for each individual compound the substituents $R^3$–$R^7$ correspond to one line of Table A.

Table 85: Compounds 85.1–85.514

Compounds of the general formula Ib, where $R^1$ is methyl, $R^2$ is Cl, $R^{11}$ is methyl, $R^{12}$ is ethylcarbonyl and where for each individual compound the substituents $R^3$–$R^7$ correspond to one line of Table A.

Table 86: Compounds 86.1–86.514

Compounds of the general formula Ib, where $R^1$ is methyl, $R^2$ is Cl, $R^{11}$ is ethyl, $R^{12}$ is ethylcarbonyl and where for each individual compound the substituents $R^3$–$R^7$ correspond to one line of Table A.

Table 87: Compounds 87.1–87.514

Compounds of the general formula Ib, where $R^1$ is methyl, $R^2$ is Cl, $R^{11}$ is n-propyl, $R^{12}$ is ethylcarbonyl and where for each individual compound the substituents $R^3$–$R^7$ correspond to one line of Table A.

Table 88: Compounds 88.1–88.514

Compounds of the general formula Ib, where $R^1$ is methyl, $R^2$ is Cl, $R^{11}$ is methyl, $R^{12}$ is methylsulfonyl and where for each individual compound the substituents $R^3$–$R^7$ correspond to one line of Table A.

Table 89: Compounds 89.1–89.514

Compounds of the general formula Ib, where $R^1$ is methyl, $R^2$ is Cl, $R^{11}$ is ethyl, $R^{12}$ is methylsulfonyl and where for each individual compound the substituents $R^3$–$R^7$ correspond to one line of Table A.

Table 90: Compounds 90.1–90.514

Compounds of the general formula Ib, where $R^1$ is methyl, $R^2$ is Cl, $R^{11}$ is n-propyl, $R^{12}$ is methylsulfonyl and where for each individual compound the substituents $R^3$–$R^7$ correspond to one line of Table A.

Table 91: Compounds 91.1–91.514

Compounds of the general formula Ib, where $R^1$ is methyl, $R^2$ is Cl, $R^{11}$ is methyl, $R^{12}$ is ethylsulfonyl and where for each individual compound the substituents $R^3$–$R^7$ correspond to one line of Table A.

Table 92: Compounds 92.1–92.514

Compounds of the general formula Ib, where $R^1$ is methyl, $R^2$ is Cl, $R^{11}$ is ethyl, $R^{12}$ is ethylsulfonyl and where for each individual compound the substituents $R^3$–$R^7$ correspond to one line of Table A.

Table 93: Compounds 93.1–93.514

Compounds of the general formula Ib, where $R^1$ is methyl, $R^2$ is Cl, $R^{11}$ is n-propyl, $R^{12}$ is ethylsulfonyl and where for each individual compound the substituents $R^3$–$R^7$ correspond to one line of Table A.

Table 94: Compounds 94.1–94.514

Compounds of the general formula Ib, where $R^1$ is methyl, $R^2$ is Cl, $R^{11}$ is methyl, $R^{12}$ is 4-methylphenylsulfonyl and where for each individual compound the substituents $R^3$–$R^7$ correspond to one line of Table A.

Table 95: Compounds 95.1–95.514

Compounds of the general formula Ib, where $R^1$ is methyl, $R^2$ is Cl, $R^{11}$ is ethyl, $R^{12}$ is 4-methylphenylsulfonyl and where for each individual compound the substituents $R^3$–$R^7$ correspond to one line of Table A.

Table 96: Compounds 96.1–96.514

Compounds of the general formula Ib, where $R^1$ is methyl, $R^2$ is Cl, $R^{11}$ is n-propyl, $R^{12}$ is 4-methylphenylsulfonyl and where for each individual compound the substituents $R^3$–$R^7$ correspond to one line of Table A.

Table 97: Compounds 97.1–97.514

Compounds of the general formula Ib, where $R^1$ is methyl, $R^2$ is methylsulfonyl, $R^{11}$ is methyl und $R^{12}$ is hydrogen and where for each individual compound the substituents $R^3$–$R^7$ correspond to one line of Table A.

Table 98: Compounds 98.1–98.514

Compounds of the general formula Ib, where $R^1$ is methyl, $R^2$ is methylsulfonyl, $R^{11}$ is ethyl, $R^{12}$ is hydrogen and where for each individual compound the substituents $R^3$–$R^7$ correspond to one line of Table A.

Table 99: Compounds 99.1–99.514

Compounds of the general formula Ib, where $R^1$ is methyl, $R^2$ is methylsulfonyl, $R^{11}$ is n-propyl, $R^{12}$ is hydrogen and where for each individual compound the substituents $R^3$–$R^7$ correspond to one line of Table A.

Table 100: Compounds 100.1–100.514

Compounds of the general formula Ib, where $R^1$ is methyl, $R^2$ is methylsulfonyl, $R^{11}$ is methyl, $R^{12}$ is methyl and where for each individual compound the substituents $R^3$–$R^7$ correspond to one line of Table A.

Table 101: Compounds 101.1–101.514

Compounds of the general formula Ib, where $R^1$ is methyl, $R^2$ is methylsulfonyl, $R^{11}$ is ethyl, $R^{12}$ is methyl and where for each individual compound the substituents $R^3$–$R^7$ correspond to one line of Table A.

Table 102: Compounds 102.1–102.514

Compounds of the general formula Ib, where $R^1$ is methyl, $R^2$ is methylsulfonyl, $R^{11}$ is n-propyl, $R^{12}$ is methyl and where for each individual compound the substituents $R^3$–$R^7$ correspond to one line of Table A.

Table 103: Compounds 103.1–103.514

Compounds of the general formula Ib, where $R^1$ is methyl, $R^2$ is methylsulfonyl, $R^{11}$ is methyl, $R^{12}$ is ethyl and where for each individual compound the substituents $R^3$–$R^7$ correspond to one line of Table A.

Table 104: Compounds 104.1–104.514

Compounds of the general formula Ib, where $R^1$ is methyl, $R^2$ is methylsulfonyl, $R^{11}$ is ethyl, $R^{12}$ is ethyl and where for each individual compound the substituents $R^3$–$R^7$ correspond to one line of Table A.

Table 105: Compounds 105.1–105.514

Compounds of the general formula Ib, where $R^1$ is methyl, $R^2$ is methylsulfonyl, $R^{11}$ is n-propyl, $R^{12}$ is ethyl and where for each individual compound the substituents $R^3$–$R^7$ correspond to one line of Table A.

Table 106: Compounds 106.1–106.514

Compounds of the general formula Ib, where $R^1$ is methyl, $R^2$ is methylsulfonyl, $R^{11}$ is methyl, $R^{12}$ is methylcarbonyl and where for each individual compound the substituents $R^3$–$R^7$ correspond to one line of Table A.

Table 107: Compounds 107.1–107.514

Compounds of the general formula Ib, where $R^1$ is methyl, $R^2$ is methylsulfonyl, $R^{11}$ is ethyl, $R^{12}$ is methylcarbonyl and where for each individual compound the substituents $R^3$–$R^7$ correspond to one line of Table A.

Table 108: Compounds 108.1–108.514

Compounds of the general formula Ib, where $R^1$ is methyl, $R^2$ is methylsulfonyl, $R^{11}$ is n-propyl, $R^{12}$ is methylcarbonyl and where for each individual compound the substituents $R^3$–$R^7$ correspond to one line of Table A.

Table 109: Compounds 109.1–109.514

Compounds of the general formula Ib, where $R^1$ is methyl, $R^2$ is methylsulfonyl, $R^{11}$ is methyl, $R^{12}$ is ethylcarbonyl and where for each individual compound the substituents $R^3$–$R^7$ correspond to one line of Table A.

Table 110: Compounds 110.1–110.514

Compounds of the general formula Ib, where $R^1$ is methyl, $R^2$ is methylsulfonyl, $R^{11}$ is ethyl, $R^{12}$ is ethylcarbonyl and where for each individual compound the substituents $R^3$–$R^7$ correspond to one line of Table A.

Table 111: Compounds 111.1–111.514

Compounds of the general formula Ib, where $R^1$ is methyl, $R^2$ is methylsulfonyl, $R^{11}$ is n-propyl, $R^{12}$ is ethylcarbonyl and where for each individual compound the substituents $R^3$–$R^7$ correspond to one line of Table A.

Table 112: Compounds 112.1–112.514

Compounds of the general formula Ib, where $R^1$ is methyl, $R^2$ is methylsulfonyl, $R^{11}$ is methyl, $R^{12}$ is methylsulfonyl and where for each individual compound the substituents $R^3$–$R^7$ correspond to one line of Table A.

Table 113: Compounds 113.1–113.514

Compounds of the general formula Ib, where $R^1$ is methyl, $R^2$ is methylsulfonyl, $R^{11}$ is ethyl, $R^{12}$ is methylsulfonyl and where for each individual compound the substituents $R^3$–$R^7$ correspond to one line of Table A.

Table 114: Compounds 114.1–114.514

Compounds of the general formula Ib, where $R^1$ is methyl, $R^2$ is methylsulfonyl, $R^{11}$ is n-propyl, $R^{12}$ is methylsulfonyl and where for each individual compound the substituents $R^3$–$R^7$ correspond to one line of Table A.

Table 115: Compounds 115.1–115.514

Compounds of the general formula Ib, where $R^1$ is methyl, $R^2$ is methylsulfonyl, $R^{11}$ is methyl, $R^{12}$ is ethylsulfonyl and where for each individual compound the substituents $R^3$–$R^7$ correspond to one line of Table A.

Table 116: Compounds 116.1–116.514

Compounds of the general formula Ib, where $R^1$ is methyl, $R^2$ is methylsulfonyl, $R^{11}$ is ethyl, $R^{12}$ is ethylsulfonyl and where for each individual compound the substituents $R^3$–$R^7$ correspond to one line of Table A.

Table 117: Compounds 117.1–117.514

Compounds of the general formula Ib, where $R^1$ is methyl, $R^2$ is methylsulfonyl, $R^{11}$ is n-propyl, $R^{12}$ is ethylsulfonyl and where for each individual compound the substituents $R^3$–$R^7$ correspond to one line of Table A.

Table 118: Compounds 118.1–118.514

Compounds of the general formula Ib, where $R^1$ is methyl, $R^2$ is methylsulfonyl, $R^{11}$ is methyl, $R^{12}$ is 4-methylphenylsulfonyl and where for each individual compound the substituents $R^3$–$R^7$ correspond to one line of Table A.

Table 119: Compounds 119.1–119.514

Compounds of the general formula Ib, where $R^1$ is methyl, $R^2$ is methylsulfonyl, $R^{11}$ is ethyl, $R^{12}$ is 4-methylphenylsulfonyl and where for each individual compound the substituents $R^3$–$R^7$ correspond to one line of Table A.

Table 120: Compounds 120.1–120.514

Compounds of the general formula Ib, where $R^1$ is methyl, $R^2$ is methylsulfonyl, $R^{11}$ is n-propyl, $R^{12}$ is 4-methylphenylsulfonyl and where for each individual compound the substituents $R^3$–$R^7$ correspond to one line of Table A.

Table 121: Compounds 121.1–121.514

Compounds of the general formula Ib, where $R^1$ is methyl, $R^2$ is trifluoromethyl, $R^{11}$ is methyl and $R^{12}$ is hydrogen and where for each individual compound the substituents $R^3$–$R^7$ correspond to one line of Table A.

Table 122: Compounds 122.1–122.514

Compounds of the general formula Ib, where $R^1$ is methyl, $R^2$ is trifluoromethyl, $R^{11}$ is ethyl, $R^{12}$ is hydrogen and where for each individual compound the substituents $R^3$–$R^7$ correspond to one line of Table A.

Table 123: Compounds 123.1–123.514

Compounds of the general formula Ib, where $R^1$ is methyl, $R^2$ is trifluoromethyl, $R^{11}$ is n-propyl, $R^{12}$ is hydrogen and where for each individual compound the substituents $R^3$–$R^7$ correspond to one line of Table A.

Table 124: Compounds 124.1–124.514

Compounds of the general formula Ib, where $R^1$ is methyl, $R^2$ is trifluoromethyl, $R^{11}$ is methyl, $R^{12}$ is methyl and where for each individual compound the substituents $R^3$–$R^7$ correspond to one line of Table A.

Table 125: Compounds 125.1–125.514

Compounds of the general formula Ib, where $R^1$ is methyl, $R^2$ is trifluoromethyl, $R^{11}$ is ethyl, $R^{12}$ is methyl and where for each individual compound the substituents $R^3$–$R^7$ correspond to one line of Table A.

Table 126: Compounds 126.1–126.514

Compounds of the general formula Ib, where $R^1$ is methyl, $R^2$ is trifluoromethyl, $R^{11}$ is n-propyl, $R^{12}$ is methyl and where for each individual compound the substituents $R^3$–$R^7$ correspond to one line of Table A.

Table 127: Compounds 127.1–127.514

Compounds of the general formula Ib, where $R^1$ methyl, $R^2$ is trifluoromethyl, $R^{11}$ is methyl, $R^{12}$ is ethyl and where for each individual compound the substituents $R^3$–$R^7$ correspond to one line of Table A.

Table 128: Compounds 128.1–128.514

Compounds of the general formula Ib, where $R^1$ is methyl, $R^2$ is trifluoromethyl, $R^{11}$ is ethyl, $R^{12}$ is ethyl and where for each individual compound the substituents $R^3$–$R^7$ correspond to one line of Table A.

Table 129: Compounds 129.1–129.514

Compounds of the general formula Ib, where $R^1$ is methyl, $R^2$ is trifluoromethyl, $R^{11}$ is n-propyl, $R^{12}$ is ethyl and where for each individual compound the substituents $R^3$–$R^7$ correspond to one line of Table A.

Table 130: Compounds 130.1–130.514

Compounds of the general formula Ib, where $R^1$ is methyl, $R^2$ is trifluoromethyl, $R^{11}$ is methyl, $R^{12}$ is methylcarbonyl and where for each individual compound the substituents $R^3$–$R^7$ correspond to one line of Table A.

Table 131: Compounds 131.1–131.514

Compounds of the general formula Ib, where $R^1$ is methyl, $R^2$ is trifluoromethyl, $R^{11}$ is ethyl, $R^{12}$ is methylcarbonyl and where for each individual compound the substituents $R^3$–$R^7$ correspond to one line of Table A.

Table 132: Compounds 132.1–132.514

Compounds of the general formula Ib, where $R^1$ is methyl, $R^2$ is trifluoromethyl, $R^{11}$ is n-propyl, $R^{12}$ is methylcarbonyl and where for each individual compound the substituents $R^3$–$R^7$ correspond to one line of Table A.

Table 133: Compounds 133.1–133.514

Compounds of the general formula Ib, where $R^1$ is methyl, $R^2$ is trifluoromethyl, $R^{11}$ is methyl, $R^{12}$ is ethylcarbonyl and where for each individual compound the substituents $R^3$–$R^7$ correspond to one line of Table A.

Table 134: Compounds 134.1–134.514

Compounds of the general formula Ib, where $R^1$ is methyl, $R^2$ is trifluoromethyl, $R^{11}$ is ethyl, $R^{12}$ is ethylcarbonyl and where for each individual compound the substituents $R^3$–$R^7$ correspond to one line of Table A.

Table 135: Compounds 135.1–135.514

Compounds of the general formula Ib, where $R^1$ is methyl, $R^2$ is trifluoromethyl, $R^{11}$ is n-propyl, $R^{12}$ is ethylcarbonyl and where for each individual compound the substituents $R^3$–$R^7$ correspond to one line of Table A.

Table 136: Compounds 136.1–136.514

Compounds of the general formula Ib, where $R^1$ is methyl, $R^2$ is trifluoromethyl, $R^{11}$ is methyl, $R^{12}$ is methylsulfonyl and where for each individual compound the substituents $R^3$–$R^7$ correspond to one line of Table A.

Table 137: Compounds 137.1–137.514

Compounds of the general formula Ib, where $R^1$ is methyl, $R^2$ is trifluoromethyl, $R^{11}$ is ethyl, $R^{12}$ is methylsulfonyl and where for each individual compound the substituents $R^3$–$R^7$ correspond to one line of Table A.

Table 138: Compounds 138.1–138.514

Compounds of the general formula Ib, where $R^1$ is methyl, $R^2$ is trifluoromethyl, $R^{11}$ is n-propyl, $R^{12}$ is methylsulfonyl and where for each individual compound the substituents $R^3$–$R^7$ correspond to one line of Table A.

Table 139: Compounds 139.1–139.514

Compounds of the general formula Ib, where $R^1$ is methyl, $R^2$ is trifluoromethyl, $R^{11}$ is methyl, $R^{12}$ is ethylsulfonyl and where for each individual compound the substituents $R^3$–$R^7$ correspond to one line of Table A.

Table 140: Compounds 140.1–140.514

Compounds of the general formula Ib, where $R^1$ is methyl, $R^2$ is trifluoromethyl, $R^{11}$ is ethyl, $R^{12}$ is ethylsulfonyl and where for each individual compound the substituents $R^3$–$R^7$ correspond to one line of Table A.

Table 141: Compounds 141.1–141.514

Compounds of the general formula Ib, where $R^1$ is methyl, $R^2$ is trifluoromethyl, $R^{11}$ is n-propyl, $R^{12}$ is ethylsulfonyl and where for each individual compound the substituents $R^3$–$R^7$ correspond to one line of Table A.

Table 142: Compounds 142.1–142.514

Compounds of the general formula Ib, where $R^1$ is methyl, $R^2$ is trifluoromethyl, $R^{11}$ is methyl, $R^{12}$ is 4-methylphenylsulfonyl and where for each individual compound the substituents $R^3$–$R^7$ correspond to one line of Table A.

Table 143: Compounds 143.1–143.514

Compounds of the general formula Ib, where $R^1$ is methyl, $R^2$ is trifluoromethyl, $R^{11}$ is ethyl, $R^{12}$ is 4-methylphenylsulfonyl and where for each individual compound the substituents $R^3$–$R^7$ correspond to one line of Table A.

Table 144: Compounds 144.1–144.514

Compounds of the general formula Ib, where $R^1$ is methyl, $R^2$ is trifluoromethyl, $R^{11}$ is n-propyl, $R^{12}$ is 4-methylphenylsulfonyl and where for each individual compound the substituents $R^3$–$R^7$ correspond to one line of Table A.

TABLE B

| No. | $R^3$ | $R^4$ | $R^5$ |
|---|---|---|---|
| 1 | H | OH | H |
| 2 | H | OH | —$CH_3$ |
| 3 | H | OH | —$C_2H_5$ |
| 4 | H | OH | —$C_3H_7$ |
| 5 | H | OH | —$C_4H_9$ |
| 6 | H | OH | —CH═$CH_2$ |
| 7 | H | OH | —$CH_2$CH═$CH_2$ |
| 8 | H | OH | —$CH_2$CH═CHPh |
| 9 | H | OH | —$CH_2$CH═$CHCH_3$ |
| 10 | H | OH | —C═CH |
| 11 | H | OH | —C═$CCH_3$ |
| 12 | H | OH | —C═CPh |
| 13 | H | OH | Ph |
| 14 | H | OH | —$CH_2$Ph |
| 15 | H | OH | cyclopropyl |
| 16 | H | OH | cyclobutyl |
| 17 | H | OH | cylopentyl |
| 18 | H | OH | cyclohexyl |
| 19 | H | OH | OH |
| 20 | H | OH | —$OCH_3$ |
| 21 | H | OH | —$OC_2H_5$ |
| 22 | H | OH | —$OC_3H_7$ |
| 23 | H | OH | —$OC_4H_9$ |
| 24 | H | OH | —$OCH_2$CH═$CH_2$ |
| 25 | H | OH | —OPh |
| 26 | H | OH | —$OCH_2$Ph |
| 27 | H | OH | —Ocyclopropyl |
| 28 | H | OH | —Ocyclobutyl |
| 29 | H | OH | —Ocyclopentyl |
| 30 | H | OH | —OCyclohexyl |
| 31 | H | OH | SH |
| 32 | H | OH | —$SCH_3$ |
| 33 | H | OH | —$SC_2H_5$ |
| 34 | H | OH | —$SC_3H_7$ |
| 35 | H | OH | —$SC_4H_9$ |
| 36 | H | OH | —$SCH_2$CH═$CH_2$ |
| 37 | H | OH | —SPh |
| 38 | H | OH | —$SCH_2$Ph |
| 39 | H | OH | —Scyclopropyl |
| 40 | H | OH | —Scyclobutyl |

TABLE B-continued

| No. | $R^3$ | $R^4$ | $R^5$ |
|---|---|---|---|
| 41 | H | OH | —Scyclopentyl |
| 42 | H | OH | —Scyclohexyl |
| 43 | H | OH | $NH_2$ |
| 44 | H | OH | —$NHCH_3$ |
| 45 | H | OH | —$NHC_2H_5$ |
| 46 | H | OH | —$NHC_3H_7$ |
| 47 | H | OH | —$NHC_4H_9$ |
| 48 | H | OH | —$NHCH_2CH$═$CH_2$ |
| 49 | H | OH | —NHPh |
| 50 | H | OH | —$NHCH_2Ph$ |
| 51 | H | OH | —NHcyclopropyl |
| 52 | H | OH | —NHcyclobutyl |
| 53 | H | OH | —NHcyclopentyl |
| 54 | H | OH | —NHcyclohexyl |
| 55 | H | OH | —$N(CH_3)_2$ |
| 56 | H | OH | —$N(CH_3)(C_2H_5)$ |
| 57 | H | OH | —$N(C_2H_5)_2$ |
| 58 | H | OH | —$N(CH_3)(C_3H_7)$ |
| 59 | H | OH | —$N(CH_3)C_4H_9$ |
| 60 | H | OH | —$N(CH_3)(CH_2CH$═$CH_2)$ |
| 61 | H | OH | —$N(CH_3)Ph$ |
| 62 | H | OH | —$N(C_2H_5)Ph$ |
| 63 | H | OH | —$N(Ph)_2$ |
| 64 | H | OH | —$N(C_2H_5)(CH_2Ph)$ |
| 65 | H | OH | —$N(CH_2Ph)_2$ |
| 66 | H | OH | —$N(CH_3)(CH_2Ph)$ |
| 67 | H | OH | —$N(CH_3)$cyclopropyl |
| 68 | H | OH | —$N(CH_3)$cyclobutyl |
| 69 | H | OH | —$N(CH_3)$cyclopentyl |
| 70 | H | OH | —$N(CH_3)$cyclohexyl |
| 71 | H | —$OSi(CH_3)_3$ | H |
| 72 | H | —$OSi(CH_3)_3$ | —$CH_3$ |
| 73 | H | —$OSi(CH_3)_3$ | —$C_2H_5$ |
| 74 | H | —$OSi(CH_3)_3$ | —$C_3H_7$ |
| 75 | H | —$OSi(CH_3)_3$ | —$C_4H_9$ |
| 76 | H | —$OSi(CH_3)_3$ | —CH═$CH_2$ |
| 77 | H | —$OSi(CH_3)_3$ | —$CH_2CH$═$CH_2$ |
| 78 | H | —$OSi(CH_3)_3$ | —$CH_2CH$═CHPh |
| 79 | H | —$OSi(CH_3)_3$ | —$CH_2CH$═$CHCH_3$ |
| 80 | H | —$OSi(CH_3)_3$ | —C═CH |
| 81 | H | —$OSi(CH_3)_3$ | —C═$CCH_3$ |
| 82 | H | —$OSi(CH_3)_3$ | —C═CPh |
| 83 | H | —$OSi(CH_3)_3$ | Ph |
| 84 | H | —$OSi(CH_3)_3$ | —$CH_2Ph$ |
| 85 | H | —$OSi(CH_3)_3$ | cyclopropyl |
| 86 | H | —$OSi(CH_3)_3$ | cyclobutyl |
| 87 | H | —$OSi(CH_3)_3$ | cyclopentyl |
| 88 | H | —$OSi(CH_3)_3$ | cyclohexyl |
| 89 | H | —$OSi(CH_3)_3$ | OH |
| 90 | H | —$OSi(CH_3)_3$ | —$OCH_3$ |
| 91 | H | —$OSi(CH_3)_3$ | —$OC_2H_5$ |
| 92 | H | —$OSi(CH_3)_3$ | —$OC_3H_7$ |
| 93 | H | —$OSi(CH_3)_3$ | —$OC_4H_9$ |
| 94 | H | —$OSi(CH_3)_3$ | —$OCH_2CH$═$CH_2$ |
| 95 | H | —$OSi(CH_3)_3$ | —OPh |
| 96 | H | —$OSi(CH_3)_3$ | —$OCH_2Ph$ |
| 97 | H | —$OSi(CH_3)_3$ | —Ocyclopropyl |
| 98 | H | —$OSi(CH_3)_3$ | —Ocyclobutyl |
| 99 | H | —$OSi(CH_3)_3$ | —Ocyclopentyl |
| 100 | H | —$OSi(CH_3)_3$ | —Ocyclohexyl |
| 101 | H | —$OSi(CH_3)_3$ | SH |
| 102 | H | —$OSi(CH_3)_3$ | —$SCH_3$ |
| 103 | H | —$OSi(CH_3)_3$ | —$SC_2H_5$ |
| 104 | H | —$OSi(CH_3)_3$ | —$SC_3H_7$ |
| 105 | H | —$OSi(CH_3)_3$ | —$SC_4H_9$ |
| 106 | H | —$OSi(CH_3)_3$ | —$SCH_2CH$═$CH_2$ |
| 107 | H | —$OSi(CH_3)_3$ | —SPh |
| 108 | H | —$OSi(CH_3)_3$ | —$SCH_2Ph$ |
| 109 | H | —$OSi(CH_3)_3$ | —Scyclopropyl |
| 110 | H | —$OSi(CH_3)_3$ | —Scyclobutyl |
| 111 | H | —$OSi(CH_3)_3$ | —Scyclopentyl |
| 112 | H | —$OSi(CH_3)_3$ | —Scyclohexyl |
| 113 | H | —$OSi(CH_3)_3$ | $NH_2$ |
| 114 | H | —$OSi(CH_3)_3$ | —$NHCH_3$ |
| 115 | H | —$OSi(CH_3)_3$ | —$NHC_2H_5$ |
| 116 | H | —$OSi(CH_3)_3$ | —$NHC_3H_7$ |
| 117 | H | —$OSi(CH_3)_3$ | —$NHC_4H_9$ |
| 118 | H | —$OSi(CH_3)_3$ | —$NHCH_2CH$═$CH_2$ |
| 119 | H | —$OSi(CH_3)_3$ | —NHPh |
| 120 | H | —$OSi(CH_3)_3$ | —$NHCH_2Ph$ |
| 121 | H | —$OSi(CH_3)_3$ | —NHcyclopropyl |
| 122 | H | —$OSi(CH_3)_3$ | —NHcyclobutyl |
| 123 | H | —$OSi(CH_3)_3$ | —NHcyclopentyl |
| 124 | H | —$OSi(CH_3)_3$ | —NHcyclohexyl |
| 125 | H | —$OSi(CH_3)_3$ | —$N(CH_3)_2$ |
| 126 | H | —$OSi(CH_3)_3$ | —$N(CH_3)(C_2H_5)$ |
| 127 | H | —$OSi(CH_3)_3$ | —$N(C_2H_5)_2$ |
| 128 | H | —$OSi(CH_3)_3$ | —$N(CH_3)(C_3H_7)$ |
| 129 | H | —$OSi(CH_3)_3$ | —$N(CH_3)C_4H_9$ |
| 130 | H | —$OSi(CH_3)_3$ | —$N(CH_3)(CH_2CH$═$CH_2)$ |
| 131 | H | —$OSi(CH_3)_3$ | —$N(CH_3)Ph$ |
| 132 | H | —$OSi(CH_3)_3$ | —$N(C_2H_5)Ph$ |
| 133 | H | —$OSi(CH_3)_3$ | —$N(Ph)_2$ |
| 134 | H | —$OSi(CH_3)_3$ | —$N(C_2H_5)(CH_2Ph)$ |
| 135 | H | —$OSi(CH_3)_3$ | —$N(CH_2Ph)_2$ |
| 136 | H | —$OSi(CH_3)_3$ | —$N(CH_3)(CH_2Ph)$ |
| 137 | H | —$OSi(CH_3)_3$ | —$N(CH_3)$cyclopropyl |
| 138 | H | —$OSi(CH_3)_3$ | —$N(CH_3)$cyclobutyl |
| 139 | H | —$OSi(CH_3)_3$ | —$N(CH_3)$cyclopentyl |
| 140 | H | —$OSi(CH_3)_3$ | —$N(CH_3)$cyclohexyl |
| 141 | H | —$OCH_3$ | H |
| 142 | H | —$OCH_3$ | —$CH_3$ |
| 143 | H | —$OCH_3$ | —$C_{2HS}$ |
| 144 | H | —$OCH_3$ | —$C_3H_7$ |
| 145 | H | —$OCH_3$ | —$C_4H_9$ |
| 146 | H | —$OCH_3$ | —CH═$CH_2$ |
| 147 | H | —$OCH_3$ | —$CH_2CH$═$CH_2$ |
| 148 | H | —$OCH_3$ | —$CH_2CH$═CHPh |
| 149 | H | —$OCH_3$ | —$CH_2CH$═$CHCH_3$ |
| 150 | H | —$OCH_3$ | —C═CH |
| 151 | H | —$OCH_3$ | —C═$CCH_3$ |
| 152 | H | —$OCH_3$ | —C═CPh |
| 153 | H | —$OCH_3$ | Ph |
| 154 | H | —$OCH_3$ | —$CH_2Ph$ |
| 155 | H | —$OCH_3$ | cyclopropyl |
| 156 | H | —$OCH_3$ | cyclobutyl |
| 157 | H | —$OCH_3$ | cyclopentyl |
| 158 | H | —$OCH_3$ | cyclohexyl |
| 159 | H | —$OCH_3$ | OH |
| 160 | H | —$OCH_3$ | —$OCH_3$ |
| 161 | H | —$OCH_3$ | —$OC_2H_5$ |
| 162 | H | —$OCH_3$ | —$OC_3H_7$ |
| 163 | H | —$OCH_3$ | —$OC_4H_9$ |
| 164 | H | —$OCH_3$ | —$OCH_2CH$═$CH_2$ |
| 165 | H | —$OCH_3$ | —OPh |
| 166 | H | —$OCH_3$ | —$OCH_2Ph$ |
| 167 | H | —$OCH_3$ | —Ocyclopropyl |
| 168 | H | —$OCH_3$ | —Ocyclobutyl |
| 169 | H | —$OCH_3$ | —Ocycopentyl |
| 170 | H | —$OCH_3$ | —Ocyclohexyl |
| 171 | H | —$OCH_3$ | SH |
| 172 | H | —$OCH_3$ | —$SCH_3$ |
| 173 | H | —$OCH_3$ | —$SC_2H_5$ |
| 174 | H | —$OCH_3$ | —$SC_3H_7$ |
| 175 | H | —$OCH_3$ | —$SC_4H_9$ |
| 176 | H | —$OCH_3$ | —$SCH_2CH$═$CH_2$ |
| 177 | H | —$OCH_3$ | —SPh |
| 178 | H | —$OCH_3$ | —$SCH_2Ph$ |
| 179 | H | —$OCH_3$ | —Scyclopropyl |
| 180 | H | —$OCH_3$ | —Scyclobutyl |
| 181 | H | —$OCH_3$ | —Scyclopentyl |
| 182 | H | —$OCH_3$ | —Scyclohexyl |
| 183 | H | —$OCH_3$ | $NH_2$ |
| 184 | H | —$OCH_3$ | —$NHCH_3$ |
| 185 | H | —$OCH_3$ | —$NHCH_5$ |
| 186 | H | —$OCH_3$ | —$NHC_3H_7$ |
| 187 | H | —$OCH_3$ | —$NHC_4H_9$ |
| 188 | H | —$OCH_3$ | —$NHCH_2CH$═$CH_2$ |
| 189 | H | —$OCH_3$ | —NHPh |
| 190 | H | —$OCH_3$ | —$NHCH_2Ph$ |
| 191 | H | —$OCH_3$ | —NHcyclopropyl |
| 192 | H | —$OCH_3$ | —NHcyclobutyl |
| 193 | H | —$OCH_3$ | —NHcyclopentyl |
| 194 | H | —$OCH_3$ | —NHcyclohexyl |

TABLE B-continued

| No. | $R^3$ | $R^4$ | $R^5$ |
|---|---|---|---|
| 195 | H | —$OCH_3$ | —$N(CH_3)_2$ |
| 196 | H | —$OCH_3$ | —$N(CH_3)(C_2H_5)$ |
| 197 | H | —$OCH_3$ | —$N(C_2H_5)_2$ |
| 198 | H | —$OCH_3$ | —$N(CH_3)(C_3H_7)$ |
| 199 | H | —$OCH_3$ | —$N(CH_3)C_4H_9$ |
| 200 | H | —$OCH_3$ | —$N(CH_3)(CH_2CH{=}CH_2)$ |
| 201 | H | —$OCH_3$ | —$N(CH_3)Ph$ |
| 202 | H | —$OCH_3$ | —$N(C_2H_5)Ph$ |
| 203 | H | —$OCH_3$ | —$N(Ph)_2$ |
| 204 | H | —$OCH_3$ | —$N(C_2H_5)(CH_2Ph)$ |
| 205 | H | —$OCH_3$ | —$N(CH_2Ph)_2$ |
| 208 | H | —$OCH_3$ | —$N(CH_3)(CH_2Ph)$ |
| 207 | H | —$OCH_3$ | —$N(CH_3)$cyclopropyl |
| 208 | H | —$OCH_3$ | —$N(CH_3)$cycobutyl |
| 209 | H | —$OCH_3$ | —$N(CH_3)$cyclopentyl |
| 210 | H | —$OCH_3$ | —$N(CH_3)$cyclohexyl |
| 211 | H | —$OSO_2CH_3$ | H |
| 212 | H | —$OSO_2CH_3$ | —$CH_3$ |
| 213 | H | —$OSO_2CH_3$ | —$C_2H_5$ |
| 214 | H | —$OSO_2CH_3$ | —$C_3H_7$ |
| 215 | H | —$OSO_2CH_3$ | —$C_4H_9$ |
| 216 | H | —$OSO_2CH_3$ | —$CH{=}CH_2$ |
| 217 | H | —$OSO_2CH_3$ | —$CH_2CH{=}CH_2$ |
| 218 | H | —$OSO_2CH_3$ | —$CH_2CH{=}CHPh$ |
| 219 | H | —$OSO_2CH_3$ | —$CH_2CH{=}CHCH_3$ |
| 220 | H | —$OSO_2CH_3$ | —$C{=}CH$ |
| 221 | H | —$OSO_2CH_3$ | —$C{=}CCH_3$ |
| 222 | H | —$OSO_2CH_3$ | —$C{=}CPh$ |
| 223 | H | —$OSO_2CH_3$ | Ph |
| 224 | H | —$OSO_2CH_3$ | —$CH_2Ph$ |
| 225 | H | —$OSO_2CH_3$ | cyclopropyl |
| 226 | H | —$OSO_2CH_3$ | cyclobutyl |
| 227 | H | —$OSO_2CH_3$ | cyclopentyl |
| 228 | H | —$OSO_2CH_3$ | cyclohexyl |
| 229 | H | —$OSO_2CH_3$ | OH |
| 230 | H | —$OSO_2CH_3$ | —$OCH_3$ |
| 231 | H | —$OSO_2CH_3$ | —$OC_2H_5$ |
| 232 | H | —$OSO_2CH_3$ | —$OC_3H_7$ |
| 233 | H | —$OSO_2CH_3$ | —$OC_4H_9$ |
| 234 | H | —$OSO_2CH_3$ | —$OCH_2CH{=}CH_2$ |
| 235 | H | —$OSO_2CH_3$ | —OPh |
| 236 | H | —$OSO_2CH_3$ | —$OCH_2Ph$ |
| 237 | H | —$OSO_2CH_3$ | —Ocyclopropyl |
| 238 | H | —$OSO_2CH_3$ | —Ocyclobutyl |
| 239 | H | —$OSO_2CH_3$ | —Ocyclopentyl |
| 240 | H | —$OSO_2CH_3$ | —Ocyclohexyl |
| 241 | H | —$OSO_2CH_3$ | SH |
| 242 | H | —$OSO_2CH_3$ | —$SCH_3$ |
| 243 | H | —$OSO_2CH_3$ | —$SC_{2H5}$ |
| 244 | H | —$OSO_2CH_3$ | —$SC_3H_7$ |
| 245 | H | —$OSO_2CH_3$ | —$SC_4H_9$ |
| 246 | H | —$OSO_2CH_3$ | —$SCH_2CH{=}CH_2$ |
| 247 | H | —$OSO_2CH_3$ | —SPh |
| 248 | H | —$OSO_2CH_3$ | —$SCH_2Ph$ |
| 249 | H | —$OSO_2CH_3$ | —Scyclopropyl |
| 250 | H | —$OSO_2CH_3$ | —Scyclobutyl |
| 251 | H | —$OSO_2CH_3$ | —Scyclopentyl |
| 252 | H | —$OSO_2CH_3$ | —Scyclohexyl |
| 253 | H | —$OSO_2CH_3$ | $NH_2$ |
| 254 | H | —$OSO_2CH_3$ | —$NHCH_3$ |
| 255 | H | —$OSO_2CH_3$ | —$NHC_2H_5$ |
| 256 | H | —$OSO_2CH_3$ | —$NHC_3H_7$ |
| 257 | H | —$OSO_2CH_3$ | —$NHC_4H_9$ |
| 258 | H | —$OSO_2CH_3$ | —$NHCH_2CH{=}CH_2$ |
| 259 | H | —$OSO_2CH_3$ | —NHPh |
| 260 | H | —$OSO_2CH_3$ | —$NHCH_2Ph$ |
| 261 | H | —$OSO_2CH_3$ | —NHcyclopropyl |
| 262 | H | —$OSO_2CH_3$ | —NHcyclobutyl |
| 263 | H | —$OSO_2CH_3$ | —NHcyclopentyl |
| 264 | H | —$OSO_2CH_3$ | —NHcyclohexyl |
| 265 | H | —$OSO_2CH_3$ | —$N(CH_3)_2$ |
| 266 | H | —$OSO_2CH_3$ | —$N(CH_3)(C_2H_5)$ |
| 267 | H | —$OSO_2CH_3$ | —$N(C_2H_5)_2$ |
| 268 | H | —$OSO_2CH_3$ | —$N(CH_3)(CH_7)$ |
| 269 | H | —$OSO_2CH_3$ | —$N(CH_3)C_4H_9$ |
| 270 | H | —$OSO_2CH_3$ | —$N(CH_3)(CH_2CH{=}CH_2)$ |
| 271 | H | —$OSO_2CH_3$ | —$N(CH_3)Ph$ |

TABLE B-continued

| No. | $R^3$ | $R^4$ | $R^5$ |
|---|---|---|---|
| 272 | H | —$OSO_2CH_3$ | —$N(C_2H_5)Ph$ |
| 273 | H | —$OSO_2CH_3$ | —$N(Ph)_2$ |
| 274 | H | —$OSO_2CH_3$ | —$N(C_2H_5)(CH_2Ph)$ |
| 275 | H | —$OSO_2CH_3$ | —$N(CH_2Ph)_2$ |
| 276 | H | —$OSO_2CH_3$ | —$N(CH_3)(CH_2Ph)$ |
| 277 | H | —$OSO_2CH_3$ | —$N(CH_3)$cyclopropyl |
| 278 | H | —$OSO_2CH_3$ | —$N(CH_3)$cyclobutyl |
| 279 | H | —$OSO_2CH_3$ | —$N(CH_3)$cyclopentyl |
| 280 | H | —$OSO_2CH_3$ | —$N(CH_3)$cyclohexyl |
| 281 | —$CH_3$ | OH | H |
| 282 | —$CH_3$ | OH | —$CH_3$ |
| 283 | —$CH_3$ | OH | —$C_2H_5$ |
| 284 | —$CH_3$ | OH | —$C_3H_7$ |
| 285 | —$CH_3$ | OH | —$C_4H_9$ |
| 286 | —$CH_3$ | OH | —$CH{=}CH_2$ |
| 287 | —$CH_3$ | OH | —$CH_2CH{=}CH_2$ |
| 288 | —$CH_3$ | OH | —$CH_2CH{=}CHPh$ |
| 289 | —$CH_3$ | OH | —$CH_2CH{=}CHCH_3$ |
| 290 | —$CH_3$ | OH | —C—CH |
| 291 | —$CH_3$ | OH | —C—$CCH_3$ |
| 292 | —$CH_3$ | OH | —$C{=}CPh$ |
| 293 | —$CH_3$ | OH | Ph |
| 294 | —$CH_3$ | OH | —$CH_2Ph$ |
| 295 | —$CH_3$ | OH | cyclopropyl |
| 296 | —$CH_3$ | OH | cyclobutyl |
| 297 | —$CH_3$ | OH | cyclopentyl |
| 296 | —$CH_3$ | OH | cyclohexyl |
| 299 | —$CH_3$ | OH | OH |
| 300 | —$CH_3$ | OH | —$OCH_3$ |
| 301 | —$CH_3$ | OH | —$OC_2H_5$ |
| 302 | —$CH_3$ | OH | —$OC_3H_7$ |
| 303 | —$CH_3$ | OH | —$OC_4H_9$ |
| 304 | —$CH_3$ | OH | —$OCH_2CH{=}CH_2$ |
| 305 | —$CH_3$ | OH | —OPh |
| 306 | —$CH_3$ | OH | —$OCH_2Ph$ |
| 307 | —$CH_3$ | OH | —Ocyclopropyl |
| 308 | —$CH_3$ | OH | —Ocyclobutyl |
| 309 | —$CH_3$ | OH | —Ocyclopentyl |
| 310 | —$CH_3$ | OH | —Ocyclohexyl |
| 311 | —$CH_3$ | OH | SH |
| 312 | —$CH_3$ | OH | —$SCH_3$ |
| 313 | —$CH_3$ | OH | —$SC_2H_5$ |
| 314 | —$CH_3$ | OH | —$SC_3H_7$ |
| 315 | —$CH_3$ | OH | —$SC_4H_9$ |
| 316 | —$CH_3$ | OH | —$SCH_2CH$—$CH_2$ |
| 317 | —$CH_3$ | OH | —SPh |
| 318 | —$CH_3$ | OH | —$SCH_2Ph$ |
| 319 | —$CH_3$ | OH | —Scyclopropyl |
| 320 | —$CH_3$ | OH | —Scyclobutyl |
| 321 | —$CH_3$ | OH | —Scyclopentyl |
| 322 | —$CH_3$ | OH | —Scyclohexyl |
| 323 | —$CH_3$ | OH | $NH_2$ |
| 324 | —$CH_3$ | OH | —$NHCH_3$ |
| 325 | —$CH_3$ | OH | —$NHC_2H_5$ |
| 326 | —$CH_3$ | OH | —$NHC_3H_7$ |
| 327 | —$CH_3$ | OH | —$NHC_4H_9$ |
| 328 | —$CH_3$ | OH | —$NHCH_2CH{=}CH_2$ |
| 329 | —$CH_3$ | OH | —NHPh |
| 330 | —$CH_3$ | OH | —$NHCH_2Ph$ |
| 331 | —$CH_3$ | OH | —NHcyclopropyl |
| 332 | —$CH_3$ | OH | —NHcyclobutyl |
| 333 | —$CH_3$ | OH | —NHcyclopentyl |
| 334 | —$CH_3$ | OH | —NHcyclohexyl |
| 335 | —$CH_3$ | OH | —$N(CH_3)_2$ |
| 336 | —$CH_3$ | OH | —$N(CH_3)(C_2H_5)$ |
| 337 | —$CH_3$ | OH | —$N(C_2H_5)_2$ |
| 338 | —$CH_3$ | OH | —$N(CH_3)(C_3H_7)$ |
| 339 | —$CH_3$ | OH | —$N(CH_3)C_4H_9$ |
| 340 | —$CH_3$ | OH | —$N(CH_3)(CH_2CH{=}CH_2)$ |
| 341 | —$CH_3$ | OH | —$N(CH_3)Ph$ |
| 342 | —$CH_3$ | OH | —$N(C_2H_5)Ph$ |
| 343 | —$CH_3$ | OH | —$N(Ph)_2$ |
| 344 | —$CH_3$ | OH | —$N(C_2H_5)(CH_2Ph)$ |
| 345 | —$CH_3$ | OH | —$N(CH_2Ph)_2$ |
| 346 | —$CH_3$ | OH | —$N(CH_3)(CH_2Ph)$ |
| 347 | —$CH_3$ | OH | —$N(CH_3)$cyclopropyl |
| 348 | —$CH_3$ | OH | —$N(CH_3)$cyclobutyl |

TABLE B-continued

| No. | R$^3$ | R$^4$ | R$^5$ |
|---|---|---|---|
| 349 | —CH$_3$ | OH | —N(CH$_3$)cyclopentyl |
| 350 | —CH$_3$ | OH | —N(CH$_3$)cyclohexyl |
| 351 | H | OH | H |
| 352 | H | OH | —CH$_3$ |
| 353 | H | OH | —C$_2$H$_5$ |
| 354 | H | OH | —C$_3$H$_7$ |
| 355 | H | OH | —C$_4$H$_9$ |
| 356 | H | OH | —CH═CH$_2$ |
| 357 | H | OH | —CH$_2$CH═CH$_2$ |
| 358 | H | OH | —CH$_2$CH═CHPh |
| 359 | H | OH | —CH$_2$CH═CHCH$_3$ |
| 360 | H | OH | —C═CH |
| 361 | H | OH | —C═CCH$_3$ |
| 362 | H | OH | —C═CPh |
| 363 | H | OH | Ph |
| 364 | H | OH | —CH$_2$Ph |
| 365 | H | OH | cyclopropyl |
| 366 | H | OH | cyclobutyl |
| 367 | H | OH | cyclopentyl |
| 368 | H | OH | cyclohexyl |
| 369 | H | OH | OH |
| 370 | H | OH | —OCH$_3$ |
| 371 | H | OH | —OC$_2$H$_5$ |
| 372 | H | OH | —OC$_3$H$_7$ |
| 373 | H | OH | —OC$_4$H$_9$ |
| 374 | H | OH | —OCH$_2$CH═CH$_2$ |
| 375 | H | OH | —OPh |
| 376 | H | OH | —OCH$_2$Ph |
| 377 | H | OH | —Ocyclopropyl |
| 378 | H | OH | —Ocyclobutyl |
| 379 | H | OH | —Ocyclopentyl |
| 380 | H | OH | —Ocyclohexyl |
| 381 | H | OH | SH |
| 382 | H | OH | —SCH$_3$ |
| 383 | H | OH | —SC$_2$H$_5$ |
| 384 | H | OH | —SC$_3$H$_7$ |
| 385 | H | OH | —SC$_4$H$_9$ |
| 386 | H | OH | —SCH$_2$CH═CH$_2$ |
| 387 | H | OH | —SPh |
| 388 | H | OH | —SCH$_2$Ph |
| 389 | H | OH | —Scyclopropyl |
| 390 | H | OH | —Scyclobutyl |
| 391 | H | OH | —Scyclopentyl |
| 392 | H | OH | —Scyclohexyl |
| 393 | H | OH | NH$_2$ |
| 394 | H | OH | —NHCH$_3$ |
| 395 | H | OH | —NHC$_2$H$_5$ |
| 396 | H | OH | —NHC$_3$H$_7$ |
| 397 | H | OH | —NHC$_4$H$_9$ |
| 398 | H | OH | —NHCH$_2$CH═CH$_2$ |
| 399 | H | OH | —NHPh |
| 400 | H | OH | —NHCH$_2$Ph |
| 401 | H | OH | —NHcyclopropyl |
| 402 | H | OH | —NHcyclobutyl |
| 403 | H | OH | —NHcyclopentyl |
| 404 | H | OH | —NHcyclohexyl |
| 405 | H | OH | —N(CH$_3$)$_2$ |
| 406 | H | OH | —N(CH$_3$)(C$_2$H$_5$) |
| 407 | H | OH | —N(C$_2$H$_5$)$_2$ |
| 408 | H | OH | —N(CH$_3$)(C$_3$H$_7$) |
| 409 | H | OH | —N(CH$_3$)C$_4$H$_9$ |
| 410 | H | OH | —N(CH$_3$)(CH$_2$CH—CH$_2$) |
| 411 | H | OH | —N(CH$_3$)Ph |
| 412 | H | OH | —N(C$_2$H$_5$)Ph |
| 413 | H | OH | —N(Ph)$_2$ |
| 414 | H | OH | —N(C$_2$H$_5$)(CH$_2$Ph) |
| 415 | H | OH | —N(CH$_2$Ph)$_2$ |
| 416 | H | OH | —N(CH$_3$)(CH$_2$Ph) |
| 417 | H | OH | —N(CH$_3$)cyclopropyl |
| 418 | H | OH | —N(CH$_3$)cyclobutyl |
| 419 | H | OH | —N(CH$_3$)cyclopentyl |
| 420 | H | OH | —N(CH$_3$)cyclohexyl |
| 421 | H | OH | H |
| 422 | H | OH | —CH$_3$ |
| 423 | H | OH | —C$_2$H$_5$ |
| 424 | H | OH | —C$_3$H$_7$ |
| 425 | H | OH | —C$_4$H$_9$ |

TABLE B-continued

| No. | R$^3$ | R$^4$ | R$^5$ |
|---|---|---|---|
| 426 | H | OH | —CH═CH$_2$ |
| 427 | H | OH | —CH$_2$CH═CH$_2$ |
| 428 | H | OH | —CH$_2$CH═CHPh |
| 429 | H | OH | —CH$_2$CH═CHCH$_3$ |
| 430 | H | OH | —C═CH |
| 431 | H | OH | —C═CCH$_3$ |
| 432 | H | OH | —C═CPh |
| 433 | H | OH | Ph |
| 434 | H | OH | —CH$_2$Ph |
| 435 | H | OH | cyclopropyl |
| 436 | H | OH | cyclobutyl |
| 437 | H | OH | cyclopentyl |
| 438 | H | OH | cyclohexyl |
| 439 | H | OH | OH |
| 440 | H | OH | —OCH$_3$ |
| 441 | H | OH | —OC$_2$H$_5$ |
| 442 | H | OH | —OC$_3$H$_7$ |
| 443 | H | OH | —OC$_4$H$_9$ |
| 444 | H | OH | —OCH$_2$CH═CH$_2$ |
| 445 | H | OH | —OPh |
| 446 | H | OH | —OCH$_2$Ph |
| 447 | H | OH | —Ocyclopropyl |
| 448 | H | OH | —Ocyclobutyl |
| 449 | H | OH | —Ocyclopentyl |
| 450 | H | OH | —Ocyclohexyl |
| 451 | H | OH | SH |
| 452 | H | OH | —SCH$_3$ |
| 453 | H | OH | —SC$_2$H$_5$ |
| 454 | H | OH | —SC$_3$H$_7$ |
| 455 | H | OH | —SC$_4$H$_9$ |
| 456 | H | OH | —SCH$_2$CH═CH$_2$ |
| 457 | H | OH | —SPh |
| 458 | H | OH | —SCH$_2$Ph |
| 459 | H | OH | —Scyclopropyl |
| 460 | H | OH | —Scyclobutyl |
| 461 | H | OH | —Scyclopentyl |
| 462 | H | OH | —Scyclohexyl |
| 463 | H | OH | NH$_2$ |
| 464 | H | OH | —NHCH$_3$ |
| 465 | H | OH | —NHC$_2$H$_5$ |
| 466 | H | OH | —NHC$_3$H$_7$ |
| 467 | H | OH | —NHC$_4$H$_9$ |
| 468 | H | OH | —NHCH$_2$CH═CH$_2$ |
| 469 | H | OH | —NHPh |
| 470 | H | OH | —NHCH$_2$Ph |
| 471 | H | OH | —NHcyclopropyl |
| 472 | H | OH | —NHcyclobutyl |
| 473 | H | OH | —NHcyclopentyl |
| 474 | H | OH | —NHcyclohexyl |
| 475 | H | OH | —N(CH$_3$)$_2$ |
| 476 | H | OH | —N(CH$_3$)(C$_2$H$_5$) |
| 477 | H | OH | —N(C$_2$H$_5$)$_2$ |
| 478 | H | OH | —N(CH$_3$)(C$_3$H$_7$) |
| 479 | H | OH | —N(CH$_3$)C$_4$H$_9$ |
| 480 | H | OH | —N(CH$_3$)(CH$_2$CH═CH$_2$) |
| 481 | H | OH | —N(CH$_3$)Ph |
| 482 | H | OH | —N(C$_2$H$_5$)Ph |
| 483 | H | OH | —N(Ph)$_2$ |
| 484 | H | OH | —N(C$_2$H$_5$)(CH$_2$Ph) |
| 485 | H | OH | —N(CH$_2$Ph)$_2$ |
| 486 | H | OH | —N(CH$_3$)(CH$_2$Ph) |
| 487 | H | OH | —N(CH$_3$)cyclopropyl |
| 488 | H | OH | —N(CH$_3$)cyclobutyl |
| 489 | H | OH | —N(CH$_3$)cyclopentyl |
| 490 | H | OH | —N(CH$_3$)cyclohexyl |
| 491 | H | H | —OCH$_2$CH$_2$— |
| 492 | CH$_3$ | H | —OCH$_2$CH$_2$— |
| 493 | H | H | —CH$_2$CH$_2$O— |
| 494 | CH$_3$ | H | —CH$_2$CH$_2$O— |
| 495 | H | H | —OCH═CH— |
| 496 | CH$_3$ | H | —OCH═CH— |
| 497 | H | H | —CH═CHO— |
| 498 | CH$_3$ | H | —CH═CHO— |
| 499 | H | H | —OCH$_2$CH$_2$CH$_2$— |
| 500 | CH$_3$ | H | —OCH$_2$CH$_2$CH$_2$— |
| 501 | H | H | —CH$_2$CH$_2$CH$_2$O— |
| 502 | CH$_3$ | H | —CH$_2$CH$_2$CH$_2$O— |

TABLE B-continued

| No. | $R^3$ | $R^4$ | $R^5$ |
|---|---|---|---|
| 503 | H | H | —$NHCH_2CH_2$— |
| 504 | $CH_3$ | H | —$NHCH_2CH_2$— |
| 505 | H | H | —$CH_2CH_2NH$— |
| 506 | $CH_3$ | H | —$CH_2CH_2NH$— |
| 507 | H | H | —NHCH═CH— |
| 508 | $CH_3$ | H | —NHCH═CH— |
| 509 | H | H | —CH═CHNH— |
| 510 | $CH_3$ | H | —CH═CHNH— |
| 511 | H | H | —$NHCH_2CH_2CH_2$— |
| 512 | $CH_3$ | H | —$NHCH_2CH_2CH_2$— |
| 513 | H | H | —$CH_2CH_2CH_2NH$— |
| 514 | $CH_3$ | H | —$CH_2CH_2CH_2NH$— |

The Tables 145–288 below are based on the 4-benzoylpyrazoles of the formula Ic:

Ic

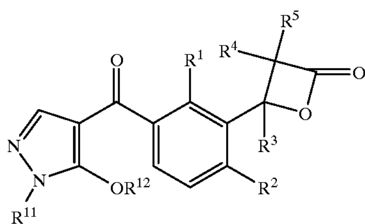

Table 145: Compounds 145.1–145.514

Compounds of the general formula Ic, where $R^1$ is Cl, $R^2$ is methylsulfonyl, $R^{11}$ is methyl and $R^{12}$ is hydrogen and where for each individual compound the substituents $R^3$–$R^5$ correspond to one line of Table B.

Table 146: Compounds 146.1–146.514

Compounds of the general formula Ic, where $R^1$ is Cl, $R^2$ is methylsulfonyl, $R^{11}$ is ethyl, $R^{12}$ is hydrogen and where for each individual compound the substituents $R^3$–$R^5$ correspond to one line of Table B.

Table 147: Compounds 147.1–147.514

Compounds of the general formula Ic, where $R^1$ is Cl, $R^2$ is methylsulfonyl, $R^{11}$ is n-propyl, $R^{12}$ is hydrogen and where for each individual compound the substituents $R^3$–$R^5$ correspond to one line of Table B.

Table 148: Compounds 148.1–148.514

Compounds of the general formula Ic, where $R^1$ is Cl, $R^2$ is methylsulfonyl, $R^{11}$ is methyl, $R^{12}$ is methyl and where for each individual compound the substituents $R^3$–$R^5$ correspond to one line of Table B.

Table 149: Compounds 149.1–149.514

Compounds of the general formula Ic, where $R^1$ is Cl, $R^2$ is methylsulfonyl, $R^{11}$ is ethyl, $R^{12}$ is methyl and where for each individual compound the substituents $R^3$–$R^5$ correspond to one line of Table B.

Table 150: Compounds 150.1–150.514

Compounds of the general formula Ic, where $R^1$ is Cl, $R^2$ is methylsulfonyl, $R^{11}$ is n-propyl, $R^{12}$ is methyl and where for each individual compound the substituents $R^3$–$R^5$ correspond to one line of Table B.

Table 151: Compounds 151.1–151.514

Compounds of the general formula Ic, where $R^1$ is Cl, $R^2$ is methylsulfonyl, $R^{11}$ is methyl, $R^{12}$ is ethyl and where for each individual compound the substituents $R^3$–$R^5$ correspond to one line of Table B.

Table 152: Compounds 152.1–152.514

Compounds of the general formula Ic, where $R^1$ is Cl, $R^2$ is methylsulfonyl, $R^{11}$ is ethyl, $R^{12}$ is ethyl and where for each individual compound the substituents $R^3$–$R^5$ correspond to one line of Table B.

Table 153: Compounds 153.1–153.514

Compounds of the general formula Ic, where $R^1$ is Cl, $R^2$ is methylsulfonyl, $R^{11}$ is n-propyl, $R^{12}$ is ethyl and where for each individual compound the substituents $R^3$–$R^5$ correspond to one line of Table B.

Table 154: Compounds 154.1–154.514

Compounds of the general formula Ic, where $R^1$ is Cl, $R^2$ is methylsulfonyl, $R^{11}$ is methyl, $R^{12}$ is methylcarbonyl and where for each individual compound the substituents $R^3$–$R^5$ correspond to one line of Table B.

Table 155: Compounds 155.1–155.514

Compounds of the general formula Ic, where $R^1$ is Cl, $R^2$ is methylsulfonyl, $R^{11}$ is ethyl, $R^{12}$ is methylcarbonyl and where for each individual compound the substituents $R^3$–$R^5$ correspond to one line of Table B.

Table 156: Compounds 156.1–156.514

Compounds of the general formula Ic, where $R^1$ is Cl, $R^2$ is methylsulfonyl, $R^{11}$ is n-propyl, $R^{12}$ is methylcarbonyl and where for each individual compound the substituents $R^3$–$R^5$ correspond to one line of Table B.

Table 157: Compounds 157.1–157.514

Compounds of the general formula Ic, where $R^1$ is Cl, $R^2$ is methylsulfonyl, $R^{11}$ is methyl, $R^{12}$ is ethylcarbonyl and where for each individual compound the substituents $R^3$–$R^5$ correspond to one line of Table B.

Table 158: Compounds 158.1–158.514

Compounds of the general formula Ic, where $R^1$ is Cl, $R^2$ is methylsulfonyl, $R^{11}$ is ethyl, $R^{12}$ is ethylcarbonyl and where for each individual compound the substituents $R^3$–$R^5$ correspond to one line of Table B.

Table 159: Compounds 159.1–159.514

Compounds of the general formula Ic, where $R^1$ is Cl, $R^2$ is methylsulfonyl, $R^{11}$ is n-propyl, $R^{12}$ is ethylcarbonyl and where for each individual compound the substituents $R^3$–$R^5$ correspond to one line of Table B.

Table 160: Compounds 160.1–160.514

Compounds of the general formula Ic, where $R^1$ is Cl, $R^2$ is methylsulfonyl, $R^{11}$ is methyl, $R^{12}$ is methylsulfonyl and where for each individual compound the substituents $R^3$–$R^5$ correspond to one line of Table B.

Table 161: Compounds 161.1–161.514

Compounds of the general formula Ic, where $R^1$ is Cl, $R^2$ is methylsulfonyl, $R^{11}$ is ethyl, $R^{12}$ is methylsulfonyl and where for each individual compound the substituents $R^3$–$R^5$ correspond to one line of Table B.

Table 162: Compounds 162.1–162.514

Compounds of the general formula Ic, where $R^1$ is Cl, $R^2$ is methylsulfonyl, $R^{11}$ is n-propyl, $R^{12}$ is methylsulfonyl and where for each individual compound the substituents $R^3$–$R^5$ correspond to one line of Table B.

Table 163: Compounds 163.1–163.514

Compounds of the general formula Ic, where $R^1$ is Cl, $R^2$ is methylsulfonyl, $R^{11}$ is methyl, $R^{12}$ is ethylsulfonyl and where for each individual compound the substituents $R^3$–$R^5$ correspond to one line of Table B.

Table 164: Compounds 164.1–164.514

Compounds of the general formula Ic, where $R^1$ is Cl, $R^2$ is methylsulfonyl, $R^{11}$ is ethyl, $R^{12}$ is ethylsulfonyl and where for each individual compound the substituents $R^3$–$R^5$ correspond to one line of Table B.

Table 165: Compounds 165.1–165.514

Compounds of the general formula Ic, where $R^1$ is Cl, $R^2$ is methylsulfonyl, $R^{11}$ is n-propyl, $R^{12}$ is ethylsulfonyl and where for each individual compound the substituents $R^3$–$R^5$ correspond to one line of Table B.

Table 166: Compounds 166.1–166.514

Compounds of the general formula Ic, where $R^1$ is Cl, $R^2$ is methylsulfonyl, $R^{11}$ is methyl, $R^{12}$ is 4-methylphenylsulfonyl and where for each individual compound the substituents $R^3$–$R^5$ correspond to one line of Table B.

Table 167: Compounds 167.1–167.514

Compounds of the general formula Ic, where $R^1$ is Cl, $R^2$ is methylsulfonyl, $R^{11}$ is ethyl, $R^{12}$ is 4-methylphenylsulfonyl and where for each individual compound the substituents $R^3$–$R^5$ correspond to one line of Table B.

Table 168: Compounds 168.1–168.514

Compounds of the general formula Ic, where $R^1$ is Cl, $R^2$ is methylsulfonyl, $R^{11}$ is n-propyl, $R^{12}$ is 4-methylphenylsulfonyl and where for each individual compound the substituents $R^3$–$R^5$ correspond to one line of Table B.

Table 169: Compounds 169.1–160.514

Compounds of the general formula Ic, where $R^1$ is Cl, $R^2$ is Cl, $R^{11}$ is methyl and $R^{12}$ is hydrogen and where for each individual compound the substituents $R^3$–$R^5$ correspond to one line of Table B.

Table 170: Compounds 170.1–170.514

Compounds of the general formula Ic, where $R^1$ is Cl, $R^2$ is Cl, $R^{11}$ is ethyl, $R^{12}$ is hydrogen and where for each individual compound the substituents $R^3$–$R^5$ correspond to one line of Table B.

Table 171: Compounds 171.1–171.514

Compounds of the general formula Ic, where $R^1$ is Cl, $R^2$ is Cl, $R^{11}$ is n-propyl, $R^{12}$ is hydrogen and where for each individual compound the substituents $R^3$–$R^5$ correspond to one line of Table B.

Table 172: Compounds 172.1–172.514

Compounds of the general formula Ic, where $R^1$ is Cl, $R^2$ is Cl, $R^{11}$ is methyl, $R^{12}$ is methyl and where for each individual compound the substituents $R^3$–$R^5$ correspond to one line of Table B.

Table 173: Compounds 173.1–173.514

Compounds of the general formula Ic, where $R^1$ is Cl, $R^2$ is Cl, $R^{11}$ is ethyl, $R^{12}$ is methyl and where for each individual compound the substituents $R^3$–$R^5$ correspond to one line of Table B.

Table 174: Compounds 174.1–174.514

Compounds of the general formula Ic, where $R^1$ is Cl, $R^2$ is Cl, $R^{11}$ is n-propyl, $R^{12}$ is methyl and where for each individual compound the substituents $R^3$–$R^5$ correspond to one line of Table B.

Table 175: Compounds 175.1–175.514

Compounds of the general formula Ic, where $R^1$ is Cl, $R^2$ is Cl, $R^{11}$ is methyl, $R^{12}$ is ethyl and where for each individual compound the substituents $R^3$–$R^5$ correspond to one line of Table B.

Table 176: Compounds 176.1–176.514

Compounds of the general formula Ic, where $R^1$ is Cl, $R^2$ is Cl, $R^{11}$ is ethyl, $R^{12}$ is ethyl and where for each individual compound the substituents $R^3$–$R^5$ correspond to one line of Table B.

Table 177: Compounds 177.1–177.514

Compounds of the general formula Ic, where $R^1$ is Cl, $R^2$ is Cl, $R^{11}$ is n-propyl, $R^{12}$ is ethyl and where for each individual compound the substituents $R^3$–$R^5$ correspond to one line of Table B.

Table 178: Compounds 178.1–178.514

Compounds of the general formula Ic, where $R^1$ is Cl, $R^2$ is Cl, $R^{11}$ is methyl, $R^{12}$ is methylcarbonyl and where for each individual compound the substituents $R^3$–$R^5$ correspond to one line of Table B.

Table 179: Compounds 179.1–179.514

Compounds of the general formula Ic, where $R^1$ is Cl, $R^2$ is Cl, $R^{11}$ is ethyl, $R^{12}$ is methylcarbonyl and where for each individual compound the substituents $R^3$–$R^5$ correspond to one line of Table B.

Table 180: Compounds 180.1–180.514

Compounds of the general formula Ic, where $R^1$ is Cl, $R^2$ is Cl, $R^{11}$ is n-propyl, $R^{12}$ is methylcarbonyl and where for each individual compound the substituents $R^3$–$R^5$ correspond to one line of Table B.

Table 181: Compounds 181.1–181.514

Compounds of the general formula Ic, where $R^1$ is Cl, $R^2$ is Cl, $R^{11}$ is methyl, $R^{12}$ is ethylcarbonyl and where for each individual compound the substituents $R^3$–$R^5$ correspond to one line of Table B.

Table 182: Compounds 182.1–182.514

Compounds of the general formula Ic, where $R^1$ is Cl, $R^2$ is Cl, $R^{11}$ is ethyl, $R^{12}$ is ethylcarbonyl and where for each individual compound the substituents $R^3$–$R^5$ correspond to one line of Table B.

Table 183: Compounds 183.1–183.514

Compounds of the general formula Ic, where $R^1$ is Cl, $R^2$ is Cl, $R^{11}$ is n-propyl, $R^{12}$ is ethylcarbonyl and where for each individual compound the substituents $R^3$–$R^5$ correspond to one line of Table B.

Table 184: Compounds 184.1–184.514

Compounds of the general formula Ic, where $R^1$ is Cl, $R^2$ is Cl, $R^{11}$ is methyl, $R^{12}$ is methylsulfonyl and where for each individual compound the substituents $R^3$–$R^5$ correspond to one line of Table B.

Table 185: Compounds 185.1–185.514

Compounds of the general formula Ic, where $R^1$ is Cl, $R^2$ is Cl, $R^{11}$ is ethyl, $R^{12}$ is methylsulfonyl and where for each individual compound the substituents $R^3$–$R^5$ correspond to one line of Table B.

Table 186: Compounds 186.1–186.514

Compounds of the general formula Ic, where $R^1$ is Cl, $R^2$ is Cl, $R^{11}$ is n-propyl, $R^{12}$ is methylsulfonyl and where for each individual compound the substituents $R^3$–$R^5$ correspond to one line of Table B.

Table 187: Compounds 187.1–187.514

Compounds of the general formula Ic, where $R^1$ is Cl, $R^2$ is Cl, $R^{11}$ is methyl, $R^{12}$ is ethylsulfonyl and where for each individual compound the substituents $R^3$–$R^5$ correspond to one line of Table B.

Table 188: Compounds 188.1–188.514

Compounds of the general formula Ic, where $R^1$ is Cl, $R^2$ is Cl, $R^{11}$ is ethyl, $R^{12}$ is ethylsulfonyl and where for each individual compound the substituents $R^3$–$R^5$ correspond to one line of Table B.

Table 189: Compounds 189.1–189.514

Compounds of the general formula Ic, where $R^1$ is Cl, $R^2$ is Cl, $R^{11}$ is n-propyl, $R^{12}$ is ethylsulfonyl and where for each individual compound the substituents $R^3$–$R^5$ correspond to one line of Table B.

Table 190: Compounds 190.1–190.514

Compounds of the general formula Ic, where $R^1$ is Cl, $R^2$ is Cl, $R^{11}$ is methyl, $R^{12}$ is 4-methylphenylsulfonyl and where for each individual compound the substituents $R^3$–$R^5$ correspond to one line of Table B.

Table 191: Compounds 191.1–191.514

Compounds of the general formula Ic, where $R^1$ is Cl, $R^2$ is Cl, $R^{11}$ is ethyl, $R^{12}$ is 4-methylphenylsulfonyl and where for each individual compound the substituents $R^3$–$R^5$ correspond to one line of Table B.

Table 192: Compounds 192.1–192.514

Compounds of the general formula Ic, where $R^1$ is Cl, $R^2$ is Cl, $R^{11}$ is n-propyl, $R^{12}$ is 4-methylphenylsulfonyl and where for each individual compound the substituents $R^3$–$R^5$ correspond to one line of Table B.

Table 193: Compounds 193.1–193.514

Compounds of the general formula Ic, where $R^1$ is Cl, $R^2$ is trifluoromethyl, $R^{11}$ is methyl and $R^{12}$ is hydrogen and where for each individual compound the substituents $R^3$–$R^5$ correspond to one line of Table B.

Table 194: Compounds 194.1–194.514

Compounds of the general formula Ic, where $R^1$ is Cl, $R^2$ is trifluoromethyl, $R^{11}$ is ethyl, $R^{12}$ is hydrogen and where for each individual compound the substituents $R^3$–$R^5$ correspond to one line of Table B.

Table 195: Compounds 195.1–195.514

Compounds of the general formula Ic, where $R^1$ is Cl, $R^2$ is trifluoromethyl, $R^{11}$ is n-propyl, $R^{12}$ is hydrogen and where for each individual compound the substituents $R^3$–$R^5$ correspond to one line of Table B.

Table 196: Compounds 196.1–196.514

Compounds of the general formula Ic, where $R^1$ is Cl, $R^2$ is trifluoromethyl, $R^{11}$ is methyl, $R^{12}$ is methyl and where for each individual compound the substituents $R^3$–$R^5$ correspond to one line of Table B.

Table 197: Compounds 197.1–197.514

Compounds of the general formula Ic, where $R^1$ is Cl, $R^2$ is trifluoromethyl, $R^{11}$ is ethyl, $R^{12}$ is methyl and where for each individual compound the substituents $R^3$–$R^5$ correspond to one line of Table B.

Table 198: Compounds 198.1–198.514

Compounds of the general formula Ic, where $R^1$ is Cl, $R^2$ is trifluoromethyl, $R^{11}$ is n-propyl, $R^{12}$ is methyl and where for each individual compound the substituents $R^3$–$R^5$ correspond to one line of Table B.

Table 199: Compounds 199.1–199.514

Compounds of the general formula Ic, where $R^1$ is Cl, $R^2$ is trifluoromethyl, $R^{11}$ is methyl, $R^{12}$ is ethyl and where for each individual compound the substituents $R^3$–$R^5$ correspond to one line of Table B.

Table 200: Compounds 200.1–200.514

Compounds of the general formula Ic, where $R^1$ is Cl, $R^2$ is trifluoromethyl, $R^{11}$ is ethyl, $R^{12}$ is ethyl and where for each individual compound the substituents $R^3$–$R^5$ correspond to one line of Table B.

Table 201: Compounds 201.1–201.514

Compounds of the general formula Ic, where $R^1$ is Cl, $R^2$ is trifluoromethyl, $R^{11}$ is n-propyl, $R^{12}$ is ethyl and where for each individual compound the substituents $R^3$–$R^5$ correspond to one line of Table B.

Table 202: Compounds 202.1–202.514

Compounds of the general formula Ic, where $R^1$ is Cl, $R^2$ is trifluoromethyl, $R^{11}$ is methyl, $R^{12}$ is methylcarbonyl and where for each individual compound the substituents $R^3$–$R^5$ correspond to one line of Table B.

Table 203: Compounds 203.1–203.514

Compounds of the general formula Ic, where $R^1$ is Cl, $R^2$ is trifluoromethyl, $R^{11}$ is ethyl, $R^{12}$ is methylcarbonyl and where for each individual compound the substituents $R^3$–$R^5$ correspond to one line of Table B.

Table 204: Compounds 204.1–204.514

Compounds of the general formula Ic, where $R^1$ is Cl, $R^2$ is trifluoromethyl, $R^{11}$ is n-propyl, $R^{12}$ is methylcarbonyl and where for each individual compound the substituents $R^3$–$R^5$ correspond to one line of Table B.

Table 205: Compounds 205.1–205.514

Compounds of the general formula Ic, where $R^1$ is Cl, $R^2$ is trifluoromethyl, $R^{11}$ is methyl, $R^{12}$ is ethylcarbonyl and where for each individual compound the substituents $R^3$–$R^5$ correspond to one line of Table B.

Table 206: Compounds 206.1–206.514

Compounds of the general formula Ic, where $R^1$ is Cl, $R^2$ is trifluoromethyl, $R^{11}$ is ethyl, $R^{12}$ is ethylcarbonyl and where for each individual compound the substituents $R^3$–$R^5$ correspond to one line of Table B.

Table 207: Compounds 207.1–207.514

Compounds of the general formula Ic, where $R^1$ is Cl, $R^2$ is trifluoromethyl, $R^{11}$ is n-propyl, $R^{12}$ is ethylcarbonyl and where for each individual compound the substituents $R^3$–$R^5$ correspond to one line of Table B.

Table 208: Compounds 208.1–208.514

Compounds of the general formula Ic, where $R^1$ is Cl, $R^2$ is trifluoromethyl, $R^{11}$ is methyl, $R^{12}$ is methylsulfonyl and where for each individual compound the substituents $R^3$–$R^5$ correspond to one line of Table B.

Table 209: Compounds 209.1–209.514

Compounds of the general formula Ic, where $R^1$ is Cl, $R^2$ is trifluoromethyl, $R^{11}$ is ethyl, $R^{12}$ is methylsulfonyl and where for each individual compound the substituents $R^3$–$R^5$ correspond to one line of Table B.

Table 210: Compounds 210.1–210.514

Compounds of the general formula Ic, where $R^1$ is Cl, $R^2$ is trifluoromethyl, $R^{11}$ is n-propyl, $R^{12}$ is methylsulfonyl and where for each individual compound the substituents $R^3$–$R^5$ correspond to one line of Table B.

Table 211: Compounds 211.1–211.514

Compounds of the general formula Ic, where $R^1$ is Cl, $R^2$ is trifluoromethyl, $R^{11}$ is methyl, $R^{12}$ is ethylsulfonyl and where for each individual compound the substituents $R^3$–$R^5$ correspond to one line of Table B.

Table 212: Compounds 212.1–212.514

Compounds of the general formula Ic, where $R^1$ is Cl, $R^2$ is trifluoromethyl, $R^{11}$ is ethyl, $R^{12}$ is ethylsulfonyl and where for each individual compound the substituents $R^3$–$R^5$ correspond to one line of Table B.

Table 213: Compounds 213.1–213.514

Compounds of the general formula Ic, where $R^1$ is Cl, $R^2$ is trifluoromethyl, $R^{11}$ is n-propyl, $R^{12}$ is ethylsulfonyl and where for each individual compound the substituents $R^3$–$R^5$ correspond to one line of Table B.

Table 214: Compounds 214.1–214.514

Compounds of the general formula Ic, where $R^1$ is Cl, $R^2$ is trifluoromethyl, $R^{11}$ is methyl, $R^{12}$ is 4-methylphenylsulfonyl and where for each individual compound the substituents $R^3$–$R^5$ correspond to one line of Table B.

Table 215: Compounds 215.1–215.514

Compounds of the general formula Ic, where $R^1$ is Cl, $R^2$ is trifluoromethyl, $R^{11}$ is ethyl, $R^{12}$ is 4-methylphenylsulfonyl and where for each individual compound the substituents $R^1$–$R^5$ correspond to one line of Table B.

Table 216: Compounds 216.1–216.514

Compounds of the general formula Ic, where $R^1$ is Cl, $R^2$ is trifluoromethyl, $R^{11}$ is n-propyl, $R^{12}$ is 4-methylphenylsulfonyl and where for each individual compound the substituents $R^3$–$R^5$ correspond to one line of Table B.

Table 217: Compounds 217.1–217.514

Compounds of the general formula Ic, where $R^1$ is methyl, $R^2$ is Cl, $R^{11}$ is methyl and $R^{12}$ is hydrogen and where for each individual compound the substituents $R^3$–$R^5$ correspond to one line of Table B.

Table 218: Compounds 218.1–218.514

Compounds of the general formula Ic, where $R^1$ is methyl, $R^2$ is Cl, $R^{11}$ is ethyl, $R^{12}$ is hydrogen and where for each individual compound the substituents $R^3$–$R^5$ correspond to one line of Table B.

Table 219: Compounds 219.1–219.514

Compounds of the general formula Ic, where $R^1$ is methyl, $R^2$ is Cl, $R^{11}$ is n-propyl, $R^{12}$ is hydrogen and where for each individual compound the substituents $R^3$–$R^5$ correspond to one line of Table B.

Table 220: Compounds 220.1–220.514

Compounds of the general formula Ic, where $R^1$ is methyl, $R^2$ is Cl, $R^{11}$ is methyl, $R^{12}$ is methyl and where for each individual compound the substituents $R^3$–$R^5$ correspond to one line of Table B.

Table 221: Compounds 221.1–221.514

Compounds of the general formula Ic, where $R^1$ is methyl, $R^2$ is Cl, $R^{11}$ is ethyl, $R^{12}$ is methyl and where for each individual compound the substituents $R^3$–$R^5$ correspond to one line of Table B.

Table 222: Compounds 222.1–222.514

Compounds of the general formula Ic, where $R^1$ is methyl, $R^2$ is Cl, $R^{11}$ is n-propyl, $R^{12}$ is methyl and where for each individual compound the substituents $R^3$–$R^5$ correspond to one line of Table B.

Table 223: Compounds 223.1–223.514

Compounds of the general formula Ic, where $R^1$ is methyl, $R^2$ is Cl, $R^{11}$ is methyl, $R^{12}$ is ethyl and where for each individual compound the substituents $R^3$–$R^5$ correspond to one line of Table B.

Table 224: Compounds 224.1–224.514

Compounds of the general formula Ic, where $R^1$ is methyl, $R^2$ is Cl, $R^{11}$ is ethyl, $R^{12}$ is ethyl and where for each individual compound the substituents $R^3$–$R^5$ correspond to one line of Table B.

Table 225: Compounds 225.1–225.514

Compounds of the general formula Ic, where $R^1$ is methyl, $R^2$ is Cl, $R^{11}$ is n-propyl, $R^{12}$ is ethyl and where for each individual compound the substituents $R^3$–$R^5$ correspond to one line of Table B.

Table 226: Compounds 226.1–226.514

Compounds of the general formula Ic, where $R^1$ is methyl, $R^2$ is Cl, $R^{11}$ is methyl, $R^{12}$ is methylcarbonyl and where for each individual compound the substituents $R^3$–$R^5$ correspond to one line of Table B.

Table 227: Compounds 227.1–227.514

Compounds of the general formula Ic, where $R^1$ is methyl, $R^2$ is Cl, $R^{11}$ is ethyl, $R^{12}$ is methylcarbonyl and where for each individual compound the substituents $R^3$–$R^5$ correspond to one line of Table B.

Table 228: Compounds 228.1–228.514

Compounds of the general formula Ic, where $R^1$ is methyl, $R^2$ is Cl, $R^{11}$ is n-propyl, $R^{12}$ is methylcarbonyl and where for each individual compound the substituents $R^3$–$R^5$ correspond to one line of Table B.

Table 229: Compounds 229.1–229.514

Compounds of the general formula Ic, where $R^1$ is methyl, $R^2$ is Cl, $R^{11}$ is methyl, $R^{12}$ is ethylcarbonyl and where for each individual compound the substituents $R^3$–$R^5$ correspond to one line of Table B.

Table 230: Compounds 230.1–230.514

Compounds of the general formula Ic, where $R^1$ is methyl, $R^2$ is Cl, $R^{11}$ is ethyl, $R^{12}$ is ethylcarbonyl and where for each individual compound the substituents $R^3$–$R^5$ correspond to one line of Table B.

Table 231: Compounds 231.1–231.514

Compounds of the general formula Ic, where $R^1$ is methyl, $R^2$ is Cl, $R^{11}$ is n-propyl, $R^{12}$ is ethylcarbonyl and where for each individual compound the substituents $R^3$–$R^5$ correspond to one line of Table B.

Table 232: Compounds 232.1–232.514

Compounds of the general formula Ic, where $R^1$ is methyl, $R^2$ is Cl, $R^{11}$ is methyl, $R^{12}$ is methylsulfonyl and where for each individual compound the substituents $R^3$–$R^5$ correspond to one line of Table B.

Table 233: Compounds 233.1–233.514

Compounds of the general formula Ic, where $R^1$ is methyl, $R^2$ is Cl, $R^{11}$ is ethyl, $R^{12}$ is methylsulfonyl and where for each individual compound the substituents $R^3$–$R^5$ correspond to one line of Table B.

Table 234: Compounds 234.1–234.514

Compounds of the general formula Ic, where $R^1$ is methyl, $R^2$ is Cl, $R^{11}$ is n-propyl, $R^{12}$ is methylsulfonyl and where for each individual compound the substituents $R^3$–$R^5$ correspond to one line of Table B.

Table 235: Compounds 235.1–235.514

Compounds of the general formula Ic, where $R^1$ is methyl, $R^2$ is Cl, $R^{11}$ is methyl, $R^{12}$ is ethylsulfonyl and where for each individual compound the substituents $R^3$–$R^5$ correspond to one line of Table B.

Table 236: Compounds 236.1–236.514

Compounds of the general formula Ic, where $R^1$ is methyl, $R^2$ is Cl, $R^{11}$ is ethyl, $R^{12}$ is ethylsulfonyl and where for each individual compound the substituents $R^3$–$R^5$ correspond to one line of Table B.

Table 237: Compounds 237.1–237.514

Compounds of the general formula Ic, where $R^1$ is methyl, $R^2$ is Cl, $R^{11}$ is n-propyl, $R^{12}$ is ethylsulfonyl and where for each individual compound the substituents $R^3$–$R^5$ correspond to one line of Table B.

Table 238: Compounds 238.1–238.514

Compounds of the general formula Ic, where $R^1$ is methyl, $R^2$ is Cl, $R^{11}$ is methyl, $R^{12}$ is 4-methylphenylsulfonyl and where for each individual compound the substituents $R^3$–$R^5$ correspond to one line of Table B.

Table 239: Compounds 239.1–239.514

Compounds of the general formula Ic, where $R^1$ is methyl, $R^2$ is Cl, $R^{11}$ is ethyl, $R^{12}$ is 4-methylphenylsulfonyl and where for each individual compound the substituents $R^3$–$R^5$ correspond to one line of Table B.

Table 240: Compounds 240.1–240.514

Compounds of the general formula Ic, where $R^1$ is methyl, $R^2$ is Cl, $R^{11}$ is n-propyl, $R^{12}$ is 4-methylphenylsulfonyl and where for each individual compound the substituents $R^3$–$R^5$ correspond to one line of Table B.

Table 241: Compounds 241.1–241.514

Compounds of the general formula Ic, where $R^1$ is methyl, $R^2$ is methylsulfonyl, $R^{11}$ is methyl and $R^{12}$ is hydrogen and where for each individual compound the substituents $R^3$–$R^5$ correspond to one line of Table B.

Table 242: Compounds 242.1–242.514

Compounds of the general formula Ic, where $R^1$ is methyl, $R^2$ is methylsulfonyl, $R^{11}$ is ethyl, $R^{12}$ is hydrogen and where for each individual compound the substituents $R^3$–$R^5$ correspond to one line of Table B.

Table 243: Compounds 243.1–243.514

Compounds of the general formula Ic, where $R^1$ is methyl, $R^2$ is methylsulfonyl, $R^{11}$ is n-propyl, $R^{12}$ is hydrogen and where for each individual compound the substituents $R^3$–$R^5$ correspond to one line of Table B.

Table 244: Compounds 244.1–244.514

Compounds of the general formula Ic, where $R^1$ is methyl, $R^2$ is methylsulfonyl, $R^{11}$ is methyl, $R^{12}$ is methyl and where for each individual compound the substituents $R^3$–$R^5$ correspond to one line of Table B.

Table 245: Compounds 245.1–245.514

Compounds of the general formula Ic, where $R^1$ is methyl, $R^2$ is methylsulfonyl, $R^{11}$ is ethyl, $R^{12}$ is methyl and where for each individual compound the substituents $R^3$–$R^5$ correspond to one line of Table B.

Table 246: Compounds 246.1–246.514

Compounds of the general formula Ic, where $R^1$ is methyl, $R^2$ is methylsulfonyl, $R^{11}$ is n-propyl, $R^{12}$ is methyl and where for each individual compound the substituents $R^3$–$R^5$ correspond to one line of Table B.

Table 247: Compounds 247.1–247.514

Compounds of the general formula Ic, where $R^1$ is methyl, $R^2$ is methylsulfonyl, $R^{11}$ is methyl, $R^{12}$ is ethyl and where for each individual compound the substituents $R^3$–$R^5$ correspond to one line of Table B.

Table 248: Compounds 248.1–248.514

Compounds of the general formula Ic, where $R^1$ is methyl, $R^2$ is methylsulfonyl, $R^{11}$ is ethyl, $R^{12}$ is ethyl and where for each individual compound the substituents $R^3$–$R^5$ correspond to one line of Table B.

Table 249: Compounds 249.1–249.514

Compounds of the general formula Ic, where $R^1$ is methyl, $R^2$ is methylsulfonyl, $R^{11}$ is n-propyl, $R^{12}$ is ethyl and where for each individual compound the substituents $R^3$–$R^5$ correspond to one line of Table B.

Table 250: Compounds 250.1–250.514

Compounds of the general formula Ic, where $R^1$ is methyl, $R^2$ is methylsulfonyl, $R^{11}$ is methyl, $R^{12}$ is methylcarbonyl and where for each individual compound the substituents $R^3$–$R^5$ correspond to one line of Table B.

Table 251: Compounds 251.1–251.514

Compounds of the general formula Ic, where $R^1$ is methyl, $R^2$ is methylsulfonyl, $R^{11}$ is ethyl, $R^{12}$ is methylcarbonyl and where for each individual compound the substituents $R^3$–$R^5$ correspond to one line of Table B.

Table 252: Compounds 252.1–252.514

Compounds of the general formula Ic, where $R^1$ is methyl, $R^2$ is methylsulfonyl, $R^{11}$ is n-propyl, $R^{12}$ is methylcarbonyl and where for each individual compound the substituents $R^3$–$R^5$ correspond to one line of Table B.

Table 253: Compounds 253.1–253.514

Compounds of the general formula Ic, where $R^1$ is methyl, $R^2$ is methylsulfonyl, $R^{11}$ is methyl, $R^{12}$ is ethylcarbonyl and where for each individual compound the substituents $R^3$–$R^5$ correspond to one line of Table B.

Table 254: Compounds 254.1–254.514

Compounds of the general formula Ic, where $R^1$ is methyl, $R^2$ is methylsulfonyl, $R^{11}$ is ethyl, $R^{12}$ is ethylcarbonyl and where for each individual compound the substituents $R^3$–$R^5$ correspond to one line of Table B.

Table 255: Compounds 255.1–255.514

Compounds of the general formula Ic, where $R^1$ is methyl, $R^2$ is methylsulfonyl, $R^{11}$ is n-propyl, $R^{12}$ is ethylcarbonyl and where for each individual compound the substituents $R^1$–$R^5$ correspond to one line of Table B.

Table 256: Compounds 256.1–256.514

Compounds of the general formula Ic, where $R^1$ is methyl, $R^2$ is methylsulfonyl, $R^{11}$ is methyl, $R^{12}$ is methylsulfonyl and where for each individual compound the substituents $R^3$–$R^5$ correspond to one line of Table B.

Table 257: Compounds 257.1–257.514

Compounds of the general formula Ic, where $R^1$ is methyl, $R^2$ is methylsulfonyl, $R^{11}$ is ethyl, $R^{12}$ is methylsulfonyl and where for each individual compound the substituents $R^3$–$R^5$ correspond to one line of Table B.

Table 258: Compounds 258.1–258.514

Compounds of the general formula Ic, where $R^1$ is methyl, $R^2$ is methylsulfonyl, $R^{11}$ is n-propyl, $R^{12}$ is methylsulfonyl and where for each individual compound the substituents $R^1$–$R^5$ correspond to one line of Table B.

Table 259: Compounds 259.1–259.514

Compounds of the general formula Ic, where $R^1$ is methyl, $R^2$ is methylsulfonyl, $R^{11}$ is methyl, $R^{12}$ is ethylsulfonyl and where for each individual compound the substituents $R^3$–$R^5$ correspond to one line of Table B.

Table 260: Compounds 260.1–260.514

Compounds of the general formula Ic, where $R^1$ is methyl, $R^2$ is methylsulfonyl, $R^{11}$ is ethyl, $R^{12}$ is ethylsulfonyl and where for each individual compound the substituents $R^3$–$R^5$ correspond to one line of Table B.

Table 261: Compounds 261.1–261.514

Compounds of the general formula Ic, where $R^1$ is methyl, $R^2$ is methylsulfonyl, $R^{11}$ is n-propyl, $R^{12}$ is ethylsulfonyl and where for each individual compound the substituents $R^3$–$R^5$ correspond to one line of Table B.

Table 262: Compounds 262.1–262.514

Compounds of the general formula Ic, where $R^1$ is methyl, $R^2$ is methylsulfonyl, $R^{11}$ is methyl, $R^{12}$ is 4-methylphenylsulfonyl and where for each individual compound the substituents $R^3$–$R^5$ correspond to one line of Table B.

Table 263: Compounds 263.1–263.514

Compounds of the general formula Ic, where $R^1$ is methyl, $R^2$ is methylsulfonyl, $R^{11}$ is ethyl, $R^{12}$ is 4-methylphenylsulfonyl and where for each individual compound the substituents $R^3$–$R^5$ correspond to one line of Table B.

Table 264: Compounds 264.1–264.514

Compounds of the general formula Ic, where $R^1$ is methyl, $R^2$ is methylsulfonyl, $R^{11}$ is n-propyl, $R^{12}$ is 4-methylphenylsulfonyl and where for each individual compound the substituents $R^3$–$R^5$ correspond to one line of Table B.

Table 265: Compounds 265.1–265.514

Compounds of the general formula Ic, where $R^1$ is methyl, $R^2$ is trifluoromethyl, $R^{11}$ is methyl and $R^{12}$ is hydrogen and where for each individual compound the substituents $R^3$–$R^5$ correspond to one line of Table B.

Table 266: Compounds 266.1–266.514

Compounds of the general formula Ic, where $R^1$ is methyl, $R^2$ is trifluoromethyl, $R^{11}$ is ethyl, $R^{12}$ is hydrogen and where for each individual compound the substituents $R^3$–$R^5$ correspond to one line of Table B.

Table 267: Compounds 267.1–267.514

Compounds of the general formula Ic, where $R^1$ is methyl, $R^2$ is trifluoromethyl, $R^{11}$ is n-propyl, $R^{12}$ is hydrogen and where for each individual compound the substituents $R^3$–$R^5$ correspond to one line of Table B.

Table 268: Compounds 268.1–268.514

Compounds of the general formula Ic, where $R^1$ is methyl, $R^2$ is trifluoromethyl, $R^{11}$ is methyl, $R^{12}$ is methyl and where for each individual compound the substituents $R^3$–$R^5$ correspond to one line of Table B.

Table 269: Compounds 269.1–269.514

Compounds of the general formula Ic, where $R^1$ is methyl, $R^2$ is trifluoromethyl, $R^{11}$ is ethyl, $R^{12}$ is methyl and where for each individual compound the substituents $R^3$–$R^5$ correspond to one line of Table B.

Table 270: Compounds 270.1–270.514

Compounds of the general formula Ic, where $R^1$ is methyl, $R^2$ is trifluoromethyl, $R^{11}$ is n-propyl, $R^{12}$ is methyl and where for each individual compound the substituents $R^3$–$R^5$ correspond to one line of Table B.

Table 271: Compounds 271.1–271.514

Compounds of the general formula Ic, where $R^1$ is methyl, $R^2$ is trifluoromethyl, $R^{11}$ is methyl, $R^{12}$ is ethyl and where for each individual compound the substituents $R^3$–$R^5$ correspond to one line of Table B.

Table 272: Compounds 272.1–272.514

Compounds of the general formula Ic, where $R^1$ is methyl, $R^2$ is trifluoromethyl, $R^{11}$ is ethyl, $R^{12}$ is ethyl and where for each individual compound the substituents $R^3$–$R^5$ correspond to one line of Table B.

Table 273: Compounds 273.1–273.514

Compounds of the general formula Ic, where $R^1$ is methyl, $R^2$ is trifluoromethyl, $R^{11}$ n-propyl, $R^{12}$ is ethyl and where for each individual compound the substituents $R^3$–$R^5$ correspond to one line of Table B.

Table 274: Compounds 274.1–274.514

Compounds of the general formula Ic, where $R^1$ is methyl, $R^2$ is trifluoromethyl, $R^{11}$ is methyl, $R^{12}$ is methylcarbonyl and where for each individual compound the substituents $R^3$–$R^5$ correspond to one line of Table B.

Table 275: Compounds 275.1–275.514

Compounds of the general formula Ic, where $R^1$ is methyl, $R^2$ is trifluoromethyl, $R^{11}$ is ethyl, $R^{12}$ is methylcarbonyl and where for each individual compound the substituents $R^3$–$R^5$ correspond to one line of Table B.

Table 276: Compounds 276.1–276.514

Compounds of the general formula Ic, where $R^1$ is methyl, $R^2$ is trifluoromethyl, $R^{11}$ is n-propyl, $R^{12}$ is methylcarbonyl and where for each individual compound the substituents $R^3$–$R^5$ correspond to one line of Table B.

Table 277: Compounds 277.1–277.514

Compounds of the general formula Ic, where $R^1$ is methyl, $R^2$ is trifluoromethyl, $R^{11}$ is methyl, $R^{12}$ is ethylcarbonyl and where for each individual compound the substituents $R^3$–$R^5$ correspond to one line of Table B.

Table 278: Compounds 278.1–278.514

Compounds of the general formula Ic, where $R^1$ is methyl, $R^2$ is trifluoromethyl, $R^{11}$ is ethyl, $R^{12}$ is ethylcarbonyl and where for each individual compound the substituents $R^3$–$R^5$ correspond to one line of Table B.

Table 279: Compounds 279.1–279.514

Compounds of the general formula Ic, where $R^1$ is methyl, $R^2$ is trifluoromethyl, $R^{11}$ is n-propyl, $R^{12}$ is ethylcarbonyl and where for each individual compound the substituents $R^3$–$R^5$ correspond to one line of Table B.

Table 280: Compounds 280.1–280.514

Compounds of the general formula Ic, where $R^1$ is methyl, $R^2$ is trifluoromethyl, $R^{11}$ is methyl, $R^{12}$ is methylsulfonyl and where for each individual compound the substituents $R^3$–$R^5$ correspond to one line of Table B.

Table 281: Compounds 281.1–281.514

Compounds of the general formula Ic, where $R^1$ is methyl, $R^2$ is trifluoromethyl, $R^{11}$ is ethyl, $R^{12}$ is methylsulfonyl and where for each individual compound the substituents $R^3$–$R^5$ correspond to one line of Table B.

Table 282: Compounds 282.1–282.514

Compounds of the general formula Ic, where $R^1$ is methyl, $R^2$ is trifluoromethyl, $R^{11}$ is n-propyl, $R^{12}$ is methylsulfonyl and where for each individual compound the substituents $R^3$–$R^5$ correspond to one line of Table B.

Table 283: Compounds 283.1–283.514

Compounds of the general formula Ic, where $R^1$ is methyl, $R^2$ is trifluoromethyl, $R^{11}$ is methyl, $R^{12}$ is ethylsulfonyl and where for each individual compound the substituents $R^3$–$R^5$ correspond to one line of Table B.

Table 284: Compounds 284.1–284.514

Compounds of the general formula Ic, where $R^1$ is methyl, $R^2$ is trifluoromethyl, $R^{11}$ is ethyl, $R^{12}$ is ethylsulfonyl and where for each individual compound the substituents $R^3$–$R^5$ correspond to one line of Table B.

Table 285: Compounds 285.1–285.514

Compounds of the general formula Ic, where $R^1$ is methyl, $R^2$ is trifluoromethyl, $R^{11}$ is n-propyl, $R^{12}$ is ethylsulfonyl and where for each individual compound the substituents $R^3$–$R^5$ correspond to one line of Table B.

Table 286: Compounds 286.1–286.514

Compounds of the general formula Ic, where $R^1$ is methyl, $R^2$ is trifluoromethyl, $R^{11}$ is methyl, $R^{12}$ is 4-methylphenylsulfonyl and where for each individual compound the substituents $R^3$–$R^5$ correspond to one line of Table B.

Table 287: Compounds 287.1–287.514

Compounds of the general formula Ic, where $R^1$ is methyl, $R^2$ is trifluoromethyl, $R^{11}$ is ethyl, $R^{12}$ is 4-methylphenylsulfonyl and where for each individual compound the substituents $R^3$–$R^5$ correspond to one line of Table B.

Table 288: Compounds 288.1–288.514

Compounds of the general formula Ic, where $R^1$ is methyl, $R^2$ is trifluoromethyl, $R^{11}$ is n-propyl, $R^{12}$ is 4-methylphenylsulfonyl and where for each individual compound the substituents $R^3$–$R^5$ correspond to one line of Table B.

TABLE C

| No. | $R^3$ | $R^8$ | $R^9$ |
|---|---|---|---|
| 1 | H | H | H |
| 2 | H | $CH_3$ | H |
| 3 | H | $C_2H_5$ | H |
| 4 | H | $C_3H_7$ | H |
| 5 | H | $C_4H_9$ | H |
| 6 | H | $CH(CH_3)_2$ | H |
| 7 | H | cy-$C_3H_5$ | H |
| 8 | H | cy-$C_4H_7$ | H |
| 9 | H | cy-$C_5H_9$ | H |
| 10 | H | cy-$C_6$—$H_{11}$ | H |
| 11 | H | $C_6H_5$ | H |
| 12 | H | $CH_2$—$C_6H_5$ | H |
| 13 | H | 2-furyl | H |
| 14 | H | 3-furyl | H |
| 15 | H | 2-thienyl | H |
| 16 | H | 3-thienyl | H |
| 17 | H | 2-dioxanyl | H |
| 18 | H | CHO | H |
| 19 | H | $COCH_3$ | H |
| 20 | H | $COOCH_3$ | H |
| 21 | H | $COOC_2H_5$ | H |
| 22 | H | $OCH_3$ | H |
| 23 | H | CN | H |
| 24 | H | $SCH_3$ | H |
| 25 | H | $COCF_3$ | H |
| 26 | H | $COC_6H_5$ | H |
| 27 | H | CH═$NOCH_3$ | H |
| 28 | H | CH═$NOC_2H_5$ | H |
| 29 | H | $C(CH_3)$═$NOCH_3$ | H |
| 30 | H | $CH_3$ | $CH_3$ |
| 31 | H | $C_2H_5$ | $CH_3$ |
| 32 | H | $C_3H_7$ | $CH_3$ |
| 33 | H | $C_4H_9$ | $CH_3$ |
| 34 | H | CHO | $CH_3$ |
| 35 | H | $COCH_3$ | $CH_3$ |
| 36 | H | $COOCH_3$ | $CH_3$ |
| 37 | H | $OCH_3$ | $CH_3$ |
| 38 | H | $C_6H_5$ | $CH_3$ |
| 39 | H | $CH_2$—CHO | H |
| 40 | H | $COOCH_2C_6H_5$ | H |
| 41 | Cl | $CH_3$ | H |
| 42 | $CH_3$ | $CH_3$ | H |
| 43 | $C_2H_5$ | $CH_3$ | H |
| 44 | $CF_3$ | $CH_3$ | H |
| 45 | $OCH_3$ | $CH_3$ | H |
| 46 | $OC_2H_5$ | $CH_3$ | H |
| 47 | $CH_2$—C≡CH | $CH_3$ | H |
| 48 | $CH_2$—CH═$CH_2$ | $CH_3$ | H |
| 49 | Cl | $CH_3$ | H |
| 50 | $CH_3$ | $CH_3$ | H |
| 51 | $CF_3$ | $CH_3$ | H |
| 52 | $OCH_3$ | $CH_3$ | H |
| 53 | $OC_2H_5$ | $CH_3$ | H |
| 54 | $CH_2$—CH═$CH_2$ | $CH_3$ | H |
| 55 | $CH_2$—C≡CH | $CH_3$ | H |
| 56 | H | $CH_3$ | Ph |
| 57 | H | $C_2H_5$ | Ph |
| 58 | H | $C_3H_7$ | Ph |
| 59 | H | $C_4H_9$ | Ph |
| 60 | H | CHO | Ph |
| 61 | H | $COCH_3$ | Ph |
| 62 | H | $COOCH_3$ | Ph |
| 63 | H | $OCH_3$ | Ph |
| 64 | H | $C_6H_5$ | Ph |
| 65 | H | CH═$NOCH_3$ | Ph |
| 66 | H | $C(CH_3)$═$NOCH_3$ | Ph |
| 67 | $CH_3$ | 2-Cl—$C_6H_4$ | H |
| 68 | $CH_3$ | 3-Br—$C_6H_4$ | H |
| 69 | $CH_3$ | 4-F—$C_6H_4$ | H |
| 70 | $CH_3$ | 2,4-$Cl_2$—$C_6H_3$ | H |
| 71 | $CH_3$ | 2-$NO_2$—$C_6H_4$ | H |
| 72 | $CH_3$ | 3-CN—$C_6H_4$ | H |
| 73 | $CH_3$ | 4-Me—$C_6H_4$ | H |
| 74 | $CH_3$ | 2-OMe—$C_6H_4$ | H |
| 75 | $CH_3$ | 3-$CF_3$—$C_6H_4$ | H |
| 76 | $CH_3$ | 4-$OCF_3$—$C_6H_4$ | H |
| 77 | $CH_3$ | 2-Me—$C_6H_4$ | H |
| 78 | $CH_3$ | 3-Me—$C_6H_4$ | H |
| 79 | $CH_3$ | 2-SMe—$C_6H_4$ | H |
| 80 | $CH_3$ | 3-COOMe—$C_6H_4$ | H |
| 81 | $CH_3$ | 4-$CF_3$—$C_6H_4$ | H |
| 82 | $CH_3$ | 2-$CF_3$—$C_6H_4$ | H |
| 83 | $CH_3$ | 3-OMe—$C_6H_4$ | H |
| 84 | $CH_3$ | 4-OMe—$C_6H_4$ | H |
| 85 | H | 2-Furyl | $CH_3$ |
| 86 | H | 3-furyl | $CH_3$ |
| 87 | H | 2-thienyl | $CH_3$ |
| 88 | H | 3-thienyl | $CH_3$ |
| 89 | H | 2-pyridyl | $CH_3$ |
| 90 | H | 3-pyridyl | $CH_3$ |
| 91 | H | 4-pyridyl | $CH_3$ |
| 92 | H | 2-thiazolyl | $CH_3$ |
| 93 | H | 4-thiazolyl | $CH_3$ |
| 94 | H | 5-thiazolyl | $CH_3$ |
| 95 | H | 2-pyrrolyl | $CH_3$ |
| 96 | H | 3-pyrrolyl | $CH_3$ |
| 97 | H | 4-pyrrolyl | $CH_3$ |
| 98 | H | 3-isoxazolyl | $CH_3$ |
| 99 | H | 4-isoxazolyl | $CH_3$ |
| 100 | H | 5-isoxazolyl | $CH_3$ |
| 101 | H | 2-oxazolyl | $CH_3$ |
| 102 | H | 4-oxazolyl | $CH_3$ |

The Tables 289–432 below are based on the 4-benzoylpyrazoles of the formula Id:

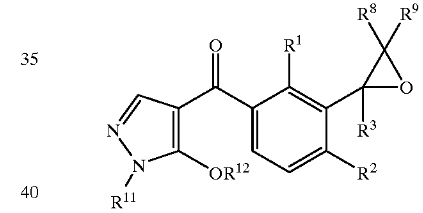

Table 289: Compounds 289.1–289.102

Compounds of the general formula Id where $R^1$ is Cl, $R^2$ is methylsulfonyl, $R^{11}$ is methyl and $R^{12}$ is hydrogen and where for each individual compound the substituents $R^3$, $R^8$ and $R^9$ correspond to one line of Table C.

Table 290: Compounds 290.1–290.102

Compounds of the general formula Id where $R^1$ is Cl, $R^2$ is methylsulfonyl, $R^{11}$ is ethyl, $R^{12}$ is hydrogen and where for each individual compound the substituents $R^3$, $R^8$ and $R^9$ correspond to one line of Table C.

Table 291: Compounds 291.1–291.102

Compounds of the general formula Id where $R^1$ is Cl, $R^2$ is methylsulfonyl, $R^{11}$ is n-propyl, $R^{12}$ is hydrogen and where for each individual compound the substituents $R^3$, $R^8$ and $R^9$ correspond to one line of Table C.

Table 292: Compounds 292.1–292.102

Compounds of the general formula Id where $R^1$ is Cl, $R^2$ is methylsulfonyl, $R^{11}$ is methyl, $R^{12}$ is methyl and where for each individual compound the substituents $R^3$, $R^8$ and $R^9$ correspond to one line of Table C.

Table 293: Compounds 293.1–293.102

Compounds of the general formula Id where $R^1$ is Cl, $R^2$ is methylsulfonyl, $R^{11}$ is ethyl, $R^{12}$ is methyl and where for each individual compound the substituents $R^3$, $R^8$ and $R^9$ correspond to one line of Table C.

Table 294: Compounds 294.1–294.102

Compounds of the general formula Id where $R^1$ is Cl, $R^2$ is methylsulfonyl, $R^{11}$ is n-propyl, $R^{12}$ is methyl and where for each individual compound the substituents $R^3$, $R^8$ and $R^9$ correspond to one line of Table C.

Table 295: Compounds 295.1–295.102

Compounds of the general formula Id where $R^1$ is Cl, $R^2$ is methylsulfonyl, $R^{11}$ is methyl, $R^{12}$ is ethyl and where for each individual compound the substituents $R^3$, $R^8$ and $R^9$ correspond to one line of Table C.

Table 296: Compounds 296.1–296.102

Compounds of the general formula Id where $R^1$ is Cl, $R^2$ is methylsulfonyl, $R^{11}$ is ethyl, $R^{12}$ is ethyl and where for each individual compound the substituents $R^3$, $R^8$ and $R^9$ correspond to one line of Table C.

Table 297: Compounds 297.1–297.102

Compounds of the general formula Id where $R^1$ is Cl, $R^2$ is methylsulfonyl, $R^{11}$ is n-propyl, $R^{12}$ is ethyl and where for each individual compound the substituents $R^3$, $R^8$ and $R^9$ correspond to one line of Table C.

Table 298: Compounds 298.1–298.102

Compounds of the general formula Id where $R^1$ is Cl, $R^2$ is methylsulfonyl, $R^{11}$ is methyl, $R^{12}$ is methylcarbonyl and where for each individual-compound the substituents $R^3$, $R^8$ and $R^9$ correspond to one line of Table C.

Table 299: Compounds 299.1–299.102

Compounds of the general formula Id where $R^1$ is Cl, $R^2$ is methylsulfonyl, $R^{11}$ is ethyl, $R^{12}$ is methylcarbonyl and where for each individual compound the substituents $R^3$, $R^8$ and $R^9$ correspond to one line of Table C.

Table 300: Compounds 300.1–300.102

Compounds of the general formula Id where $R^1$ is Cl, $R^2$ is methylsulfonyl, $R^{11}$ is n-propyl, $R^{12}$ is methylcarbonyl and where for each individual compound the substituents $R^3$, $R^8$ and $R^9$ correspond to one line of Table C.

Table 301: Compounds 301.1–301.102

Compounds of the general formula Id where $R^1$ is Cl, $R^2$ is methylsulfonyl, $R^{11}$ is methyl, $R^{12}$ is ethylcarbonyl and where for each individual compound the substituents $R^3$, $R^8$ and $R^9$ correspond to one line of Table C.

Table 302: Compounds 302.1–302.102

Compounds of the general formula Id where $R^1$ is Cl, $R^2$ is methylsulfonyl, $R^{11}$ is ethyl, $R^{12}$ is ethylcarbonyl and where for each individual compound the substituents $R^3$, $R^8$ and $R^9$ correspond to one line of Table C.

Table 303: Compounds 303.1–303.102

Compounds of the general formula Id where $R^1$ is Cl, $R^2$ is methylsulfonyl, $R^{11}$ is n-propyl, $R^{12}$ is ethylcarbonyl and where for each individual compound the substituents $R^3$, $R^5$ and $R^9$ correspond to one line of Table C.

Table 304: Compounds 304.1–304.102

Compounds of the general formula Id where $R^1$ is Cl, $R^2$ is methylsulfonyl, $R^{11}$ is methyl, $R^{12}$ is methylsulfonyl and where for each individual compound the substituents $R^3$, $R^8$ and $R^9$ correspond to one line of Table C.

Table 305: Compounds 305.1–305.102

Compounds of the general formula Id where $R^1$ is Cl, $R^2$ is methylsulfonyl, $R^{11}$ is ethyl, $R^{12}$ is methylsulfonyl and where for each individual compound the substituents $R^3$, $R^8$ and $R^9$ correspond to one line of Table C.

Table 306: Compounds 306.1–306.102

Compounds of the general formula Id where $R^1$ is Cl, $R^2$ is methylsulfonyl, $R^{11}$ is n-propyl, $R^{12}$ is methylsulfonyl and where for each individual compound the substituents $R^3$, $R^8$ and $R^9$ correspond to one line of Table C.

Table 307: Compounds 307.1–307.102

Compounds of the general formula Id where $R^1$ is Cl, $R^2$ is methylsulfonyl, $R^{11}$ is methyl, $R^{12}$ is ethylsulfonyl and where for each individual compound the substituents $R^3$, $R^8$ and $R^9$ correspond to one line of Table C.

Table 308: Compounds 308.1–308.102

Compounds of the general formula Id where $R^1$ is Cl, $R^2$ is methylsulfonyl, $R^{11}$ is ethyl, $R^{12}$ is ethylsulfonyl and where for each individual compound the substituents $R^3$, $R^8$ and $R^9$ correspond to one line of Table C.

Table 309: Compounds 309.1–309.102

Compounds of the general formula Id where $R^1$ is Cl, $R^2$ is methylsulfonyl, $R^{11}$ is n-propyl, $R^{12}$ is ethylsulfonyl and where for each individual compound the substituents $R^3$, $R^8$ and $R^9$ correspond to one line of Table C.

Table 310: Compounds 310.1–310.102

Compounds of the general formula Id where $R^1$ is Cl, $R^2$ is methylsulfonyl, $R^{11}$ is methyl, $R^{12}$ is 4-methylphenylsulfonyl and where for each individual compound the substituents $R^3$, $R^8$ and $R^9$ correspond to one line of Table C.

Table 311: Compounds 311.1–311.102

Compounds of the general formula Id where $R^1$ is Cl, $R^2$ is methylsulfonyl, $R^{11}$ is ethyl, $R^{12}$ is 4-methylphenylsulfonyl and where for each individual compound the substituents $R^3$, $R^8$ and $R^9$ correspond to one line of Table C.

Table 312: Compounds 312.1–312.102

Compounds of the general formula Id where $R^1$ is Cl, $R^2$ is methylsulfonyl, $R^{11}$ is n-propyl, $R^{12}$ is 4-methylphenylsulfonyl and where for each individual compound the substituents $R^3$, $R^8$ and $R^9$ correspond to one line of Table C.

Table 313: Compounds 313.1–313.102

Compounds of the general formula Id where $R^1$ is Cl, $R^2$ is Cl, $R^{11}$ is methyl and $R^{12}$ is hydrogen and where for each individual compound the substituents $R^3$, $R^8$ and $R^9$ correspond to one line of Table C.

Table 314: Compounds 314.1–314.102

Compounds of the general formula Id where $R^1$ is Cl, $R^2$ is Cl, $R^{11}$ is ethyl, $R^{12}$ is hydrogen and where for each individual compound the substituents $R^3$, $R^8$ and $R^9$ correspond to one line of Table C.

Table 315: Compounds 315.1–315.102

Compounds of the general formula Id where $R^1$ is Cl, $R^2$ is Cl, $R^{11}$ is n-propyl, $R^{12}$ is hydrogen and where for each individual compound the substituents $R^3$, $R^8$ and $R^9$ correspond to one line of Table C.

Table 316: Compounds 316.1–316.102

Compounds of the general formula Id where $R^1$ is Cl, $R^2$ is Cl, $R^{11}$ is methyl, $R^{12}$ is methyl and where for each individual compound the substituents $R^3$, $R^8$ and $R^9$ correspond to one line of Table C.

Table 317: Compounds 317.1–317.102

Compounds of the general formula Id where $R^1$ is Cl, $R^2$ is Cl, $R^{11}$ is ethyl, $R^{12}$ is methyl and where for each individual compound the substituents $R^3$, $R^8$ and $R^9$ correspond to one line of Table C.

Table 318: Compounds 318.1–318.102

Compounds of the general formula Id where $R^1$ is Cl, $R^2$ is Cl, $R^{11}$ is n-propyl, $R^{12}$ is methyl and where for each individual compound the substituents $R^3$, $R^8$ and $R^9$ correspond to one line of Table C.

Table 319: Compounds 319.1–319.102

Compounds of the general formula Id where $R^1$ is Cl, $R^2$ is Cl, $R^{11}$ is methyl, $R^{12}$ is ethyl and where for each individual compound the substituents $R^3$, $R^8$ and $R^9$ correspond to one line of Table C.

Table 320: Compounds 320.1–320.102

Compounds of the general formula Id where $R^1$ is Cl, $R^2$ is Cl, $R^{11}$ is ethyl, $R^{12}$ is ethyl and where for each individual compound the substituents $R^3$, $R^8$ and $R^9$ correspond to one line of Table C.

Table 321: Compounds 321.1–321.102

Compounds of the general formula Id where $R^1$ is Cl, $R^2$ is Cl, $R^{11}$ is n-propyl, $R^{12}$ is ethyl and where for each individual compound the substituents $R^3$, $R^8$ and $R^9$ correspond to one line of Table C.

Table 322: Compounds 322.1–322.102

Compounds of the general formula Id where $R^1$ is Cl, $R^2$ is Cl, $R^{11}$ is methyl, $R^{12}$ is methylcarbonyl and where for each individual compound the substituents $R^3$, $R^8$ and $R^9$ correspond to one line of Table C.

Table 323: Compounds 323.1–323.102

Compounds of the general formula Id where $R^1$ is Cl, $R^2$ is Cl, $R^{11}$ is ethyl, $R^{12}$ is methylcarbonyl and where for each individual compound the substituents $R^3$, $R^8$ and $R^9$ correspond to one line of Table C.

Table 324: Compounds 324.1–324.102

Compounds of the general formula Id where $R^1$ is Cl, $R^2$ is Cl, $R^{11}$ is n-propyl, $R^{12}$ is methylcarbonyl and where for each individual compound the substituents $R^3$, $R^8$ and $R^9$ correspond to one line of Table C.

Table 325: Compounds 325.1–325.102

Compounds of the general formula Id where $R^1$ is Cl, $R^2$ is Cl, $R^{11}$ is methyl, $R^{12}$ is ethylcarbonyl and where for each individual compound the substituents $R^3$, $R^8$ and $R^9$ correspond to one line of Table C.

Table 326: Compounds 326.1–326.102

Compounds of the general formula Id where $R^1$ is Cl, $R^2$ is Cl, $R^{11}$ is ethyl, $R^{12}$ is ethylcarbonyl and where for each individual compound the substituents $R^3$, $R^8$ and $R^9$ correspond to one line of Table C.

Table 327: Compounds 327.1–327.102

Compounds of the general formula Id where $R^1$ is Cl, $R^2$ is Cl, $R^{11}$ is n-propyl, $R^{12}$ is ethylcarbonyl and where for each individual compound the substituents $R^3$, $R^8$ and $R^9$ correspond to one line of Table C.

Table 328: Compounds 328.1–328.102

Compounds of the general formula Id where $R^1$ is Cl, $R^2$ is Cl, $R^{11}$ is methyl, $R^{12}$ is methylsulfonyl and where for each individual compound the substituents $R^3$, $R^8$ and $R^9$ correspond to one line of Table C.

Table 329: Compounds 329.1–329.102

Compounds of the general formula Id where $R^1$ is Cl, $R^2$ is Cl, $R^{11}$ is ethyl, $R^{12}$ is methylsulfonyl and where for each individual compound the substituents $R^3$, $R^8$ and $R^9$ correspond to one line of Table C.

Table 330: Compounds 330.1–330.102

Compounds of the general formula Id where $R^1$ is Cl, $R^2$ is Cl, $R^{11}$ is n-propyl, $R^{12}$ is methylsulfonyl and where for each individual compound the substituents $R^3$, $R^8$ and $R^9$ correspond to one line of Table C.

Table 331: Compounds 331.1–331.102

Compounds of the general formula Id where $R^1$ is Cl, $R^2$ is Cl, $R^{11}$ is methyl, $R^{12}$ is ethylsulfonyl and where for each individual compound the substituents $R^3$, $R^8$ and $R^9$ correspond to one line of Table C.

Table 332: Compounds 332.1–332.102

Compounds of the general formula Id where $R^1$ is Cl, $R^2$ is Cl, $R^{11}$ is ethyl, $R^{12}$ is ethylsulfonyl and where for each individual compound the substituents $R^3$, $R^8$ and $R^9$ correspond to one line of Table C.

Table 333: Compounds 333.1–333.102

Compounds of the general formula Id where $R^1$ is Cl, $R^2$ is Cl, $R^{11}$ is n-propyl, $R^{12}$ is ethylsulfonyl and where for each individual compound the substituents $R^3$, $R^8$ and $R^9$ correspond to one line of Table C.

Table 334: Compounds 334.1–334.102

Compounds of the general formula Id where $R^1$ is Cl, $R^2$ is Cl, $R^{11}$ is methyl, $R^{12}$ is 4-methylphenylsulfonyl and where for each individual compound the substituents $R^3$, $R^8$ and $R^9$ correspond to one line of Table C.

Table 335: Compounds 335.1–335.102

Compounds of the general formula Id where $R^1$ is Cl, $R^2$ is Cl, $R^{11}$ is ethyl, $R^{12}$ is 4-methylphenylsulfonyl and where for each individual compound the substituents $R^3$, $R^8$ and $R^9$ correspond to one line of Table C.

Table 336: Compounds 336.1–336.102

Compounds of the general formula Id where $R^1$ is Cl, $R^2$ is Cl, $R^{11}$ is n-propyl, $R^{12}$ is 4-methylphenylsulfonyl and where for each individual compound the substituents $R^3$, $R^8$ and $R^9$ correspond to one line of Table C.

Table 337: Compounds 337.1–337.102

Compounds of the general formula Id where $R^1$ is Cl, $R^2$ is trifluoromethyl, $R^{11}$ is methyl and $R^{12}$ is hydrogen and where for each individual compound the substituents $R^3$, $R^8$ and $R^9$ correspond to one line of Table C.

Table 338: Compounds 338.1–338.102

Compounds of the general formula Id where $R^1$ is Cl, $R^2$ is trifluoromethyl, $R^{11}$ is ethyl, $R^{12}$ is hydrogen and where for each individual compound the substituents correspond to one line of Table C.

Table 339: Compounds 339.1–339.102

Compounds of the general formula Id where $R^1$ is Cl, $R^2$ is trifluoromethyl, $R^{11}$ is n-propyl, $R^{12}$ is hydrogen and where for each individual compound the substituents $R^3$, $R^8$ and $R^9$ correspond to one line of Table C.

Table 340: Compounds 340.1–340.102

Compounds of the general formula Id where $R^1$ is Cl, $R^2$ is trifluoromethyl, $R^{11}$ is methyl, $R^{12}$ is methyl and where for each individual compound the substituents $R^3$, $R^8$ and $R^9$ correspond to one line of Table C.

Table 341: Compounds 341.1–341.102

Compounds of the general formula Id where $R^1$ is Cl, $R^2$ is trifluoromethyl, $R^{11}$ is ethyl, $R^{12}$ is methyl and where for each individual compound the substituents $R^3$, $R^8$ and $R^9$ correspond to one line of Table C.

Table 342: Compounds 342.1–342.102

Compounds of the general formula Id where $R^1$ is Cl, $R^2$ is trifluoromethyl, $R^{11}$ is n-propyl, $R^{12}$ is methyl and where for each individual compound the substituents $R^3$, $R^8$ and $R^9$ correspond to one line of Table C.

Table 343: Compounds 343.1–343.102

Compounds of the general formula Id where $R^1$ is Cl, $R^2$ is trifluoromethyl, $R^{11}$ is methyl, $R^{12}$ is ethyl and where for each individual compound the substituents $R^3$, $R^8$ and $R^9$ correspond to one line of Table C.

Table 344: Compounds 344.1–344.102

Compounds of the general formula Id where $R^1$ is Cl, $R^2$ is trifluoromethyl, $R^{11}$ is ethyl, $R^{12}$ is ethyl and where for each individual compound the substituents $R^3$, $R^8$ and $R^9$ correspond to one line of Table C.

Table 345: Compounds 345.1–345.102

Compounds of the general formula Id where $R^1$ is Cl, $R^2$ is trifluoromethyl, $R^{11}$ is n-propyl, $R^{12}$ is ethyl and where for each individual compound the substituents $R^3$, $R^8$ and $R^9$ correspond to one line of Table C.

Table 346: Compounds 346.1–346.102

Compounds of the general formula Id where $R^1$ is Cl, $R^2$ is trifluoromethyl, $R^{11}$ is methyl, $R^{12}$ is methylcarbonyl and where for each individual compound the substituents $R^3$, $R^8$ and $R^9$ correspond to one line of Table C.

Table 347: Compounds 347.1–347.102

Compounds of the general formula Id where $R^1$ is Cl, $R^2$ is trifluoromethyl, $R^{11}$ is ethyl, $R^{12}$ is methylcarbonyl and where for each individual compound the substituents $R^3$, $R^8$ and $R^9$ correspond to one line of Table C.

Table 348: Compounds 348.1–348.102

Compounds of the general formula Id where $R^1$ is Cl, $R^2$ is trifluoromethyl, $R^{11}$ is n-propyl, $R^{12}$ is methylcarbonyl and where for each individual compound the substituents $R^3$, $R^8$ and $R^9$ correspond to one line of Table C.

Table 349: Compounds 349.1–349.102

Compounds of the general formula Id where $R^1$ is Cl, $R^2$ is trifluoromethyl, $R^{11}$ is methyl, $R^{12}$ is ethylcarbonyl and where for each individual compound the substituents $R^3$, $R^8$ and $R^9$ correspond to one line of Table C.

Table 350: Compounds 350.1–350.102

Compounds of the general formula Id where $R^1$ is Cl, $R^2$ is trifluoromethyl, $R^{11}$ is ethyl, $R^{12}$ is ethylcarbonyl and where for each individual compound the substituents $R^3$, $R^8$ and $R^9$ correspond to one line of Table C.

Table 351: Compounds 351.1–351.102

Compounds of the general formula Id where $R^1$ is Cl, $R^2$ is trifluoromethyl, $R^{11}$ is n-propyl, $R^{12}$ is ethylcarbonyl and where for each individual compound the substituents $R^3$, $R^8$ and $R^9$ correspond to one line of Table C.

Table 352: Compounds 352.1–352.102

Compounds of the general formula Id where $R^1$ is Cl, $R^2$ is trifluoromethyl, $R^{11}$ is methyl, $R^{12}$ is methylsulfonyl and where for each individual compound the substituents $R^3$, $R^8$ and $R^9$ correspond to one line of Table C.

Table 353: Compounds 353.1–353.102

Compounds of the general formula Id where $R^1$ is Cl, $R^2$ is trifluoromethyl, $R^{11}$ is ethyl, $R^{12}$ is methylsulfonyl and where for each individual compound the substituents $R^3$, $R^8$ and $R^9$ correspond to one line of Table C.

Table 354: Compounds 354.1–354.102

Compounds of the general formula Id where $R^1$ is Cl, $R^2$ is trifluoromethyl, $R^{11}$ is n-propyl, $R^{12}$ is methylsulfonyl and where for each individual compound the substituents $R^3$, $R^8$ and $R^9$ correspond to one line of Table C.

Table 355: Compounds 355.1–355.102

Compounds of the general formula Id where $R^1$ is Cl, $R^2$ is trifluoromethyl, $R^{11}$ is methyl, $R^{12}$ is ethylsulfonyl and where for each individual compound the substituents $R^3$, $R^8$ and $R^9$ correspond to one line of Table C.

Table 356: Compounds 356.1–356.102

Compounds of the general formula Id where $R^1$ is Cl, $R^2$ is trifluoromethyl, $R^{11}$ is ethyl, $R^{12}$ is ethylsulfonyl and where for each individual compound the substituents $R^3$, $R^8$ and $R^9$ correspond to one line of Table C.

Table 357: Compounds 357.1–357.102

Compounds of the general formula Id where $R^1$ is Cl, $R^2$ is trifluoromethyl, $R^{11}$ is n-propyl, $R^{12}$ is ethylsulfonyl and where for each individual compound the substituents $R^3$, $R^8$ and $R^9$ correspond to one line of Table C.

Table 358: Compounds 358.1–358.102

Compounds of the general formula Id where $R^1$ is Cl, $R^2$ is trifluoromethyl, $R^{11}$ is methyl, $R^{12}$ is 4-methylphenylsulfonyl and where for each individual compound the substituents $R^3$, $R^5$ and $R^9$ correspond to one line of Table C.

Table 359: Compounds 359.1–359.102

Compounds of the general formula Id where $R^1$ is Cl, $R^2$ is trifluoromethyl, $R^{11}$ is ethyl, $R^{12}$ is 4-methylphenylsulfonyl and where for each individual compound the substituents $R^3$, $R^5$ and $R^9$ correspond to one line of Table C.

Table 360: Compounds 360.1–360.102

Compounds of the general formula Id where $R^1$ is Cl, $R^2$ is trifluoromethyl, $R^{11}$ is n-propyl, $R^{12}$ is 4-methylphenylsulfonyl and where for each individual compound the substituents $R^3$, $R^8$ and $R^9$ correspond to one line of Table C.

Table 361: Compounds 361.1–361.102

Compounds of the general formula Id where $R^1$ is methyl, $R^2$ is Cl, $R^{11}$ is methyl and $R^{12}$ is hydrogen and where for each individual compound the substituents $R^3$, $R^8$ and $R^9$ correspond to one line of Table C.

Table 362: Compounds 362.1–362.102

Compounds of the general formula Id where $R^1$ is methyl, $R^2$ is Cl, $R^{11}$ is ethyl, $R^{12}$ is hydrogen and where for each individual compound the substituents $R^3$, $R^8$ and $R^9$ correspond to one line of Table C.

Table 363: Compounds 363.1–363.102

Compounds of the general formula Id where $R^1$ is methyl, $R^2$ is Cl, $R^{11}$ is n-propyl, $R^{12}$ is hydrogen and where for each individual compound the substituents $R^3$, $R^8$ and $R^9$ correspond to one line of Table C.

Table 364: Compounds 364.1–364.102

Compounds of the general formula Id where $R^1$ is methyl, $R^2$ is Cl, $R^{11}$ is methyl, $R^{12}$ is methyl and where for each individual compound the substituents $R^3$, $R^8$ and $R^9$ correspond to one line of Table C.

Table 365: Compounds 365.1–365.102

Compounds of the general formula Id where $R^1$ is methyl, $R^2$ is Cl, $R^{11}$ is ethyl, $R^{12}$ is methyl and where for each individual compound the substituents $R^3$, $R^8$ and $R^9$ correspond to one line of Table C.

Table 366: Compounds 366.1–366.102

Compounds of the general formula Id where $R^1$ is methyl, $R^2$ is Cl, $R^{11}$ is n-propyl, $R^{12}$ is methyl and where for each individual compound the substituents $R^3$, $R^8$ and $R^9$ correspond to one line of Table C.

Table 367: Compounds 367.1–367.102

Compounds of the general formula Id where $R^1$ is methyl, $R^2$ is Cl, $R^{11}$ is methyl, $R^{12}$ is ethyl and where for each individual compound the substituents $R^3$, $R^8$ and $R^9$ correspond to one line of Table C.

Table 368: Compounds 368.1–368.102

Compounds of the general formula Id where $R^1$ is methyl, $R^2$ is Cl, $R^{11}$ is ethyl, $R^{12}$ is ethyl and where for each individual compound the substituents $R^3$, $R^8$ and $R^9$ correspond to one line of Table C.

Table 369: Compounds 369.1–369.102

Compounds of the general formula Id where $R^1$ is methyl, $R^2$ is Cl, $R^{11}$ is n-propyl, $R^{12}$ is ethyl and where for each individual compound the substituents $R^3$, $R^8$ and $R^9$ correspond to one line of Table C.

Table 370: Compounds 370.1–370.102

Compounds of the general formula Id where $R^1$ is methyl, $R^2$ is Cl, $R^{11}$ is methyl, $R^{12}$ is methylcarbonyl and where for each individual compound the substituents $R^3$, $R^8$ and $R^9$ correspond to one line of Table C.

Table 371: Compounds 371.1–371.102

Compounds of the general formula Id where $R^1$ is methyl, $R^2$ is Cl, $R^{11}$ is ethyl, $R^{12}$ is methylcarbonyl and where for each individual compound the substituents $R^3$, $R^8$ and $R^9$ correspond to one line of Table C.

Table 372: Compounds 372.1–372.102

Compounds of the general formula Id where $R^1$ is methyl, $R^2$ is Cl, $R^{11}$ is n-propyl, $R^{12}$ is methylcarbonyl and where for each individual compound the substituents $R^3$, $R^8$ and $R^9$ correspond to one line of Table C.

Table 373: Compounds 373.1–373.102

Compounds of the general formula Id where $R^1$ is methyl, $R^2$ is Cl, $R^{11}$ is methyl, $R^{12}$ is ethylcarbonyl and where for each individual compound the substituents $R^3$, $R^8$ and $R^9$ correspond to one line of Table C.

Table 374: Compounds 374.1–374.102

Compounds of the general formula Id where $R^1$ is methyl, $R^2$ is Cl, $R^{11}$ is ethyl, $R^{12}$ is ethylcarbonyl and where for each individual compound the substituents $R^3$, $R^8$ and $R^9$ correspond to one line of Table C.

Table 375: Compounds 375.1–375.102

Compounds of the general formula Id where $R^1$ is methyl, $R^2$ is Cl, $R^{11}$ is n-propyl, $R^{12}$ is ethylcarbonyl and where for each individual compound the substituents $R^3$, $R^8$ and $R^9$ correspond to one line of Table C.

Table 376: Compounds 376.1–376.102

Compounds of the general formula Id where $R^1$ is methyl, $R^2$ is Cl, $R^{11}$ is methyl, $R^{12}$ is methylsulfonyl and where for each individual compound the substituents $R^3$, $R^8$ and $R^9$ correspond to one line of Table C.

Table 377: Compounds 377.1–377.102

Compounds of the general formula Id where $R^1$ is methyl, $R^2$ is Cl, $R^{11}$ is ethyl, $R^{12}$ is methylsulfonyl and where for each individual compound the substituents $R^3$, $R^8$ and $R^9$ correspond to one line of Table C.

Table 378: Compounds 378.1–378.102

Compounds of the general formula Id where $R^1$ is methyl, $R^2$ is Cl, $R^{11}$ is n-propyl, $R^{12}$ is methylsulfonyl and where for each individual compound the substituents $R^3$, $R^8$ and $R^9$ correspond to one line of Table C.

Table 379: Compounds 379.1–379.102

Compounds of the general formula Id where $R^1$ is methyl, $R^2$ is Cl, $R^{11}$ is methyl, $R^{12}$ is ethylsulfonyl and where for each individual compound the substituents $R^3$, $R^8$ and $R^9$ correspond to one line of Table C.

Table 380: Compounds 380.1–380.102

Compounds of the general formula Id where $R^1$ is methyl, $R^2$ is Cl, $R^{11}$ is ethyl, $R^{12}$ is ethylsulfonyl and where for each individual compound the substituents $R^3$, $R^8$ and $R^9$ correspond to one line of Table C.

Table 381: Compounds 381.1–381.102

Compounds of the general formula Id where $R^1$ is methyl, $R^2$ is Cl, $R^{11}$ is n-propyl, $R^{12}$ is ethylsulfonyl and where for each individual compound the substituents $R^3$, $R^8$ and $R^9$ correspond to one line of Table C.

Table 382: Compounds 382.1–382.102

Compounds of the general formula Id where $R^1$ is methyl, $R^2$ is Cl, $R^{11}$ is methyl, $R^{12}$ is 4-methylphenylsulfonyl and where for each individual compound the substituents $R^3$, $R^8$ and $R^9$ correspond to one line of Table C.

Table 383: Compounds 383.1–383.102

Compounds of the general formula Id where $R^1$ is methyl, $R^2$ is Cl, $R^{11}$ is ethyl, $R^{12}$ is 4-methylphenylsulfonyl and where for each individual compound the substituents $R^3$, $R^8$ and $R^9$ correspond to one line of Table C.

Table 384: Compounds 384.1–384.102

Compounds of the general formula Id where $R^1$ is methyl, $R^2$ is Cl, $R^{11}$ is n-propyl, $R^{12}$ is 4-methylphenylsulfonyl and where for each individual compound the substituents $R^3$, $R^8$ and $R^9$ correspond to one line of Table C.

Table 385: Compounds 385.1–385.102

Compounds of the general formula Id where $R^1$ is methyl, $R^2$ is methylsulfonyl, $R^{11}$ is methyl and $R^{12}$ is hydrogen and where for each individual compound the substituents $R^3$, $R^8$ and $R^9$ correspond to one line of Table C.

Table 386: Compounds 386.1–386.102

Compounds of the general formula Id where $R^1$ is methyl, $R^2$ is methylsulfonyl, $R^{11}$ is ethyl, $R^{12}$ is hydrogen and where for each individual compound the substituents $R^3$, $R^8$ and $R^9$ correspond to one line of Table C.

Table 387: Compounds 387.1–387.102

Compounds of the general formula Id where $R^1$ is methyl, $R^2$ is methylsulfonyl, $R^{11}$ is n-propyl, $R^{12}$ is hydrogen and where for each individual compound the substituents $R^3$, $R^8$ and $R^9$ correspond to one line of Table C.

Table 388: Compounds 388.1–388.102

Compounds of the general formula Id where $R^1$ is methyl, $R^2$ is methylsulfonyl, $R^{11}$ is methyl, $R^{12}$ is methyl and where for each individual compound the substituents $R^3$, $R^8$ and $R^9$ correspond to one line of Table C.

Table 389: Compounds 389.1–389.102

Compounds of the general formula Id where $R^1$ is methyl, $R^2$ is methylsulfonyl, $R^{11}$ is ethyl, $R^{12}$ is methyl and where for each individual compound the substituents $R^3$, $R^8$ and $R^9$ correspond to one line of Table C.

Table 390: Compounds 390.1–390.102

Compounds of the general formula Id where $R^1$ is methyl, $R^2$ is methylsulfonyl, $R^{11}$ is n-propyl, $R^{12}$ is methyl and where for each individual compound the substituents $R^3$, $R^8$ and $R^9$ correspond to one line of Table C.

Table 391: Compounds 391.1–391.102

Compounds of the general formula Id where $R^1$ is methyl, $R^2$ is methylsulfonyl, $R^{11}$ is methyl, $R^{12}$ is ethyl and where for each individual compound the substituents $R^3$, $R^8$ and $R^9$ correspond to one line of Table C.

Table 392: Compounds 392.1–392.102

Compounds of the general formula Id where $R^1$ is methyl, $R^2$ is methylsulfonyl, $R^{11}$ is ethyl, $R^{12}$ is ethyl and where for each individual compound the substituents $R^3$, $R^8$ and $R^9$ correspond to one line of Table C.

Table 393: Compounds 393.1–393.102

Compounds of the general formula Id where $R^1$ is methyl, $R^2$ is methylsulfonyl, $R^{11}$ is n-propyl, $R^{12}$ is ethyl and where for each individual compound the substituents $R^3$, $R^8$ and $R^9$ correspond to one line of Table C.

Table 394: Compounds 394.1–394.102

Compounds of the general formula Id where $R^1$ is methyl, $R^2$ is methylsulfonyl, $R^{11}$ is methyl, $R^{12}$ is methylcarbonyl and where for each individual compound the substituents $R^3$, $R^8$ and $R^9$ correspond to one line of Table C.

Table 395: Compounds 395.1–395.102

Compounds of the general formula Id where $R^1$ is methyl, $R^2$ is methylsulfonyl, $R^{11}$ is ethyl, $R^{12}$ is methylcarbonyl and where for each individual compound the substituents $R^3$, $R^8$ and $R^9$ correspond to one line of Table C.

Table 396: Compounds 396.1–396.102

Compounds of the general formula Id where $R^1$ is methyl, $R^2$ is methylsulfonyl, $R^{11}$ is n-propyl, $R^{12}$ is methylcarbonyl and where for each individual compound the substituents $R^3$, $R^8$ and $R^9$ correspond to one line of Table C.

Table 397: Compounds 397.1–397.102

Compounds of the general formula Id where $R^1$ is methyl, $R^2$ is methylsulfonyl, $R^{11}$ is methyl, $R^{12}$ is ethylcarbonyl and where for each individual compound the substituents $R^3$, $R^8$ and $R^9$ correspond to one line of Table C.

Table 398: Compounds 398.1–398.102

Compounds of the general formula Id where $R^1$ is methyl, $R^2$ is methylsulfonyl, $R^{11}$ is ethyl, $R^{12}$ is ethylcarbonyl and where for each individual compound the substituents $R^3$, $R^8$ and $R^9$ correspond to one line of Table C.

Table 399: Compounds 399.1–399.102

Compounds of the general formula Id where $R^1$ is methyl, $R^2$ is methylsulfonyl, $R^{11}$ is n-propyl, $R^{12}$ is ethylcarbonyl and where for each individual compound the substituents $R^3$, $R^8$ and $R^9$ correspond to one line of Table C.

Table 400: Compounds 400.1–400.102

Compounds of the general formula Id where $R^1$ is methyl, $R^2$ is methylsulfonyl, $R^{11}$ is methyl, $R^{12}$ is methylsulfonyl and where for each individual compound the substituents $R^3$, $R^8$ and $R^9$ correspond to one line of Table C.

Table 401: Compounds 401.1–401.102

Compounds of the general formula Id where $R^1$ is methyl, $R^2$ is methylsulfonyl, $R^{11}$ is ethyl, $R^{12}$ is methylsulfonyl and where for each individual compound the substituents $R^3$, $R^8$ and $R^9$ correspond to one line of Table C.

Table 402: Compounds 402.1–402.102

Compounds of the general formula Id where $R^1$ is methyl, $R^2$ is methylsulfonyl, $R^{11}$ is n-propyl, $R^{12}$ is methylsulfonyl and where for each individual compound the substituents $R^3$, $R^8$ and $R^9$ correspond to one line of Table C.

Table 403: Compounds 403.1–403.102

Compounds of the general formula Id where $R^1$ is methyl, $R^2$ is methylsulfonyl, $R^{11}$ is methyl, $R^{12}$ is ethylsulfonyl and where for each individual compound the substituents $R^3$, $R^8$ and $R^9$ correspond to one line of Table C.

Table 404: Compounds 404.1–404.102

Compounds of the general formula Id where $R^1$ is methyl, $R^2$ is methylsulfonyl, $R^{11}$ is ethyl, $R^{12}$ is ethylsulfonyl and where for each individual compound the substituents $R^3$, $R^8$ and $R^9$ correspond to one line of Table C.

Table 405: Compounds 405.1–405.102

Compounds of the general formula Id where $R^1$ is methyl, $R^2$ is methylsulfonyl, $R^{11}$ is n-propyl, $R^{12}$ is ethylsulfonyl and where for each individual compound the substituents $R^3$, $R^8$ and $R^9$ correspond to one line of Table C.

Table 406: Compounds 406.1–406.102

Compounds of the general formula Id where $R^1$ is methyl, $R^2$ is methylsulfonyl, $R^{11}$ is methyl, $R^{12}$ is 4-methylphenylsulfonyl and where for each individual compound the substituents $R^3$, $R^8$ and $R^9$ correspond to one line of Table C.

Table 407: Compounds 407.1–407.102

Compounds of the general formula Id where $R^1$ is methyl, $R^2$ is methylsulfonyl, $R^{11}$ is ethyl, $R^{12}$ is 4-methylphenylsulfonyl and where for each individual compound the substituents $R^3$, $R^8$ and $R^9$ $R^1$–$R^8$ correspond to one line of Table C.

Table 408: Compounds 408.1–408.102

Compounds of the general formula Id where $R^1$ is methyl, $R^2$ is methylsulfonyl, $R^{11}$ is n-propyl, $R^{12}$ is 4-methylphenylsulfonyl and where for each individual compound the substituents $R^3$, $R^8$ and $R^9$ correspond to one line of Table C.

Table 409: Compounds 409.1–409.102

Compounds of the general formula Id where $R^1$ is methyl, $R^2$ is trifluoromethyl, $R^{11}$ is methyl and $R^{12}$ is hydrogen and where for each individual compound the substituents $R^3$, $R^8$ and $R^9$ correspond to one line of Table C.

Table 410: Compounds 410.1–410.102

Compounds of the general formula Id where $R^1$ is methyl, $R^2$ is trifluoromethyl, $R^{11}$ is ethyl, $R^{12}$ is hydrogen and where for each individual compound the substituents $R^3$, $R^8$ and $R^9$ correspond to is one line of Table C.

Table 411: Compounds 411.1–411.102

Compounds of the general formula Id where $R^1$ is methyl, $R^2$ is trifluoromethyl, $R^{11}$ is n-propyl, $R^{12}$ is hydrogen and where for each individual compound the substituents $R^3$, $R^8$ and $R^9$ correspond to one line of Table C.

Table 412: Compounds 412.1–412.102

Compounds of the general formula Id where $R^1$ is methyl, $R^2$ is trifluoromethyl, $R^{11}$ is methyl, $R^{12}$ is methyl and where for each individual compound the substituents $R^3$, $R^8$ and $R^9$ correspond to one line of Table C.

Table 413: Compounds 413.1–413.102

Compounds of the general formula Id where $R^1$ is methyl, $R^2$ is trifluoromethyl, $R^{11}$ is ethyl, $R^{12}$ is methyl and where for each individual compound the substituents $R^3$, $R^8$ and $R^9$ correspond to one line of Table C.

Table 414: Compounds 414.1–414.102

Compounds of the general formula Id where $R^1$ is methyl, $R^2$ is trifluoromethyl, $R^{11}$ is n-propyl, $R^{12}$ is methyl and where for each individual compound the substituents $R^3$, $R^8$ and $R^9$ correspond to one line of Table C.

Table 415: Compounds 415.1–415.102

Compounds of the general formula Id where $R^1$ is methyl, $R^2$ is trifluoromethyl, $R^{11}$ is methyl, $R^{12}$ is ethyl and where for each individual compound the substituents $R^3$, $R^8$ and $R^9$ correspond to one line of Table C.

Table 416: Compounds 416.1–416.102

Compounds of the general formula Id where $R^1$ is methyl, $R^2$ is trifluoromethyl, $R^{11}$ is ethyl, $R^{12}$ is ethyl and where for each individual compound the substituents $R^3$, $R^8$ and $R^9$ correspond to one line of Table C.

Table 417: Compounds 417.1–417.102

Compounds of the general formula Id where $R^1$ is methyl, $R^2$ is trifluoromethyl, $R^{11}$ is n-propyl, $R^{12}$ is ethyl and where for each individual compound the substituents $R^3$, $R^8$ and $R^9$ correspond to one line of Table C.

Table 418: Compounds 418.1–418.102

Compounds of the general formula Id where $R^1$ is methyl, $R^2$ is trifluoromethyl, $R^{11}$ is methyl, $R^{12}$ is methylcarbonyl and where for each individual compound the substituents $R^3$, $R^8$ and $R^9$ correspond to one line of Table C.

Table 419: Compounds 419.1–419.102

Compounds of the general formula Id where $R^1$ is methyl, $R^2$ is trifluoromethyl, $R^{11}$ is ethyl, $R^{12}$ is methylcarbonyl and where for each individual compound the substituents $R^3$, $R^8$ and $R^9$ correspond to one line of Table C.

Table 420: Compounds 420.1–420.102

Compounds of the general formula Id where $R^1$ is methyl, $R^2$ is trifluoromethyl, $R^{11}$ is n-propyl, $R^{12}$ is methylcarbonyl and where for each individual compound the substituents $R^3$, $R^8$ and $R^9$ correspond to one line of Table C.

Table 421: Compounds 421.1–421.102

Compounds of the general formula Id where $R^1$ is methyl, $R^2$ is trifluoromethyl, $R^{11}$ is methyl, $R^{12}$ is ethylcarbonyl and where for each individual compound the substituents $R^3$, $R^8$ and $R^9$ correspond to one line of Table C.

Table 422: Compounds 422.1–422.102

Compounds of the general formula Id where $R^1$ is methyl, $R^2$ is trifluoromethyl, $R^{11}$ is ethyl, $R^{12}$ is ethylcarbonyl and where for each individual compound the substituents $R^3$, $R^8$ and $R^9$ correspond to one line of Table C.

Table 423: Compounds 423.1–423.102

Compounds of the general formula Id where $R^1$ is methyl, $R^2$ is trifluoromethyl, $R^{11}$ is n-propyl, $R^{12}$ is ethylcarbonyl and where for each individual compound the substituents $R^3$, $R^8$ and $R^9$ correspond to one line of Table C.

Table 424: Compounds 424.1–424.102

Compounds of the general formula Id where $R^1$ is methyl, $R^2$ is trifluoromethyl, $R^{11}$ is methyl, $R^{12}$ is methylsulfonyl and where for each individual compound the substituents $R^3$, $R^8$ and $R^9$ correspond to one line of Table C.

Table 425: Compounds 425.1–425.102

Compounds of the general formula Id where $R^1$ is methyl, $R^2$ is trifluoromethyl, $R^{11}$ is ethyl, $R^{12}$ is methylsulfonyl and where for each individual compound the substituents $R^3$, $R^8$ and $R^9$ correspond to one line of Table C.

Table 426: Compounds 426.1–426.102

Compounds of the general formula Id where $R^1$ is methyl, $R^2$ is trifluoromethyl, $R^{11}$ is n-propyl, $R^{12}$ is methylsulfonyl and where for each individual compound the substituents $R^3$, $R^8$ and $R^9$ correspond to one line of Table C.

Table 427: Compounds 427.1–427.102

Compounds of the general formula Id where $R^1$ is methyl, $R^2$ is trifluoromethyl, $R^{11}$ is methyl, $R^{12}$ is ethylsulfonyl and where for each individual compound the substituents $R^3$, $R^8$ and $R^9$ correspond to one line of Table C.

Table 428: Compounds 428.1–428.102

Compounds of the general formula Id where $R^1$ is methyl, $R^2$ is trifluoromethyl, $R^{11}$ is ethyl, $R^{12}$ is ethylsulfonyl and where for each individual compound the substituents $R^3$, $R^8$ and $R^9$ correspond to one line of Table C.

Table 429: Compounds 429.1–429.102

Compounds of the general formula Id where $R^1$ is methyl, $R^2$ is trifluoromethyl, $R^{11}$ is n-propyl, $R^{12}$ is ethylsulfonyl and where for each individual compound the substituents $R^3$, $R^8$ and $R^9$ correspond to one line of Table C.

Table 430: Compounds 430.1–430.102

Compounds of the general formula Id where $R^1$ is methyl, $R^2$ is trifluoromethyl, $R^{11}$ is methyl, $R^{12}$ is 4-methylphenylsulfonyl and where for each individual compound the substituents $R^3$, $R^8$ and $R^9$ correspond to one line of Table C.

Table 431: Compounds 431.1–431.102

Compounds of the general formula Id where $R^1$ is methyl, $R^2$ is trifluoromethyl, $R^{11}$ is ethyl, $R^{12}$ is 4-methylphenylsulfonyl and where for each individual compound the substituents $R^3$, $R^8$ and $R^9$ correspond to one line of Table C.

Table 432: Compounds 432.1–432.102

Compounds of the general formula Id where $R^1$ is methyl, $R^2$ is trifluoromethyl, $R^{11}$ is n-propyl, $R^{12}$ is 4-methylphenylsulfonyl and where for each individual compound the substituents $R^3$, $R^8$ and $R^9$ correspond to one line of Table C.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method used, the compounds I, or the compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The herbicidal compositions or the active compounds can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The compounds I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, broadcasting or watering. The use forms depend on the intended aims; in any case, they should guarantee a very fine distribution of the active compounds according to the invention.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohenanol ketones such as cyclohexanone, strongly polar solvents, eg. amines such as N-methylpyrrolidone, and water. Aqueous use forms can be prepared from emulsion concentrates, suspensions, pastes, wettable powders or water-dispersible granules by adding water. To prepare emulsions, pastes or oil dispersions, 4-benzoylpyrazoles, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to the NMR spectrum).

The compounds I according to the invention can be formulated for example as follows:

I. 20 parts by weight of the compound No. 434.01 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 434.01 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 434.01 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. 434.01 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. 434.01 are mixed with 97 parts by weight of finely divided kaolin. This gives a dust which comprises 3% by weight of active compound.

VI. 20 parts by weight of the active compound No. 434.01 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 434.01 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 434.01 is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the activity spectrum and to achieve synergistic effects, the 4-benzoylpyrazoles I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-(aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The active compound application rates are from 0.001 to 3.0, preferably 0.01 to 1.0 kg/ha of active substance (a.s.), depending on the control target, the season, the target plants and the growth stage.

The syntheses of some starting materials are given below:

2,4-dichloro-3-(3'-hydroxy-3'-methyl-2'-oxetanyl)-benzoic acid (Compound 5.03)

Step a: Methyl 2,4-dichloro-3-(3'-trimethylsilyloxy-3'-methyl-2'-oxetanyl)-benzoate (Compound 5.01)

A solution of 10 g (0.043 mol) of methyl 2,4-dichloro-3-formylbenzoate and 8.4 g (0.065 mol) of 2-trimethylsilyloxy-propene in 1 l of n-hexane was irradiated at room temperature with a UV radiator (Heraeus, TQ 150W) for 24 h. The solvent was subsequently distilled off under reduced pressure and the residue was purified through 100 g of silica gel (0.04–0.06 mm) using mixtures of cyclohexane and ethyl acetate from 100:1 to 5:1 (v/v). 6.8 g of methyl 2,4-dichloro-3-(3'-trimethylsilyloxy-3'-methyl-2'-oxetanyl)benzoate.

1H NMR ($CDCl_3$) δ[ppm]: 1.3 (t, 3H), 3.9 (dd, 3H), 4.6 (m, 2H), 6.4 (d, 1H), 7.0 (s, 1H), 7.3 (m, 2H)

Step b: Methyl 2,4-dichloro-3-(3'-hydroxy-3'-methyl-2'-oxetanyl)-benzoate (Compound 5.02)

A solution of 14 g (0.039 mol) of methyl 2,4-dichloro-3-(3'-trimethylsilyloxy-3'-methyl-2'-oxetanyl)benzoate and 14 g of ion exchanger (Dowex 50 WX2, Serva) was stirred in 100 ml of methanol at room temperature for 12 h. The solvent was subsequently distilled off under reduced pressure and the residue was purified through 100 g of silica gel (0.04–0.06 mm) using mixtures of cyclohexane and ethyl acetate from 100:1 to 2:1 (v/v). 6.1 g of methyl 2,4-dichloro-3-(3'-hydroxy-3'-methyl-2'-oxetanyl)benzoate were obtained.

1H NMR ($CDCl_3$) δ[ppm]: 1.7 (s, 3H), 3.9 (s, 3 H), 4.6 (d, 1H), 4.8 (d, 1H), 6.3 (s, 1H), 7.4 (d, 1H), 7.6 (d, 1H)

alternatively:

Step c: Methyl 2,4-dichloro-3-(3,-hydroxy-3'-methyl-2'-oxetanyl)benzoate (Compound 5.02)

A solution of 1 g (0.003 mol) of methyl 2,4-dichloro-3-(3'-trimethylsilyloxy-3'-methyl-2'-oxetanyl)benzoate and 5 ml of a 10% strength methanolic solution of hydrogen chloride in 30 ml of methanol was stirred at room temperature for 12 h. The solvent was subsequently distilled off under reduced pressure and the residue was taken up in diethyl ether. This ether solution was washed neutral with water, dried with sodium sulfate and filtered and the solvent was distilled off under reduced pressure. 0.7 g of methyl 2,4-dichloro-3-(3'-hydroxy-3'-methyl-2'-oxetanyl)benzoate was obtained.

1H NMR ($CDCl_3$) δ[ppm]: 1.7 (s, 3H), 3.9 (s, 3 H), 4.6 (d, 1H), 4.8 (d, 1H), 6.3 (s, 1H), 7.4 (d, 1H), 7.6 (d, 1H)

Step d: 2,4-Dichloro-3-(3'-hydroxy-3'-methyl-2'-oxetanyl) benzoic acid (Compound 5.03)

A solution of 4.9 g (0.013 mol) of methyl 2,4-dichloro-3-(3'-hydroxy-3'-methyl-2'-oxetanyl)-benzoate and 0.5 g (0.020 mol) of lithium hydroxide was stirred at 0° C. in a mixture of 20 ml of tetrahydrofuran and 20 ml of water for 12 h. The solution was subsequently adjusted to pH 1–2 using 10% strength aqueous hydrochloric acid and extracted with diethyl ether. The combined organic phases were subsequently dried with sodium sulfate and filtered and the solvent was distilled off under reduced pressure. 3.5 g of 2,4-dichloro-3-(3'-hydroxy-3'-methyl-2'-oxetanyl)benzoic acid were obtained.

1H NMR ($CDCl_3$) δ[ppm]: 2.5 (s, 3H), 4.7 (d, 1 H), 4.9 (d, 1H), 6.4 (s, 1H), 7.4 (d, 1H), 7.7 (d, 1H), 8.6 (broad s, 1 H)

In addition to the above compounds further benzoic acid derivatives of the formula Vd which were prepared or are preparable in a similar manner are listed in Table 433 below.

TABLE 433

Vd

| No. | $R^1$ | $R^2$ | $R^4$ | $R^5$ | $R^6$ | $R^7$ | $R^{14}$ | 1H NMR [ppm] |
|---|---|---|---|---|---|---|---|---|
| 433.04 | Cl | Cl | $—C(CH_3)_3$ | $—OSi(CH_3)_3$ | H | H | $—OCH_3$ | 0.1(s, 9H), 1.2(s, 12H), 4.0(s, 3H), 4.7(d, 1H), 5.1(d, 1H), 6.5(s, 1H), 7.4(d, 1H), 7.6(d, 1H) |
| 433.05 | Cl | Cl | $—C(CH_3)_3$ | —OH | H | H | $—OCH_3$ | 1.2(s, 12H), 4.0(s, 3H), 4.6(d, 1H), 5.1(d, 1H), 6.4(s, 1H), 7.3(d, 1H), 7.6(d, 1H) |
| 433.06 | Cl | Cl | $—C(CH_3)_3$ | —OH | H | H | —OH | 0.9(s, 12H), 4.5(d, 1H), 4.7(d, 1H), 6.4(s, 1H), 7.2(d, 1H), 7.5(d, 1H) |
| 433.07 | Cl | Cl | H | $—CH_2CH_2O—$ | | H | $—OCH_3$ | 2.3(m, 2H), 3.6(m, 2H), 3.9(s, 3H), 4.4(d, 1H), 5.2(m, 1H), 5.4(m, 1H), 6.1(d, 1H), 7.3(d, 1H), 7.6(d, 1H) |
| 433.08 | Cl | Cl | H | $—CH_2CH_2O—$ | | H | —OH | |
| 433.09 | Cl | Cl | H | $—CH_2CH_2CH_2O—$ | | H | $—OCH_3$ | 1.6(m, 2H), 2.2(m, 2H), 3.8(m, 1H), 3.9(s, 3H), 4.9(m, 1H), 6.1(d, 1H), 7.3(d, 1H), 7.5(d, 1H) |
| 433.10 | Cl | Cl | H | $—CH_2CH_2CH_2O—$ | | H | —OH | |

Preparation of the end products 4-(2',4'-Dichloro-3'-(3"-hydroxy-3"-methyl-2"-oxetanyl-benzoyl)-2-ethyl-3-hydroxypyrazole (Compound 434.01)

A solution of 1.40 g (0.005 mol) of 2,4-dichloro-3-(3'-hydroxy-3'-methyl-2'-oxetanyl)-benzoic acid, 0.57 g (0.005 mol) of 2-ethyl-3-hydroxypyrazole and 1.08 g (0.005 mol) of dicyclohexylcarbodiimide in 50 ml if dry tetrahydrofuran was stirred at room temperature for 12 h. The precipitate was subsequently filtered off with suction and the filtrate was taken up in water. This aqueous solution was extracted with ethyl acetate. The combined organic phases were dried with sodium sulfate and filtered and the solvent was distilled off under reduced pressure. The oily residue was purified through 50 g of silica gel (0.04–0.06 mm) using a mixture of cyclohexane and ethyl acetate of 10:1 (v/v).

The resulting colorless oil was taken up in 10 ml of acetonitrile, admixed with 0.3 g (0.003 mol) of triethylamine and 0.1 g (0.001 mol) of trimethylsilyl cyanide and refluxed for 4 h. After cooling, the solvent was removed under reduced pressure and the residue was taken up in water. The aqueous phase was adjusted to pH 1–2 using 10% strength aqueous hydrochloric acid and extracted with ethyl acetate. The combined organic phases were subsequently washed neutral with water and dried with sodium sulfate and the solvent was distilled off under reduced pressure. 0.3 g of 4-(2',4'-dichloro-3'-(3"-hydroxy-3"-methyl-2"-oxetanyl-benzoyl)-2-ethyl-3-hydroxypyrazole, which was purified by precipitation on methyl tert-butyl ether using petroleum ether.

TABLE 434

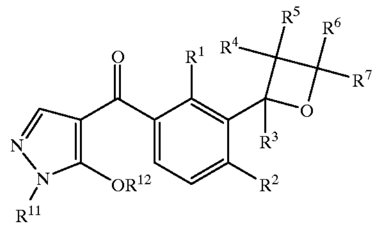

| No. | $R^1$ | $R^2$ | $R^3$ | $R^4$ | $R^5$ | $R^6$ | $R^7$ | $R^{11}$ | $R^{12}$ | Physical data 1H-NMR [ppm] m.p. [° C.] |
|---|---|---|---|---|---|---|---|---|---|---|
| 434.01 | Cl | Cl | H | $CH_3$ | OH | H | H | $C_2H_5$ | H | 1.3(t, 3H), 1.7(s, 3H), 3.9(dd, 2H), 4.6(m, 2H), 6.4(d, 1H), 7.0(d, 1H), 7.3(m, 3H) |
| 434.02 | Cl | Cl | H | H | $—OCH_2CH_2—$ | | H | $C_2H_5$ | H | 85 |

USE EXAMPLES

The herbicidal activity of the 4-benzoylpyrazoles of the Formula I was demonstrated by greenhouse experiments:

The culture containers used were plastic pots containing loamy sand with approximately 3.0% of humus as the substrate. The seeds of the test plants were sown separately for each species.

For the pre-emergence treatment, the active compounds, which have been suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants, unless this was adversely effected by the active compounds.

For the post-emergence treatment, the test plants were first grown to a height of 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.5 or 0.25 kg/ha of a.s.

Depending on the species, the plants were kept at 10–25° C. or 20–35° C . The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments belonged to the following species:

| Scientific name | Common name | Abbreviation |
|---|---|---|
| *Echinochloa crus-galli* | barnyard-grass | ECHCG |
| *Setaria faberii* | giant foxtail | SETFA |
| *Setaria viridis* | green foxtail | SETVI |
| *Chenopodium album* | lambsquarters (goosefoot) | CHEAL |
| *Polygonum persicaria* | ladythumb | POLPE |
| *Solanum nigrum* | black nightshade | SOLNI |

TABLE 435

Herbicidal activity when applied by the post-emergence method (greenhouse)

434.01

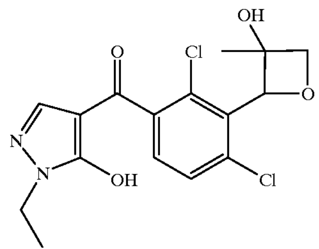

| Example No. Application rate (kg/ha of a.s.) | 0.5 | 0.25 |
|---|---|---|
| Test plants | | |
| ECHCG | 95 | 95 |
| SETFA | 98 | 95 |
| SETVI | 95 | 95 |
| CHEAL | 98 | 98 |
| POLPE | 98 | 95 |

TABLE 435-continued

Herbicidal activity when applied by the post-emergence method (greenhouse)

434.01

| Example No. Application rate (kg/ha of a.s.) | 0.5 | 0.25 |
|---|---|---|
| SOLNI | 95 | 95 |

We claim:

1. A carboxylic acid compound of formula Va or Vb

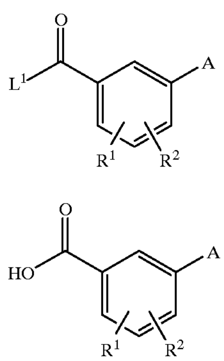

wherein $L^1$ is a nucleophilically replaceable leaving group selected from the group consisting of halogen, hetaryl and carboxylate;

A is a radical of formula IIIa or formula IIIb

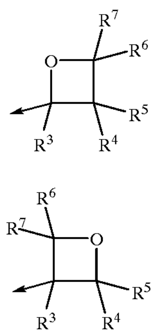

$R^1$ and $R^2$ are independently selected from the group consisting of: hydrogen, mercapto, nitro, halogen, cyano, thiocyanato, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl, —$OR^{10}$, —$OCOR^{10}$, —$OSO_2R^{10}$, —$S(O)_nR^{10}$, —$SO_2OR^{10}$, —$SO_2NR^3R^{10}$, —$NR^{10}SO_2R^{10}$ and —$NR^{10}COR^{10}$;

$R^3$ is hydrogen, $C_1$–$C_6$-alkyl or phenyl, where the alkyl and phenyl radicals mentioned may be partially or fully halogenated and/or may carry one to three of the following groups:

hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted;

$R^4$, $R^5$, $R^6$ and $R^7$ are independently selected from the group consisting of:

hydrogen, hydroxyl, mercapto, amino, halogen, $C_1$–$C_6$-alkyl, $C_3$–$C_6$-cycloalkyl, $C_4$–$C_6$-Cycloalkenyl, phenyl, —$OR^{10}$, —$S(O)_nR^{10}$, —$OS(O)_nR^{10}$, —$PO(OR^{10})_2$, —$NR^3R^{10}$, —$Si(R^{10})_3$ and —$OCOR^{10}$, where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$, —$Si(R^{10})_3$, —$OCOR^{10}$ are unsubstituted or partially or fully halogenated, and the unsubstituted or partially halogenated alkyl, cycloalkyl and $R^3$ radicals optionally carry one to three of the following groups: hydroxyl, mercapto, amino, cyano, $R^{10}$, —$OR^{10}$, —$SR^{10}$—$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted, and the unsubstituted or partially halogenated $R^{10}$ radicals optionally carry one to three of the following groups: hydroxyl, mercapto, amino, cyano, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted; or $R^4$ and $R^5$ together form a $C_2$–$C_5$-alkylene or $C_2$–$C_5$-alkenylene chain which may be interrupted once or twice by a nitrogen or an oxygen atom, or may form a group =X, where X is an oxygen atom or a group $CR^3R^{10}$, $NR^{10}$, $NNR^3R^{10}$, or $NOR^{10}$; or $R^5$ and $R^6$ together form a $C_3$–$C_4$-alkylene or $C_3$–$C_4$-alkenylene chain which may be interrupted by a nitrogen or an oxygen atom, in the event that $R^5$ and $R^6$ are attached to adjacent carbon atoms and that $R^4$ and $R^7$ are each hydrogen; or $R^6$ and $R^7$ together form a $C_2$–$C_5$-alkylene or $C_2$–$C_5$-alkenylene chain which may be interrupted once or twice by a nitrogen or an oxygen atom, or may form a group =X, where X is an oxygen atom or a group $CR^3R^{10}$, $NR^{10}$, $NNR^3R^{10}$, or $NOR^{10}$;

n is zero, one, two;

$R^{10}$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl, where the alkyl radicals mentioned may be partially or fully halogenated and/or may carry one to three of the following groups:

hydroxyl, mercapto, amino, cyano, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted.

2. A process for preparing a benzoic ester of formula Vc,

Vc

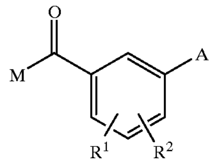

wherein

M is $C_1$–$C_6$-alkoxy;

A is a radical of formula IIIa

IIIa

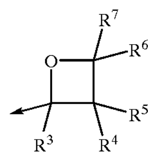

$R^1$ and $R^2$ are independently selected from the group consisting of:

hydrogen, mercapto, nitro, halogen, cyano, thiocyanato, $C_1$–$C_6$-alkyl, $C_l$–$C_6$-haloalkyl, $C_1$–$C_6$-alkoxy, $C_2$–$C_6$-alkenyl, $C_2$–$C_6$-alkynyl, —$OR^{10}$, —$OCOR^{10}$, —$OSO_2R^{10}$, —$S(O)_nR^{10}$, —$SO_2ORO_{10}$, —$SO_2NR^3R^{10}$, —$NR^{10}SO_2R^{10}$ and —$NR^{10}COR^{10}$;

$R^3$ is hydrogen, $C_1$–$C_6$-alkyl or phenyl, where the alkyl and phenyl radicals mentioned may be partially or fully halogenated and/or may carry one to three of the following groups:

hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted;

$R^4$, $R^5$, $R^6$ and $R^7$ are independently selected from the group consisting of:

hydrogen, hydroxyl, mercapto, amino, halogen, $C_1$–$C_6$-alkyl, $C_3$–$C_6$-cycloalkyl, $C_4$–$C_6$-cycloalkenyl, phenyl, —$OR^{10}$, —$S(O)_nR^{10}$, —$OS(O)_nR^{10}$, —$PO(OR^{10})_2$, —$NR^3R^{10}$, —$Si(R^{10})_3$ and —$OCOR^{10}$, where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$, —$Si(R^{10})_3$, —$OCOR^{10}$ are unsubstituted or partially or fully halogenated, and the unsubstituted or partially halogenated alkyl, cycloalkyl and $R^3$ radicals optionally carry one to three of the following groups: hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted, and the unsubstituted or partially halogenated $R^{10}$ radicals optionally carry one to three of the following groups: hydroxyl, mercapto, amino, cyano, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted; or $R^4$ and $R^5$ together form a $C_2$–$C_5$-alkylene or $C_2$–$C_5$-alkenylene chain which may be interrupted once or twice by a nitrogen or an oxygen atom, or may form a group =X, where X is an oxygen atom or a group $CR^3R^{10}$, $NR^{10}$, $NNR^3R^{10}$, or $NOR^{10}$; or $R^5$ and $R^6$ together form a $C_3$–$C_4$-alkylene or $C_3$–$C_4$-alkenylene chain which may be interrupted by a nitrogen or an oxygen atom, in the event that $R^5$ and $R^6$ are attached to adjacent carbon atoms and that $R^4$ and $R^7$ are each hydrogen; or $R^6$ and $R^7$ together form a $C_2$–$C_5$-alkylene or $C_2$–$C_5$-alkenylene chain which may be interrupted once or twice by a nitrogen or an oxygen atom, or may form a group =X, where X is an oxygen atom or a group $CR^3R^{10}$, $NR^{10}$, $NNR^3R^{10}$, or $NOR^{10}$;

n is zero, one, two;

$R^{10}$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl, where the alkyl radicals mentioned may be partially or fully halogenated and/or may carry one to three of the following groups:

hydroxyl, mercapto, amino, cyano, $C_1$–$C_4$-alkyliminooxy, $C_1$–$C_4$-alkoxyamino, $C_1C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted.

which comprises irradiating an aldehyde of formula IX or a ketone of formula X

IX

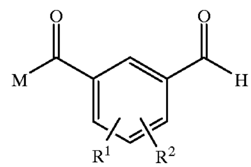

X

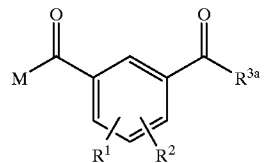

wherein $R^{3a}$ is a radical $R^3$ different from hydrogen, in the presence of an olefin of formula XI

XI

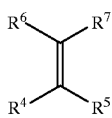

in the UV range.

3. The carboxylic acid compound defined in claim 1, wherein $R^4$–$R^7$ are each hydrogen, hydroxyl, mercapto, amino, halogen, $C_1$–$C_6$-alkyl, $C_3$–$C_6$-cycloalkyl, phenyl, —$OR^{10}$, —$S(O)_nR^{10}$, —$OS(O)_nR^{10}$, —$PO(OR^{10})_2$, —$NR^3R^{10}$, —$Si(R^{10})_3$ or —$OCOR^{10}$, where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$, —$Si(R^{10})_3$, —$OCOR^{10}$ are unsubstituted or partially or fully halogenated, and the unsubstituted or partially halogenated alkyl, cycloalkyl and $R^3$ radicals optionally carry one to three of the following groups: hydroxyl, mercapto, amino, cyano, $R^{10}$, —$OR^{10}$, —$SR^{10}$, —$NR^3R^{10}$, =$NOR_{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted, and the unsubstituted or partially halogenated $R^{10}$ radicals optionally carry one to three of the following groups: hydroxyl, mercapto, amino, cyano, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals may in turn be substituted.

4. The carboxylic acid compound defined in claim 1, wherein $R^4$ and $R^5$ together form a $C_2$–$C_5$-alkylene- or $C_2$–$C_5$-alkenylene chain which may be interrupted once or twice by a nitrogen or an oxygen atom, or form a group =X, where X is an oxygen atom or a group $CR^3R^{10}$, $NR^{10}$ or $NOR^{10}$; and/or $R^6$ and $R^7$ together form a $C_2$–$C_5$-alkylene or $C_2$–$C_5$-alkenylene chain which may be interrupted once or twice by a nitrogen or an oxygen atom, or form a group =X, where X is an oxygen atom or a group $CR^3R^{10}$, $NR^{10}$ or $NOR^{10}$.

5. The carboxylic acid compound defined in claim 1, wherein $R^5$ and $R^6$ together, if they are attached to adjacent carbon atoms and if $R^4$ and $R^7$ are each hydrogen, form a $C_3$–$C_4$-alkylene or $C_3$–$C_4$-alkenylene chain which may be interrupted by a nitrogen or an oxygen atom.

6. The carboxylic acid compound defined in claim 1, wherein $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$.

7. The carboxylic acid compound defined in claim 1, wherein $R^1$ is nitro, halogen, $C_1$–$C_6$-haloalkyl, —$OR^5$ or —$SO_2R^7$.

8. The carboxylic acid compound defined in claim 1, wherein $R^2$ is hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$alkynyl, —$OR^5$ —$S(O)_nR^7$.

9. The carboxylic acid compound defined in claim 1, wherein $R^2$ is hydrogen, nitro, halogen, $C_1$–$C_6$-alkyl, $C_1$–$C_6$-haloalkyl, —$OR^5$ or —$SO_2R^7$.

10. The carboxylic acid compound defined in claim 1, wherein $R^4$–$R^7$ are each hydrogen, hydroxyl, mercapto, amino, halogen, $C_1$–$C_4$-alkyl, $C_5$–$C_6$-cycloalkyl, $C_5$–$C_6$-cycloalkenyl, phenyl, —$OR^{10}$, —$S(O)_nR^{10}$, —$OS(O)_n R^{10}$, —$PO(OR^{10})_2$, —$NR^3R^{10}$, —$Si(R^{10})_3$ or —$OCOR^{10}$, where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$, —$Si(R^{10})_3$ —$OCOR^{10}$ are unsubstituted or partially or fully halogenated and/or carry one to three of the following groups: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;

$R^4$ and $R^5$ together form a $C_2$–$C_5$-alkylene or $C_2$–$C_5$-alkenylene chain which may be interrupted once or twice by an oxygen atom, or form a group =X, where X is an oxygen atom or $NR^{10}$;

$R^6$ and $R^7$ together form a $C_2$–$C_5$-alkylene or $C_2$–$C_5$-alkenylene chain which may be interrupted once or twice by an oxygen atom, or form a group =X, where X is an oxygen atom or $NR^{10}$;

n is two;

$R^5$ and $R^6$ together, if they are attached to adjacent carbon atoms and $R^4$ and $R^7$ are each hydrogen, form a $C_3$–$C_4$-alkylene or $C_3$–$C_4$-alkenylene chain which may be interrupted by a nitrogen or an oxygen atom.

11. The carboxylic acid compound defined in claim 1, wherein $R^4$–$R^7$ are each hydrogen, hydroxyl, amino, halogen, $C_1$–$C_4$-alkyl, $C_5$–$C_6$-cycloalkyl, phenyl, —$OR^{10}$, —$SO_2R^{10}$, —$OSO_2R^{10}$, —$PO(OR^{10})_2$, —$NR^3R^{10}$ or —$OCOR^{10}$, where the alkyl and cycloalkyl radicals mentioned and $R^3$ and $R^{10}$ of the radicals —$OR^{10}$, —$SO_2R^{10}$, —$OSO_2R^{10}$, —$PO(OR^{10})_2$, —$NR^3R^{10}$, —$OCOR^{10}$ are unsubstituted or partially or fully halogenated, and the unsubstituted or partially halogenated alkyl, cycloalkyl and $R^3$ radicals optionally carry one to three of the following groups: hydroxyl, amino, cyano, $R^{10}$, —$OR^{10}$, —$NR^3R^{10}$, —$OCOR^{10}$, —$CO_2R^{10}$, $C_1$–$C_4$-alkylcarbonyl, $C_1$–$C_4$-alkylsulfonyl, phenyl, benzyl, phenoxy and benzyloxy, where the last four radicals mentioned may in turn be substituted, and the unsubstituted or partially halogenated $R^{10}$ radicals optionally carry one to three of the following groups: hydroxyl, amino, cyano, $C_1$–$C_4$-alkylcarbonyl, $C_1$–$C_4$-alkylsulfonyl, phenyl, benzyl, phenoxy and benzyloxy, where the last four radicals mentioned may in turn be substituted.

12. The carboxylic acid compound defined in claim 1, wherein $R^4$ and $R^5$ together form a $C_2$–$C_5$-alkylene or $C_2$–$C_5$-alkenylene chain which may be interrupted once or twice by an oxygen atom, or form a group =X where X is an oxygen atom; and/or $R^6$ and $R^7$ together form a $C_2$–$C_5$-alkylene or $C_2$–$C_5$-alkenylene chain which may be interrupted once or twice by an oxygen atom, or form a group =X where X is an oxygen atom.

13. The carboxylic acid compound defined in claim 1, wherein $R^5$ and $R^6$ together, if they are attached to adjacent carbon atoms and if $R^4$ and $R^7$ are each hydrogen, form a $C_3$–$C_4$-alkylene or $C_3$–$C_4$-alkenylene chain which may be interrupted by a nitrogen or an oxygen atom.

14. The carboxylic acid compound defined in claim 1, wherein $R^{10}$ is hydrogen, $C_1$–$C_4$-alkyl, $C_1$–$C_4$-haloalkyl, $C_2$–$C_4$-alkenyl, phenyl or phenyl-$C_1$–$C_4$-alkyl, where the phenyl radical mentioned may be partially or fully halogenated and/or may carry one to three of the following groups: nitro, cyano, $C_1$–$C_4$-alkyl, $C_l$–$C_4$-haloalkyl, $C_1$–$C_4$-alkoxy, $C_1$–$C_4$-haloalkoxy, $C_1$–$C_4$-alkoxycarbonyl.

* * * * *

UNITED STATES PATENT AND TRADEMARK OFFICE

CERTIFICATE OF CORRECTION

PATENT NO. : 6,407,268 B1
DATED : June 18, 2002
INVENTOR(S) : Engel et al.

It is certified that error appears in the above-identified patent and that said Letters Patent is hereby corrected as shown below:

Column 88,
Line 17, "Cycloalkenyl" should be -- cycloalkenyl --.

Column 89,
Line 35, "$C_{I}$-$C_6$-" should be -- $C_1$-$C_6$- --.

Column 90,
Line 41, "$C_1C_4$-" should be -- $C_1$-$C_4$- --.

Column 94,
Line 7, "$C_{I}$-$C_4$-" should be -- $C_1$-$C_4$- --.

Signed and Sealed this

Tenth Day of September, 2002

*Attest:*

JAMES E. ROGAN

*Attesting Officer*

*Director of the United States Patent and Trademark Office*